US008065360B2

(12) United States Patent
Jung et al.

(10) Patent No.: US 8,065,360 B2
(45) Date of Patent: *Nov. 22, 2011

(54) ACQUISITION AND PARTICULAR ASSOCIATION OF INFERENCE DATA INDICATIVE OF AN INFERRED MENTAL STATE OF AN AUTHORING USER AND SOURCE IDENTITY DATA

(75) Inventors: Edward K. Y. Jung, Bellevue, WA (US); Eric C. Leuthardt, St. Louis, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 453 days.

This patent is subject to a terminal disclaimer.

(21) Appl. No.: 12/229,517

(22) Filed: Aug. 21, 2008

(65) Prior Publication Data

US 2009/0292724 A1 Nov. 26, 2009

Related U.S. Application Data

(63) Continuation of application No. 12/154,686, filed on May 23, 2008, now Pat. No. 7,904,507, and a continuation-in-part of application No. 12/221,197, filed on Jul. 30, 2008, and a continuation-in-part of application No. 12/221,253, filed on Jul. 29, 2008, and a continuation-in-part of application No. 12/217,131, filed on Jun. 30, 2008, and a continuation-in-part of application No. 12/215,683, filed on Jun. 26, 2008, and a continuation-in-part of application No. 12/157,611, filed on Jun. 10, 2008.

(51) Int. Cl.
*G06F 15/16* (2006.01)
(52) U.S. Cl. .......... 709/203; 709/220; 707/100
(58) Field of Classification Search .......... 709/203, 709/220, 228; 707/3, 10
See application file for complete search history.

(56) References Cited

U.S. PATENT DOCUMENTS 5,715,374 A 2/1998 Heckerman et al.
(Continued)

OTHER PUBLICATIONS

Parc Research; "Content-Centric Networking: Parc's Strategy for Pioneering a Self-Organizing Network That Meets Information Needs"; pp. 1-4; Xerox Corporation; located at: http://www.parc.xerox.com/research/projects/networking/contentcentric/mediabackgrounder.html; printed on Mar. 2, 2009.
(Continued)

*Primary Examiner* — Khanh Dinh

(57) ABSTRACT

A computationally implemented method includes, but is not limited to: acquiring inference data indicative of an inferred mental state of an authoring user in connection with at least a particular item of an electronic message, acquiring source identity data providing one or more identities of one or more sources that is or are basis, at least in part, for the inference data indicative of the inferred mental state of the authoring user, associating the inference data indicative of the inferred mental state of the authoring user with the particular item; and associating the source identity data providing one or more identities of the one or more sources with the particular item. In addition to the foregoing, other method aspects are described in the claims, drawings, and text forming a part of the present disclosure.

39 Claims, 37 Drawing Sheets

U.S. PATENT DOCUMENTS

| | | | |
|---|---|---|---|
| 5,724,698 | A | 3/1998 | Mondragon |
| 5,740,549 | A | 4/1998 | Reilly et al. |
| 5,761,512 | A | 6/1998 | Breslau et al. |
| 6,523,009 | B1 | 2/2003 | Wilkins |
| 6,573,927 | B2 | 6/2003 | Parulski et al. |
| 7,406,307 | B2 | 7/2008 | Manto |
| 7,698,255 | B2* | 4/2010 | Goodwin et al. ............ 707/707 |
| 7,753,795 | B2 | 7/2010 | Harris et al. |
| 2002/0065836 | A1 | 5/2002 | Sasaki |
| 2002/0095089 | A1 | 7/2002 | Yamamoto et al. |
| 2002/0193670 | A1 | 12/2002 | Garfield et al. |
| 2003/0028647 | A1 | 2/2003 | Grosu |
| 2003/0191568 | A1* | 10/2003 | Breed ............................ 701/36 |
| 2004/0230549 | A1 | 11/2004 | Freer et al. |
| 2004/0236236 | A1 | 11/2004 | Yanagidaira et al. |
| 2005/0078804 | A1 | 4/2005 | Yomoda |
| 2006/0112111 | A1 | 5/2006 | Tseng et al. |
| 2007/0043590 | A1 | 2/2007 | Lee |
| 2007/0093965 | A1 | 4/2007 | Harrison et al. |
| 2008/0001600 | A1 | 1/2008 | deCharms |
| 2008/0059570 | A1 | 3/2008 | Bill |
| 2008/0114266 | A1 | 5/2008 | Shen et al. |
| 2008/0120129 | A1* | 5/2008 | Seubert et al. .................... 705/1 |
| 2008/0139889 | A1 | 6/2008 | Bagan |
| 2008/0162649 | A1 | 7/2008 | Lee et al. |
| 2008/0181381 | A1 | 7/2008 | Manto |
| 2008/0243825 | A1 | 10/2008 | Staddon et al. |
| 2009/0030886 | A1 | 1/2009 | Pandeya |
| 2010/0095362 | A1* | 4/2010 | Boberg et al. .................... 726/7 |

OTHER PUBLICATIONS

ABOUT.COM.: Email Webpage; printed on Aug. 15, 2008; p. 1 located at http://email.about.com/gi/dynamic/offsite.htm?zi=1/XJ&sdn=email&zu=http%3A%2F%2Fwww.pointofmail.com%2F.

Ambler et al.; "Salience and Choice: Neural Correlates of Shopping Decisions"; Psychology & Marketing; Apr. 2004; pp. 247-261; vol. 21; No. 4; Wiley Periodicals, Inc.

Appenzeller et al.; "The Mobile People Architecture—Technical Report: CSL-TR-99-777"; Jan. 1999; pp. 1-10 (12 pages total incl. title page/abstract and copyright information); located at ftp://reports.stanford.edu/pub/cstr/reports/csl/99/777/CSL-TR-99-777.pdf; Stanford University.

Bergman et al.; "A Personal Email Assistant"; HPInvent Website; printed on Aug. 15, 2008; pp. 1-22 (23 pages total incl. summary page); located at http://www.hpl.hp.com/techreports/2002/HPL-2002-236.pdf; Hewlett-Packard Company 2002.

Cabeza et al.; "Imaging Cognition II: An Empirical Review of 275 PET and fMRI Studies"; Journal of Cognitive Neuroscience; 2000; pp. 1-47; vol. 12; No. 1; Massachusetts Institute of Technology.

CENTIPAID.COM; "Getting the Best Out of Surgemail's SPAM Features"; bearing dates of 2002-2006 and printed on Aug. 13, 2008; pp. 1-5; located at http://www.centipaid.com/en/support/surgemail.html; Centipaid Corporation.

Chance et al.; "A Novel Method for Fast Imaging of Brain Function, Non-Invasively, With Light"; Optics Express; May 11, 1998; pp. 411-423; vol. 2; No. 10; OSA.

Clearcontext; "User Guide"; bearing dates of 2003-2008 and printed on Aug. 15, 2008; pp. 1-4; located at http://www.clearcontext.com/user_guide/contacts.html; Clearcontext Corporation.

Communigatepro; "CommuniGate® Pro Version 5.1"; bearing dates of 1998-2007 and printed on Aug. 15, 2008; pp. 1-6; located at https://mx2.arl.org/Guide/default.html; Stalker Software, Inc.

Critical Path; "Critical Path: Putting Mobile Email in Context"; bearing a date of Aug. 11, 2005 and printed on Aug. 13, 2008; pp. 1-2; located at http://www.cbronline.com/article_feature.asp?guid=D9E4E0B0-BE6A-4928-8857-3A3682D852C1; CBR and CBRonline.com.

Goodmail Systems; "Certified Email: How it Works"; printed on Aug. 13, 2008; p. 1; located at http://www.goodmailsystems.com/products/certified-email/how_it_works.php.

Huang et al.; "MapWeb: A Location-Based Converged Communications Platform"; Bell Labs Technical Journal—Lucent Technologies Inc.; 2006; pp. 159-171; Wiley Periodicals, Inc.

Inovalive: "iNovaLive: Email Solutions Through Email Evolution website"; bearing a date of 2006 and printed on Aug. 15, 2008; pp. 1-2; located at http://inovalive.com/site/index; iNovaSoft Ltd.

Kenning et al.; "NeuroEconomics: An Overview from an Economic Perspective"; Brain Research Bulletin; 2005; pp. 343-354; vol. 67; Elsevier Inc.

Lee et al.; "What is 'Neuromarketing'? A Discussion and Agenda for Future Research"; International Journal of Psychophysiology; bearing dates of 2006 and 2007; pp. 199-204; vol. 63; Elsevier B.V.

Matthews et al.; "Applications of fMRI in Translational Medicine and Clinical Practice"; Nature Reviews/Neuroscience; Sep. 2006; pp. 732-744; vol. 7; Nature Publishing Group.

Murphy, Kevin; "Pay-Per-Email Scheme Draws Critics"; bearing a date of Feb. 7, 2006 and printed on Aug. 13, 2008; pp. 1-3; located at http://www.cbronline.com/article_news.asp?guid=A921B4EA-A489-4B5C-8053-423F46499767; CBR and CBRonline.com.

Nedos et al.; "LATTE: Location and Time Triggered Email"; pp. 1-14; located at https://www.cs.tcd.ie/publications/tech-reports/reports.04/TCD-CS-2004-32.pdf; Trinity College, Dublin, Ireland.

Parc Research; "Content Centric Networking"; bearing dates of 2002-2007; printed on Aug. 15, 2008; pp. 1-2; located at http://www.parc.xerox.com/research/projects/networking/contentcentric/default.html; Palo Alto Research Center Incorporated.

POINTOFMAIL.COM.; "Advanced Email Experience™"; bearing dates of 1999-2008 and printed on Aug. 15, 2008; p. 1; located at http://email.about.com/gi/dynamic/offsite.htm?zi=1/XJ&sdn=email&zu=http%3A%2F%2Fwww.readnotify.com%2F.

Roecker et al.; "Context-Dependent Email Notification Using Ambient Displays and Mobile Devices"; 2005; pp. 137-138; located at http://ieeexplore.ieee.org/iel5/10045/32238/01505288.pdf?tp=&isnumber=32238&arnumber=1505288; IEEE.

TECHCRUNCH.COM; "Seriosity to Fix Email Overload (Or Not)" blog; bearing a date of Feb. 28, 2007 and printed on Aug. 13, 2008; pp. 1-12; located at http://www.techcrunch.com/2007/02/28/seriosity-to-fix-email-overload-or-not/all-comments/#comments.

Terdiman, Daniel; "A Cure for E-Mail Attention Disorder?"; CNET News.com; Feb. 28, 2007 and printed on Aug. 13, 2008; pp. 1-4; located at http://news.com.com/2100-1038_3-6162798.html; CNET Networks, Inc., a CBS Company.

Tschabitscher, Heinz; "BigString.com—Free Email Service"; About.com: Email; printed on Aug. 13, 2008; pp. 1-2; located at http://email.about.com/od/freeemailreviews/gr/bigstring_com.htm.

Tschabitscher, Heinz; "Confimax—Certified Email Service"; About.com: Email; printed on Aug. 13, 2008; pp. 1-2; located at http://email.about.com/cs/oepluginreviews/gr/confimax.htm.

Tschabitscher, Heinz; "DidTheyReadIt—Certified Email Service"; About.com: Email; printed on Aug. 13, 2008; pp. 1-2; located at http://email.about.com/od/windowsreturnreceipts/gr/didtheyreadit.htm.

Tschabitscher, Heinz; "E-mail Secure—Certified Email Service"; About.com: Email; printed on Aug. 13, 2008; pp. 1-2; located at http://email.about.com/od/windowsreturnreceipts/gr/e_mailsecure.htm.

Tschabitscher, Heinz; "Pointofmail 5.5—Certified Email Service"; About.com: Email; printed on Aug. 13, 2008; pp. 1-2; located at http://email.about.com/od/windowsreturnreceipts/gr/pointofmail.htm.

Tschabitscher, Heinz; "ReadNotify—Certified Email Service"; About.com: Email; printed on Aug. 13, 2008; pp. 1-2; located at http://email.about.com/od/windowsreturnreceipts/gr/readnotify.htm.

TWITTER.COM website located at http://twitter.com; [No document provided].

Westen et al.; "Neural Bases of Motivated Reasoning: An fMRI Study of Emotional Constraints on Partisan Political Judgment in the 2004 U.S. Presidential Election"; Journal of Cognitive Neuroscience; 2006; pp. 1947-1958; vol. 18; No. 11; Massachusetts Institute of Technology.

U.S. Appl. No. 12/231,302, Jung et al.

U.S. Appl. No. 12/931,359, Jung et al.

U.S. Appl. No. 13/135,462, filed Jul. 5, 2011, Jung et al.

* cited by examiner

48 Sensor[s]

| 140 fMRI device | 145 Heart rate sensor device | 149 Skin characteristic sensor device |
| 141 fNIR device | 146 Blood pressure sensor device | 150 Voice response device |
| 142 EEG device | 147 Respiration sensor device | 151 Gaze tracking device |
| 143 MEG device | 148 Facial expression sensor device | 152 Iris response device |
| 144 Galvanic skin sensor device | | |

FIG. 2H

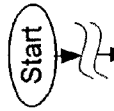
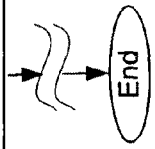

306 Associating the inference data indicative of the inferred mental state of the authoring user with the particular item

902 Including into the electronic message the inference data indicative of the inferred mental state of the authoring user

918 Including into the electronic message inference data indicative of the inferred mental state of the authoring user that was obtained based, at least in part, on one or more physical characteristics of the authoring user sensed during or proximate to an action in connection with the particular item and performed, at least in part, by the authoring user

936 Including into the electronic message inference data indicative of the inferred mental state of the authoring user that was obtained based, at least in part, on at least one of facial expression, skin characteristic, voice characteristic, eye movement, or iris dilation of the authoring user sensed during or proximate to the action in connection with the particular item

938 Including into the electronic message inference data indicative of the inferred mental state of the authoring user that was obtained based, at least in part, on data obtained in response to a functional magnetic resonance imaging procedure or a functional near infrared procedure performed on the authoring user during or proximate to the action in connection with the particular item

940 Including into the electronic message inference data indicative of the inferred mental state of the authoring user that was obtained based, at least in part, on data obtained in response to a magnetoencephalography (MEG) procedure or an electroencephalography (EEG) procedure performed on the authoring user during or proximate to the action in connection with the particular item

FIG. 9E

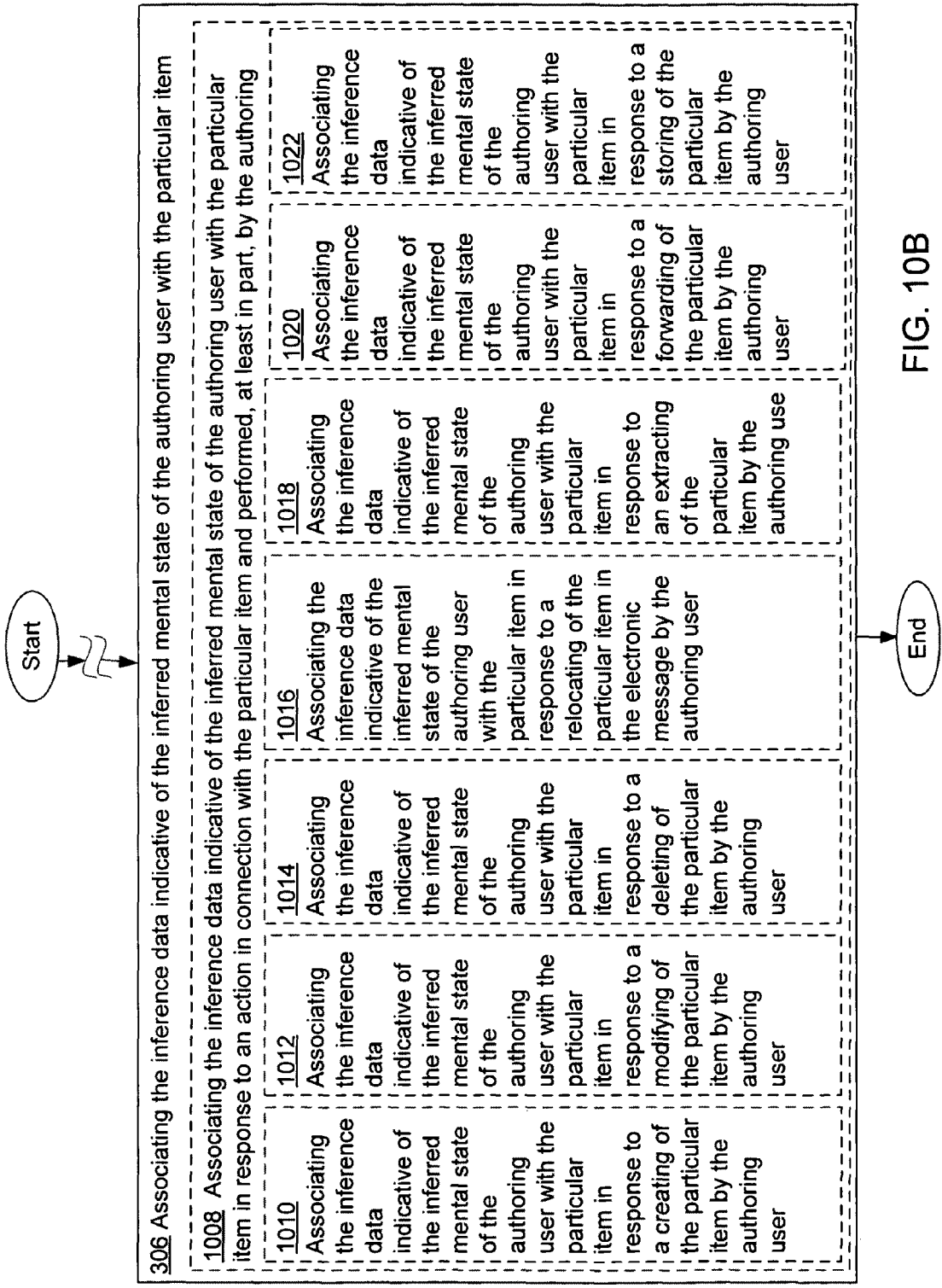

ACQUISITION AND PARTICULAR ASSOCIATION OF INFERENCE DATA INDICATIVE OF AN INFERRED MENTAL STATE OF AN AUTHORING USER AND SOURCE IDENTITY DATA

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application is related to U.S patent application Ser. No. 12/284,710, entitled ACQUISITION AND PARTICULAR ASSOCIATION OF INFERENCE DATA INDICATIVE OF INFERRED MENTAL STATES OF AUTHORING USERS, naming Edward K.Y. Jung, Eric C. Leuthardt, Royce A. Levien, Robert W. Lord, Mark A. Malamud, John D. Rinaldo, Jr. and Lowell L. Wood, Jr. as inventors, filed 23 Sep. 2008, which is currently co-pending, or is an application of which a currently co-pending application is entitled to the benefit of the filing date.

For purposes of the USPTO extra-statutory requirements, the present application is related to U.S. patent application Ser. No. 12/287,687, entitled ACQUISITION AND PRESENTATION OF DATA INDICATIVE OF AN EXTENT OF CONGRUENCE BETWEEN INFERRED MENTAL STATES OF AUTHORING USERS, naming Edward K.Y. Jung, Eric C. Leuthardt, Royce A. Levien, Robert W. Lord, Mark A. Malamud, John D. Rinaldo, Jr. and Lowell L. Wood, Jr. as inventors, filed 10 Oct. 2008, which is currently co-pending, or is an application of which a currently co-pending application is entitled to the benefit of the filing date.

For purposes of the USPTO extra-statutory requirements, the present application is related to U.S. patent application Ser. No. 12/288,801, entitled ACQUISITION AND PRESENTATION OF DATA INDICATIVE OF AN EXTENT OF CONGRUENCE BETWEEN INFERRED MENTAL STATES OF AUTHORING USERS, naming Edward K.Y. Jung, Eric C. Leuthardt, Royce A. Levien, Robert W. Lord, Mark A. Malamud, John D. Rinaldo, Jr. and Lowell L. Wood, Jr. as inventors, filed 14 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,686 now U.S. Pat. No. 7,904,507, entitled DETERMINATION OF EXTENT OF CONGRUITY BETWEEN OBSERVATION OF AUTHORING USER AND OBSERVATION OF RECEIVING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 23 May 2008, which is currently an application entitled to the benefit of the filing date.

For purposes of the USPTO extra-statutory requirements, the present application constitutes a continuation-in-part of U.S. patent application Ser. No. 12/157,611, entitled DETERMINATION OF EXTENT OF CONGRUITY BETWEEN OBSERVATION OF AUTHORING USER AND OBSERVATION OF RECEIVING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 10 Jun. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/215,683, entitled ACQUISITION AND ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 26 Jun. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/217,131, entitled ACQUISITION AND ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 30 Jun. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/221,253, entitled ACQUISITION AND PARTICULAR ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 29 Jul. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/221,197, entitled ACQUISITION AND PARTICULAR ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 30 Jul. 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

A computationally implemented method includes, but is not limited to: acquiring inference data indicative of an inferred mental state of an authoring user in connection with at least a particular item of an electronic message; acquiring source identity data providing one or more identities of one or more sources that is or are basis, at least in part, for the inference data indicative of the inferred mental state of the authoring user; associating the inference data indicative of the inferred mental state of the authoring user with the particular item; and associating the source identity data providing one or more identities of the one or more sources with the particular item. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for acquiring inference data indicative of an inferred mental state of an authoring user in connection with at least a particular item of an electronic message; means for acquiring source identity data providing one or more identities of one or more sources that is or are basis, at least in part, for the inference data indicative of the inferred mental state of the authoring user; means for associating the inference data indicative of the inferred mental state of the authoring user with the particular item; and means for associating the source identity data providing one or more identities of the one or more sources with the particular item. In addition to the foregoing, other system aspects are described in the claims, drawings, and text forming a part of the present disclosure.

A computationally implemented system includes, but is not limited to: circuitry for acquiring inference data indicative of an inferred mental state of an authoring user in connection with at least a particular item of an electronic message; circuitry for acquiring source identity data providing one or more identities of one or more sources that is or are basis, at least in part, for the inference data indicative of the inferred mental state of the authoring user; circuitry for associating the inference data indicative of the inferred mental state of the authoring user with the particular item; and circuitry for associating the source identity data providing one or more identities of the one or more sources with the particular item. In addition to the foregoing, other system aspects are described in the claims, drawings, and text forming a part of the present disclosure.

A computer program product including a signal-bearing medium bearing one or more instructions for acquiring inference data indicative of an inferred mental state of an authoring user in connection with at least a particular item of an electronic message; one or more instructions for acquiring source identity data providing one or more identities of one or more sources that is or are basis, at least in part, for the inference data indicative of the inferred mental state of the authoring user; one or more instructions for associating the inference data indicative of the inferred mental state of the authoring user with the particular item; and one or more instructions for associating the source identity data providing one or more identities of the one or more sources with the particular item. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2H shows another perspective of the one or more sensors 48 of FIG. 1.

FIG. 9E is a high-level logic flowchart of a process depicting more alternate implementations of the inclusion operation 918 of FIG. 9B.

FIG. 10B is a high-level logic flowchart of a process depicting some more alternate implementations of the inference data association operation 306 of FIG. 3.

DETAILED DESCRIPTION

Figure 1:
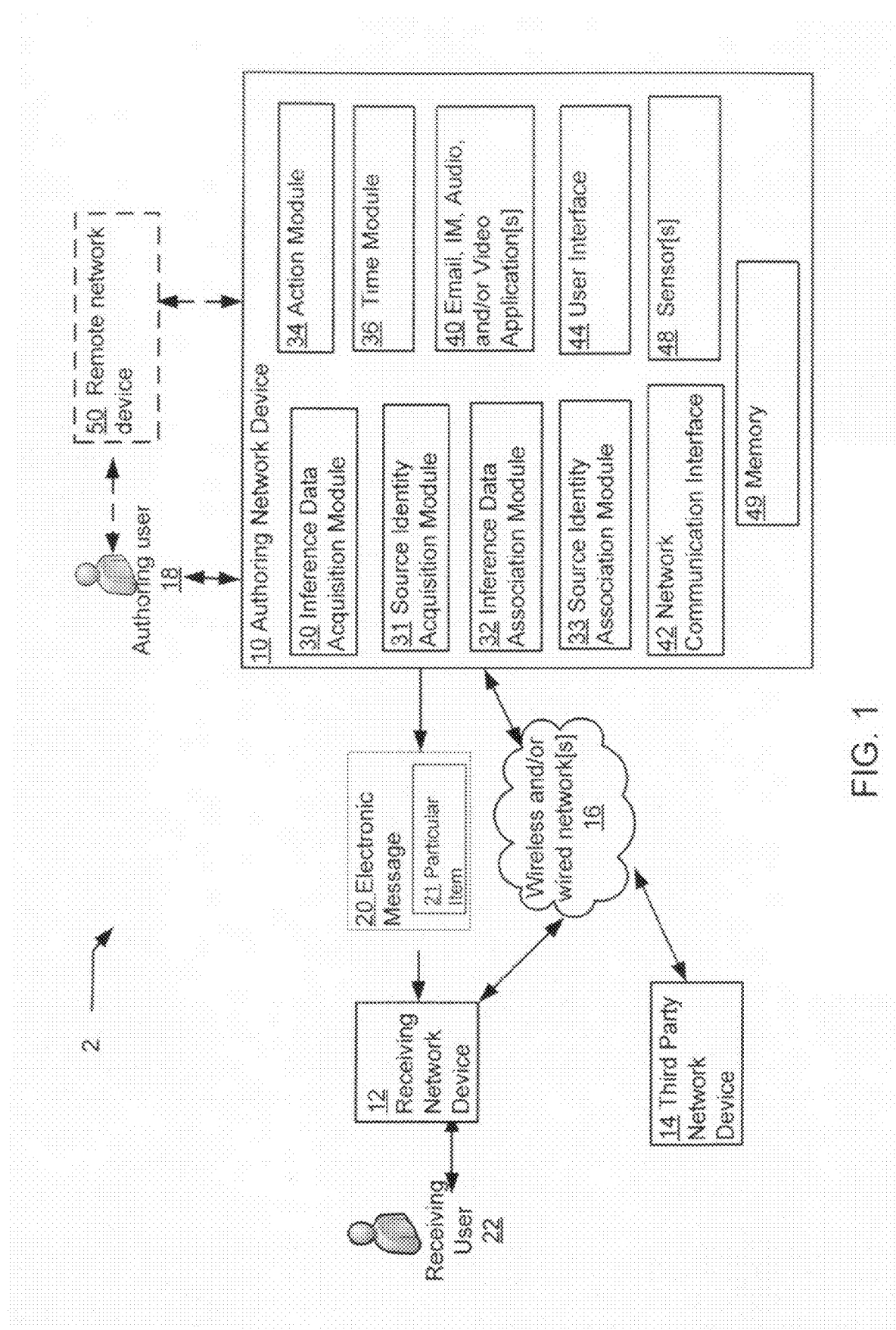
FIG. 1 shows a high-level block diagram of a network device operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example environment in which one or more aspects of various embodiments may be implemented. In the illustrated environment, an exemplary system 2 may include at least an authoring network device 10 that may be used by an authoring user 18 in order to, for example, communicate through one or more wireless and/or wired networks 16. In some implementations, the authoring network device 10 (and in some cases a remote network device 50) may be particularly designed and configured to facilitate the authoring user 18 in acquiring inference data indicative of an inferred mental state of the authoring user 18 in connection with a particular item 21 of an electronic message 20 and associating such data to the particular item 21. Additionally, the authoring network device 10 (as well as the remote network device 50 in some cases) may be further configured to acquire source identity data providing one or more identities of one or more sources that is or are the basis, at least in part, for the inference data indicative of the inferred mental state of the authoring user 18 in connection with the particular item 21, and to associate such data with the particular item 21. In doing so, a recipient of the electronic message 20, such as a receiving user 22 (e.g., via a receiving network device 12) or a third party (e.g., via a third party network device 14), may be facilitated in correctly interpreting the proper meaning and intent of the particular item 21 if and when the electronic message 20 is presented to the recipient.

In addition to acquiring and associating the inference data and the source identity data to the particular item 21, other types of information may be acquired and associated with the particular item 21. For instance, in some implementations, the authoring network device 10 may acquire and associate with the particular item 21 a time stamp and/or an indication of an action performed in connection with the particular item 21. In some cases, such information may be useful in associating the inference data (i.e., inference data indicative of the inferred mental state of the authoring user 18) with the particular item 21. Note that those skilled in the art will appreciate that although authoring user 18/receiving user 22 is depicted in the figures as an individual for sake of conceptual clarity, in some instances authoring user 18/receiving user 22 may be considered as examples of sequential users, unless context dictates otherwise.

In various implementations, the electronic message 20 may be an email message, a text message, an instant message (IM), an audio message, a video message, or another type of electronic message. The particular item 21 may be any part or portion of the electronic message 21. For example, if the electronic message 20 is an email message, then the particular item 21 may be a passage, a paragraph, a sentence, a word, a phrase, an image, a symbol, an icon, a number, a letter, a format of a word or phrase (e.g., bold), or any other part or portion of the email message.

As will be further described, an inferred mental state of a subject (e.g., authoring user 18 or receiving user 22) may be a mental state that has been inferred based, at least in part, on one or more sensed or measured physical characteristics of the subject. The term "physical characteristics" as used herein may refer to both external physical characteristics (e.g., facial expressions, skin characteristics, and/or iris characteristics) and/or physiological characteristics (e.g., blood oxygen or blood volume changes of a subject's brain, characteristics associated with the electrical activities of the subject's brain, cardiopulmonary characteristics, and so forth). In various embodiments, the sensing or measuring of the physical characteristics of the subject may be in connection with an "action" being executed by the subject with respect to a particular item 21.

For example, suppose the authoring user 18 creates and sends an email message (e.g., electronic message 20) containing a particular item 21, in this case, a passage that includes a humorous story, to the receiving user 22 with the intent to lighten the mood of the receiving user 22. The authoring network device 10 may be particularly designed and configured to acquire inference data indicative of an inferred mental state of the authoring user 18 in connection with the creation of the particular item 21 in the electronic message 20. In some implementations, this may be accomplished at least in part by, for example, sensing one or more physical characteristics of the authoring user 18 during or proximate to the creation of the particular item 21. The inference data indicative of the inferred mental state of the authoring user 18 may then be associated or tagged to the particular item 21 (e.g., passage).

In some implementations, after associating the inference data to the particular item 21, the inference data may then be provided or transmitted to a recipient (e.g., receiving user 22) in the electronic message 20 or by other means (e.g., in another electronic message). In doing so, the receiving user 22 may deduce the inferred mental state of the authoring user 18 in connection with the creation of the particular item 21 and may then be made aware of whether the receiving user 22 is misunderstanding the intent, tone, and/or meaning of the particular item 21 (e.g., the receiving user 22 becoming mistakenly distressed by the particular item 21 because the recipient misunderstood the tone of the humorous story) when viewing the particular item 21. That is, and as will be further described, by comparing the inferred mental state of the authoring user 18 in connection with the creation of the particular item 21 with an inferred mental state of the receiving user 22 during or proximate to the presentation to the receiving user 22 of the particular item 21, a determination may be made as to whether the receiving user 22 is properly understanding the meaning of the particular item 21 during or proximate to the presentation of the particular item 21.

The following example is provided that describes how inference data indicative of the inferred mental state of the authoring user 18 in connection with a particular item 21 may be provided and used by a receiving user 22 in accordance with some implementations. As described earlier, the receiving user 22 may be facilitated in understanding the proper intent and meaning of a particular item 21 in the electronic message 20 by being provided with inference data indicative of the inferred mental state of the authoring user 18 in connection with an "action" (e.g., creation) executed by the authoring user 18 with respect to the particular item 21. As will be further described, an action executed in connection with the particular item 21 may be in reference to any one of a number of acts that can be executed, at least in part, by the authoring user 18 including, for example, creating, modifying, deleting, relocating, extracting, and so forth in connection with the particular item 21. Note that unless indicated otherwise the term "particular item" as used herein merely refers to a specific item from, for example, a plurality of items that may be included in an electronic message 20 (see, for example, FIG. 2I).

After receiving the inference data indicative of the inferred mental state of the authoring user 18 from the authoring network device 10, a comparison of the inferred mental state of the authoring user 18 in connection with the particular item 21 and the inferred mental state of the receiving user 22 during or proximate to the presentation of the particular item 21 to the receiving user 22 may be made at the receiving network device 12. Note that the inferred mental state of the receiving user 22 with respect to the presentation of the particular item 21 may be determined based, at least in part, on observations of one or more physical characteristics of the receiving user 22 during or proximate to the presentation of the particular item 2. In any event, the comparison of the inferred mental states of the authoring user 18 and the receiving user 22 in connection with the particular item 21 may be made at the receiving network device 12 in order to determine the extent of congruity between the mental states of the authoring user 18 and the receiving user 22 with respect to the particular item 21. Alternatively, such comparison and congruity determination may be made at the third party network device 14. By making such comparisons, the receiving user 22 may be made aware as to whether the receiving user 22 properly understood the intent and meaning of the particular item 21 when the particular item 21 was presented to the receiving user 22.

For instance, in some cases if it is determined that there is very little congruence between the inferred mental state of the authoring user 18 and the inferred mental state of the receiving user 22 in connection with the particular item 21 then that may indicate that the receiving user 22 has misunderstood the intent and/or meaning of the particular item 21 when the particular item was presented to the receiving user 22. Alternatively, a determination of very little congruence between the inferred mental state of the authoring user 18 and inferred mental state of the receiving user 22 may, in some cases, actually indicate that the receiver user 22 did indeed understand the intent and meaning of the particular item 21 when the particular item 21 was presented to the receiving user 22. For example, if the authoring user 18 was in a sarcastic state of mind when creating the particular item 21 with the intent to anger the receiving user 22 then there may be very little congruence between the inferred mental state of the authoring user 18 and the inferred mental state of the receiving user 22 if the receiving user 22 properly understood the intent and meaning of the particular item 21.

In order to facilitate the receiving network device 12 (and/or the third party network device 14) in correctly processing and/or interpreting the inference data that may be provided by the authoring network device 10, the authoring network device 10, in various implementations, may acquire source identity data providing one or more identities of one or more sources (e.g., one or more sensors 48 that may be used to sense the physical characteristics of the authoring user 18) that is or are the basis for the inference data. The source identity data may then be associated with the particular item 21 in order to make the source identity data accessible or available to the receiving network device 12 (and/or the third party network device 14). In various implementations, by making available the source identity data, the receiving network device 12 (and/or the third party network device 14) may be facilitated in properly interpreting the inference data as provided by the authoring network device 10.

Returning to FIG. 1, the authoring network device 10 may communicate with the receiving network device 12, and in some instances, may also communicate with a third party network device 14 via a wireless and/or wired network 16. The authoring network device 10 may be any type of computing and/or communication device such as a server (e.g., network server), a personal computer (PC), a laptop computer, a personal digital assistant (PDA), a cellular telephone, a blackberry, and so forth. In some implementations, the authoring network device 10 may b a workstation and may interface or communicate directly with the authoring user 18. In some alternative implementations, however, in which the authoring network device 10 is, for example, a network server, the authoring network device 10 may communicate with the authoring user 18 through a local or remote network device 50 via, for example, the wireless and/or wired network 16.

The authoring network device 10 may include various components including, for example, an inference data acquisition module 30, a source identity acquisition module 31, an inference data association module 32, a source identity association module 33, an action module 34, a time module 36, one more email, instant message (IM), audio, and/or video applications 40, network communication interface 42, user interface 44, one or more sensors 48, and/or memory 49. In various other implementations, other components that are not depicted may also be included in the authoring network device 10. For instance, a presentation module for presenting to the authoring user 18 (e.g., via user interface 44) inference data that is indicative of an inferred mental state of the authoring user 18 in connection with a particular item 21 of an electronic message 20 may be included in the authoring network device 10. Other components may also be included in the authoring network device in various alternative implementations.

In various embodiments, the inference data acquisition module 30 may be configured to acquire inference data indicative of an inferred mental state of the authoring user 18 in connection with at least a particular item 21 of an electronic message 20. Unless indicated otherwise, the term "acquiring," as used herein, may refer to the determination, computation, or reception of, for example, data. In some instances, the acquisition of the inference data may involve initially observing or sensing one or more physical characteristics of the authoring user 18 using one or more sensors 48 that may include one or more integrated and/or external sensors.

As briefly described above, the authoring network device 10 may also include, among other things, a source identity acquisition module 31 (e.g., for acquiring source identity data providing one or more identities of one or more sources that is or are basis, at least in part, for the inference data acquired by the inference data acquisition module 30), an inference data association module 32 (e.g., for associating the inference data acquired by the inference data acquisition module 30 with the particular item 21), a source identity association module 33 (e.g., for associating the source identity data acquired by the source identity acquisition module 31 with the particular item 21), an action module 34 (e.g., for executing one or more actions in connection with the particular item 21), a time module 36 (e.g., for providing a time stamp or time window in connection with an action to be performed in connection with the particular item 21), one or more of email, instant messaging (IM), audio, and/or video applications 40, a network communication interface 42, a user interface 44, one or more sensors 48 (e.g., for sensing one or more physical characteristics of the authoring user 18), and/or memory 49 (e.g., which may be one or more memories for storing, for example, identities of one or more sources for the inference data acquired by the inference data acquisition module 30).

Figure 2A:
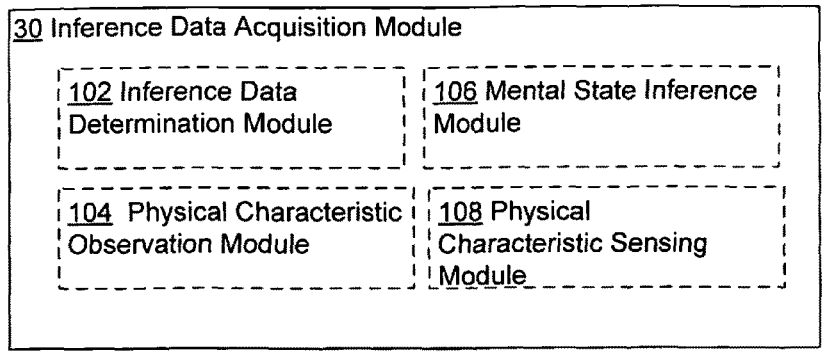
FIG. 2A shows another perspective of the inference data acquisition module 30 of FIG. 1.

Referring now to FIG. 2A showing particular implementations of the inference data acquisition module 30 of the authoring network device 10 of FIG. 1. As illustrated, the inference data acquisition module 30 may include one or more sub-modules including, for example, an inference data determination module 102, a physical characteristic observation module 104, a mental state inference module 106, and/or a physical characteristic sensing module 108.

In brief, the inference data determination module 102 may be particularly configured to, among other things, determine inference data indicative of an inferred mental state of an authoring user 18 in connection with a particular item 21 of an electronic message 20. In various implementations, such a determination may be based, at least in part, on one or more physical characteristics of the authoring user 18.

The physical characteristic observation module 104, on the other hand, may be configured to observe one or more physical characteristics of the authoring user 18 during or proximate to an action in connection with the particular item 21 and performed, at least in part, by the authoring user 18. In some implementations, the observance of the one or more physical characteristics of the authoring user 18 may be through a time window that corresponds to a time window through which the action in connection with the particular item 21 is performed. As will be further described, the action to be performed, which may be executed using the action module 34, may be any type of act that may be executed, at least in part, by the authoring user 18 in direct connection with the particular item 21. Examples of such acts may include, for example, creating, modifying, deleting, relocating, extracting, forwarding, storing, activating or deactivating, tagging, associating, categorizing, substituting, inserting, selecting, and so forth, in connection with the particular item 21.

Alternatively, the action to be performed may be other types of acts that may be performed by the authoring user 18 that may be indirectly connected to the particular item 21. For example, such indirect acts may include, for example, the movement of a user interface (UI) pointing device with respect to the particular item 21 being displayed on a user display, the specific movements of the authoring user's eyes (which may be detected using a gaze tracking device 151) during or proximate to the presentation of the particular item 21 through a user display, and the specific postures, gestures, and/or sounds (e.g., as detected though one or more sensors 48) made by the authoring user 18 in connection with the presentation to the authoring user 18 of the particular item 21 through the user interface 44.

The mental state inference module 106 of the inference data acquisition module 30 may be configured to infer a mental state for the authoring user 18 in connection with the particular item 21 based, at least in part, on one or more observed physical characteristics of the authoring user 18. In some implementations, the mental state inference module 106, based on the one or more observed physical characteristics of the authoring user 18, may infer a mental state for the authoring user 18 that indicates that the authoring user 18 was or is in at least one of state of anger, a state of distress, and/or a state of pain. In the same or different implementations, the mental state inference module 106 may infer, based on the one or more observed physical characteristics of the authoring user 18, a mental state for the authoring user 18 that indicates that the authoring user 18 was or is in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, and/or a state of acuity.

Finally, the physical characteristic sensing module 108 of the inference data acquisition module 30 may be configured to sense one or more physical characteristics of the authoring user 18 during or proximate to an action performed by the authoring user 18 and in direct or indirect connection with the particular item 21. Various physical characteristics of the authoring user 18 may be sensed using various sensors 48 in various alternative embodiments. For example, in some embodiments, the physical characteristic sensing module 108 employing the one or more sensors 48 may sense, during or proximate to an action in connection with the particular item 21 and performed, at least in party, by the authoring user, at least one of cerebral, cardiopulmonary, and/or systemic physiological characteristic associated with the authoring user 18.

For instance, in some implementations, the physical characteristic sensing module 108 may be configured to sense, during or proximate to an action in connection with the particular item 21 and performed, at least in part, by the authoring user 18, at least one characteristic connected with electrical activity of a brain associated with the authoring user 18. In the same or different implementations, the physical characteristic sensing module 108 may be configured to sense, during or proximate to the action in connection with the particular item 21 and performed, at least in part, by the authoring user 18, at least one of blood oxygen or blood volume changes of a brain associated with the authoring user 18. As will be further described, in the same or different implementations, other types of physical characteristics of the authoring user 18 may also be sensed by the physical characteristic sensing module 108.

Figure 2B:
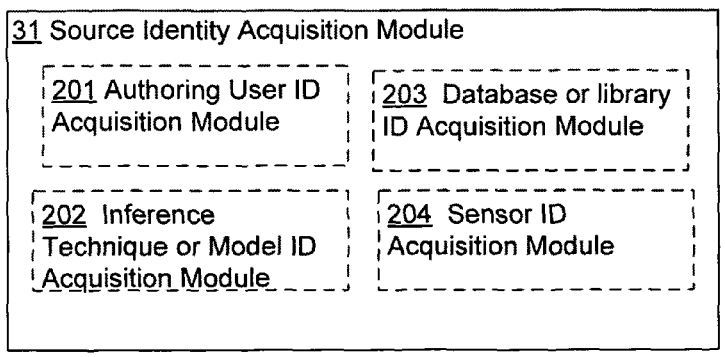
FIG. 2B shows another perspective of the source identity acquisition module 31 of FIG. 1.

In various embodiments, the authoring network device 10 may include a source identity acquisition module 31 that is configured to acquire source identity data that provides one or more identities of one or more sources that is or are the basis for the inference data obtained through the inference data acquisition module 30. As illustrated in FIG. 2B, the source identity acquisition module 31, in various implementations, may include one or more sub-modules including an authoring user identity (ID) acquisition module 201, an inference technique or model identity (ID) acquisition module 202, a database or library identity (ID) acquisition module 203, and/or a sensor identity (ID) acquisition module 204. These modules may perform one or more acquisition operations to acquire one or more identities of one or more sources for inference data acquired by the inference data acquisition module 30. For example, and as will be further described herein, the authoring user ID acquisition module 201 may be configured to acquire the identity of the authoring user 18. The inference technique or model ID acquisition module 202 in contrast may be configured to acquire the identity or identities of the inference technique and/or model that was used to derive or compute an inferred mental state of the authoring user 18 based on one or more sensed physical characteristics of the authoring user 18, while the database or library ID acquisition module 203 may be configured to acquire the identity or identities of a database and/or a library (e.g., storing physical characteristic patterns) that may be accessed by, for example, the mental state inference module 106 in order to determine an inferred mental state of the authoring user 18. Finally, the sensor identity ID acquisition module 204 may be configured to acquire the identity or identities of one or more sensors 48 used to sense one or more physical characteristics of the authoring user 18.

As indicated earlier, the authoring network device 10 may include an inference data association module 32 that may be configured to associate inference data (e.g., as acquired by the inference data acquisition module 30) indicative of the inferred mental state of the authoring user 18 with the particular item 21. Different approaches for associating the inference data with the particular item 21 may be employed in various alternative implementations.

For example, in some implementations, the inference data may be inserted into the particular item 21 or at a particular location (e.g., at a location proximate to the location where the particular item 21 is located) of the electronic message 20. In alternative embodiments, however, the inference data (i.e., inference data indicative of the inferred mental state of the authoring user 18) may be inserted anywhere in the electronic message 20, and association information (e.g., in the form of a link or name) that identifies the inference data may be provided to the particular item 21. In still other embodiments, the inference data may be inserted anywhere in the electronic message 20, and information (e.g., in the form of a link or name) that identifies the particular item 21 may be provided to the inference data. In still other embodiments, the inference data may be inserted into another electronic message (e.g., a different electronic message from electronic message 20 that includes the particular item 21) and the inference data and/or the particular item 21 may be provided with information that links or associates the inference data with the particular item 21. In yet other embodiments, the inference data may be stored or placed in, for example, a network server and the particular item 21 may be provided with a network link such as a hyperlink to the inference data. Other approaches may be employed in various other alternative embodiments for associating the inference data with the particular item 21.

Figure 2C:
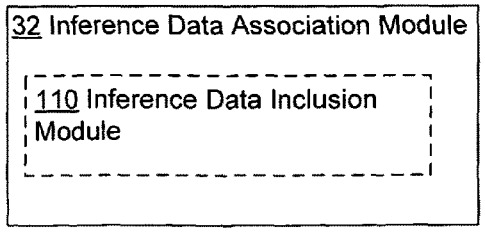
FIG. 2C shows another perspective of the inference data association module 32 of FIG. 1.

In some implementations, and as illustrated in FIG. 2C, the inference data association module 32 may further include an inference data inclusion module 110 for inserting various data including the inference data into the electronic message 20. For example, in some implementations, the inference data inclusion module 110 may be configured to include into the electronic message 20 a time stamp associated with the inference data indicative of the inferred mental state of the authoring user 18. In some implementations, the inference data inclusion module 110 may be configured to include into the electronic message 20, one or more indications of one or more actions performed by the authoring user 18 in connection with the particular item 21 (e.g., creation, modification, or deletion, for example, of the particular item 21 as performed, at least in party, by the authoring user 18). The inference data inclusion module 110 may also be further designed to include into the electronic message 20 various other types of data in various alternative implementations as will be further described herein.

Figure 2D:
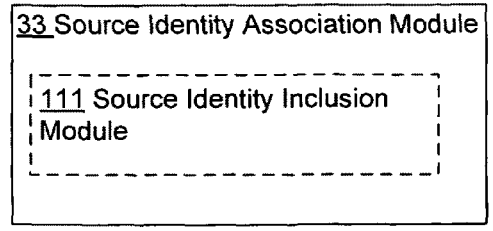
FIG. 2D shows another perspective of the source identity association module 33 of FIG. 1.

The authoring network device 10 may also include a source identity association module 33 for associating source identity data (e.g., as provided by the source identity acquisition module 31) with the particular item 21. As in the case of the inference data association module 32 described above, the source identity association module 33 may similarly employ different techniques in various alternative implementations for associating source identity data with the particular item 21 including, for example, inserting the source identity data into the particular item 21 or inserting the source identity data somewhere else in the electronic message 20. As illustrated in FIG. 2D, the source identity association module 33 may include, in various implementations, a source identity inclusion module 11 for including into the electronic message 20 the source identity data (e.g., source identity data providing one or more identities of one or more sources) as acquired by the source identity acquisition module 31.

Figure 2E:
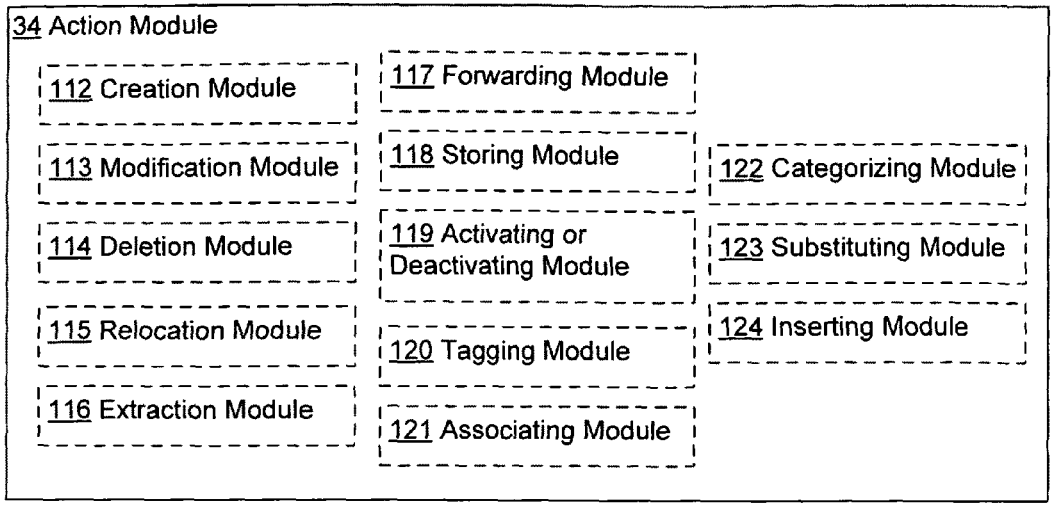
FIG. 2E shows another perspective of the action module 34 of FIG. 1.

The authoring network device 10, in various embodiments, may include an action module 34, which may be employed for executing one or more actions in connection with the particular item 21. In some implementations, the action module 34 may be embodied, at least in part, by one or more applications such as a text messaging application, an email application, an instant messaging (IM) application, an audio application, and/or a video application. As illustrated in FIG. 2E, the action module 34 may include, in various implementations, one or more sub-modules including, for example, a creation module 112, a modification module 113, a deletion module 114, a relocation module 115, an extraction module 116, a forwarding module 117, a storing module 118, an activating or deactivating module 119, a tagging module 120, an associating module 121, a categorizing module 122, a substituting module 123, and/or inserting module 124.

In some embodiments, the action module 34 may be configured to provide indications of actions (e.g., creating, modifying, deleting, relocating, extracting, and so forth) performed using the action module 34. Such indications may be in the form of, for example, an identifier (e.g., name) or symbolic representation of the actions performed.

In various implementations, the creation module 112 may be employed in order to, among other things, create a particular item 21. The modification module 113 may be employed in order to modify the particular item 21. Modification in this context may refer to a number of functions including, for example, changing the format of the particular item 21 (e.g., highlighting or bolding a word), adding or subtracting components into or from the particular item 21, and so forth. The deletion module 114 may be employed to, among other things, delete the particular item 21 from the electronic message 20. The relocation module 115 may be used in order to relocate the particular item 21 from, for example, a first location in the electronic message 20 to a second location in the electronic message 20.

The extraction module 116 may be used in order to extract the particular item 21 from the electronic message 20. In some implementations, extraction of the particular item 21 from the electronic message 20 may involve merely copying of the particular item 21 from the electronic message 20. The forwarding module 117 may be employed in order to, among other things, forward or send the particular item 21 to one or more recipients. The storing module 118 may be used in order to store or save the particular item 21. For instance, in some implementations, the storing module 118 may be used in order to store the particular item 21 into memory 49. The activating and deactivating module 119 may employed in order to, among other things, activate or deactivate the particular item 21. For example, if the electronic message 21 is an email message and the particular item 21 is some sort of video/animation image that can be activated or deactivated, then the activating and deactivating module 119 may be used in order to activate or deactivate the video/animation image.

The tagging module 120 may be employed in order to, among other things, tag or attach data or information to the particular item 21. For example, in some implementation, the tagging module 120 may be used in order to add some sort of indicator to the particular item 21 to, for example, flag the particular item 21. In contrast, the associating module 121 may be employed in order to associate the particular item 21 with, for example, another item. For instance, in some implementations, the associating module 121 may be used in order to associate the particular item 21 to another item by providing to the particular item 21 an identity or link (e.g., hyperlink) to the another item that may or may not be included in the electronic message 20.

The categorizing module 122 may be employed in order to categorize the particular item 21. For instance, the categorizing module 122 may be used to in order to associate the particular item 21 to a group of items that may or may not be included in the electronic message 20. Categorizing using the categorizing module 122 may also include labeling or tagging, for example, the particular item 21 in order to identify the particular item 21 as belonging to a particular group or class. The substituting module 123 may be employed in order to substitute or replace the particular item 21 in the electronic message 20. And finally, the inserting module 124 may be employed in order to insert the particular item 21 into the electronic message 20

Figure 2F:
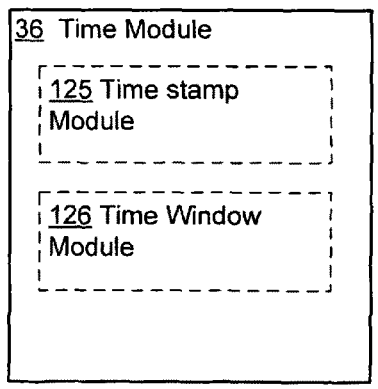
FIG. 2F shows another perspective of the time module 36 of FIG. 1.

Referring now to FIG. 2F showing particular implementations of the time module 36 of FIG. 1. The time module 36 may be configured to provide various time elements that may be used in order to acquire and associate inference data indicative of the inferred mental state of the authoring user 18 in connection with an action performed by the authoring user 18 with respect to the particular item 21. As depicted, the time module 36 may include one or more sub-modules including, for example, a time stamp module 125 (e.g., for providing one or more time stamps in connection with one or more actions executed with respect to the particular item 21) and/or a time window module 126 (e.g., for providing one or more time windows in connection with one or more actions executed with respect to the particular item 21). The functional roles of these sub-modules will be described in greater detail below in the context of the operations and processes to be described herein.

Figure 2G:
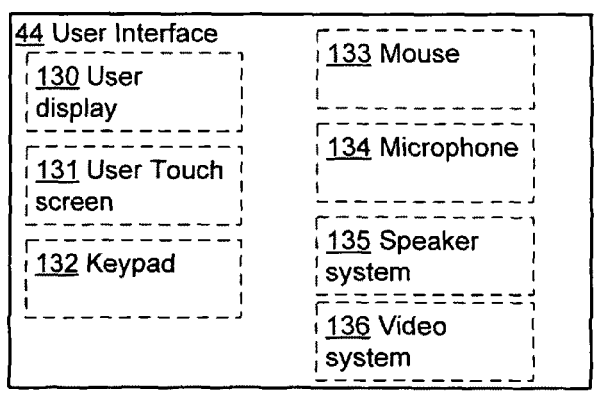
FIG. 2G shows another perspective of the user interface 44 of FIG. 1.

FIG. 2G shows particular implementations of the user interface 44 of the authoring network device 10 of FIG. 1. As illustrated, the user interfaced 44, which may actually be one or more user interfaces, may include one or more of a user display 130, a user touch screen 131, a keypad 132, a mouse 133, a microphone 134, a speaker system 135, and/or a video system 136.

As described previously the authoring network device 10 may include a memory 49, which may actually include one or more volatile and/or nonvolatile memories (e.g., SRAM, DRAM, flash memory, hard or disk drives, and so forth). The memory 49 may be employed in various implementations to store identities of one or more sources that is or are the basis for inference data (e.g., indicative of the inferred mental state of the authoring user 18 in connection with the particular item 21) acquired by, for example, the inference data acquisition module 30. In some implementations, the memory 49 may also be used in order to store a database or library of physical characteristic patterns used to derive the inferred mental states of the authoring user 18. Other data and information may also be stored in the memory in various alternative embodiments.

Turning now to FIG. 2H showing particular implementations of the one or more sensors 48 of FIG. 1. The one or more sensors 48, which may be one or more integrated and/or external sensors of the authoring network device 10, may be employed in order to sense one or more physical characteristics of the authoring user 18 during or proximate to an action performed by the authoring user 18 in connection with the particular item 21. For example, and as will be further described, in some implementations, the one or more sensors 48 may be designed to sense one or more of cerebral, cardiopulmonary, and/or systemic physiological characteristics of the authoring user 18 during or proximate to action performed by the authoring user 18 in connection with the particular item 21. In various embodiments, the one or more sensors 48 may include a functional magnetic resonance imaging (fMRI) device 140, a functional near-infrared imaging (fNIR) device 141, an electroencephalography (EEG) device 142, a magnetoencephalography (MEG) device 143, a galvanic skin sensor device 144, a heart rate sensor device 145, a blood pressure sensor device 146, a respiration sensor device 147, a facial expression sensor device 148, a skin characteristic sensor device 149, a voice response device 150, a gaze tracking device 151, and/or an iris response device 152.

In some implementations, the one or more sensors 48 may include one or more sensors that are capable of measuring various brain characteristics of the authoring user 18 during or proximate to an action performed by the authoring user 18 in connection with the particular item 21. These sensors may include, for example, a functional magnetic resonance imaging (fMRI) device 140, a functional near-infrared imaging (fNIR) device 141, an electroencephalography (EEG) device 142, and/or a magnetoencephalography (MEG) device 143. In some implementations, an fMRI device 140 and/or an fNIR device 141 may be employed in order to measure certain physiological characteristics of the brain of an authoring user 18 including, for example, blood oxygen or blood volume changes of the brain of the authoring user 18. In the same or different implementations, an EEG device 142 may be used to sense and measure the electrical activities of the brain of the authoring user 18 while an MEG device 143 may be employed in order to sense and measure the magnetic fields produced by electrical activities of the brain of the authoring user 18.

Other type of devices may also be employed in order to measure the brain activities of the authoring user 18 during or proximate to an action performed by the authoring user 18 in connection with the particular item 21. Such devices may include, for example, a positron emission topography device. In various embodiments, the data collected from these sensor devices may be further processed (e.g., by the mental state inference module 108) in order to determine an "inferred" mental state of the authoring user 18 during or proximate to an action performed by the authoring user 18 in connection with the particular item 21.

As will be further described, in some implementations, other types of sensors such as those that measure other types of physical characteristics may be employed as sensor[s] 48 (e.g., a galvanic skin sensor device 144, a heart rate sensor device 145, a blood pressure sensor device 146, a respiration sensor device 147, a facial expression sensor device 148, a skin characteristic sensor device 149, a voice response device 150, a gaze tracking device 151, and/or an iris response device 152) in order to obtain data that may be used (e.g., by the mental state inference module 108) to determine the inferred mental state or states of the authoring user 18 during or proximate to an action performed by the authoring user 18 in connection with the particular item 21.

Figure 2I:
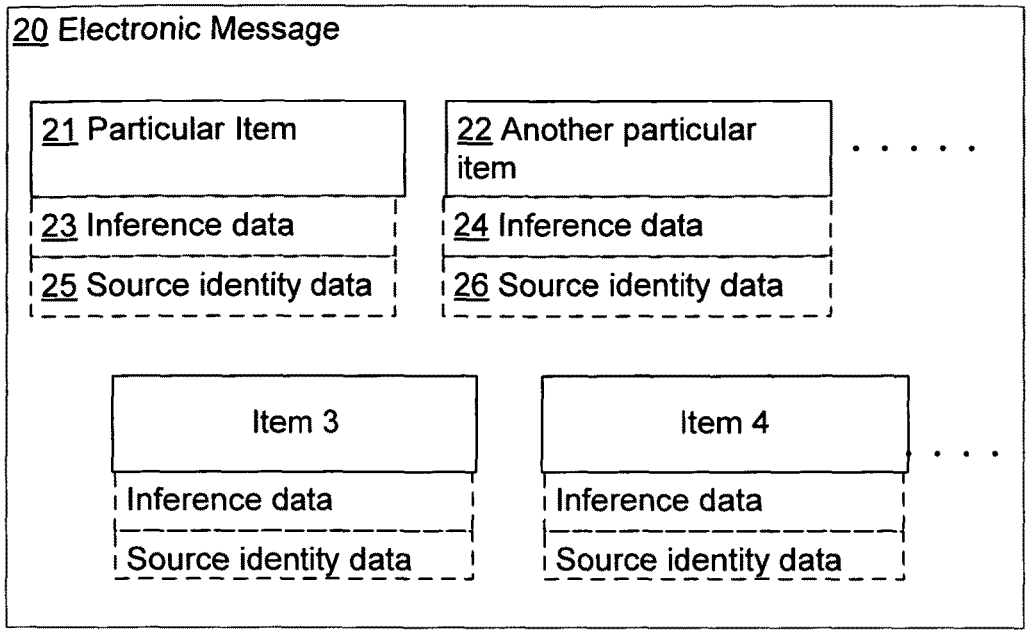
FIG. 2I shows another perspective of the electronic message 20 of FIG. 1.

As previously indicated, the one or more sensors 48 may be used in order to observe one or more physical characteristics of the authoring user 18 in connection with an action (e.g., creation, modification, or deletion of the particular item 21) performed by the authoring user 18 with respect to the particular item 21. For example, the one or more sensors 48 may be used to sense one or more physical characteristics of the authoring user 18 during or proximate to a modification (e.g., action) by the authoring user 18 of the particular item 21. In some implementations, this may mean selectively "switching on" or activating the one or more sensors 48 only during or proximate to the modification (e.g., action) of the particular item 21 of the electronic message 20 in order to observe the one or more physical characteristics of the authoring user 18. In contrast, the one or more sensors 48 may be switched off or deactivated during or proximate to other actions that may be performed by the authoring user 18 in connection with other items (e.g., another particular item 22, item 3, item 4, and so forth of the electronic message as illustrated in FIG. 2I) of the electronic message 20. In alternative implementations, however, the one or more sensors 48 may be continuously operated (e.g., not switched off and on as described above) in which case only data provided by the one or more sensors 48 during or proximate to the modification of the particular item 21 may be collected or used (e.g., by the mental state inference module 106). Note that the term "proximate" as used herein may refer to, partly during, immediately subsequent, or immediately preceding the action to be taken (e.g., modification) with respect to the particular item 18.

Data obtained from observations made using one or more such sensors 48 may be collected by, for example, the inference data acquisition module 30 in order to acquire inference data indicative of an inferred mental state of the authoring user 18 in connection with, for example, the particular item 21. In some embodiments, raw data collected from the one or more sensors 48 may be further processed by the mental state inference module 106 in order to provide an inferred mental state for the authoring user 18 in connection with the particular item 21. Thus, the inference data indicative of the inferred mental state of the authoring user 18 acquired by the inference data acquisition module 30 may be in the form of raw data collected from the one or more sensors 48, or in the form of processed data that directly infers a mental state of the authoring user 18. As briefly described earlier, in addition to being associated with or connected to the particular item 21, inference data (e.g., as acquired by the inference data acquisition module 30) may be connected or associated with a particular action related to the particular item 21 and performed by the authoring user 18. Such an action may include, for example, any one or more of creation, modification, deletion, relocation, extraction, forwarding, storing, activating or deactivating, tagging, associating, categorizing, substituting, inserting, and so forth, of the particular item 21 by the authoring user 18.

FIG. 2I shows particular implementations of the electronic message 20 of FIG. 1. The electronic message 20 may be any type of message that can be electronically communicated including, for example, an email message, a text message, an instant message (IM), an audio message, a video message, and so forth. As shown the electronic message 20 may include multiple items, which are depicted as a particular item 21, another particular item 22, item 3, item 4, and so forth. An "item" may be any part or portion of the electronic message 20. For example, if the electronic message 20 is an email message, an item could be a passage, a sentence, a paragraph, a word, a letter, a number, a symbol (e.g., icon), an image, the format of text (e.g., bold, highlighting, font size, and so forth), In various embodiments, the electronic message 20 may include inference data indicative of an inferred mental state of the authoring user 18 in connection with the particular item 21, which is depicted as inference data 23 in FIG. 2I. The electronic message 20 may also include source identity data 25 providing one or more identities of one or more sources that is or are the basis for the inference data 23 indicative of the inferred mental state of the authoring user 18. In some implementations, inference data 23 may only be connected or associated with particular item 21 without being associated with the other items (e.g., another particular item 22, item 3, item 4, and so forth) of the electronic message 20. More particularly, each inference data/source identity data pair (e.g., inference data 23/source identity data 25, inference data 24/source identity data 26, and so forth as depicted in FIG. 2I) in various implementations may be associated with corresponding items (e.g., particular item 21, another particular item 22, and so forth). For these implementations, each inference data (e.g., inference data 23, inference data 24, and so forth) may indicate an inferred mental state of the authoring user 18 with respect to their associated item (e.g., particular item 21, another particular item 22, and so forth) while each source identity data (e.g., source identity data 25, source identity data 26, and so forth) may provide one or more identities of one or more sources that is or are the basis for the corresponding inference data (e.g., inference data 23, inference data 24, and so forth).

An inference data/source identity data pair may be associated with their associated item in any number of different ways in various alternative implementations. For instance, in various implementations particular item 21 may be associated with inference data 23 and source identity data 25 by locating or placing the inference data 23 and the source identity data 25 at specified locations in the electronic message 20. In some implementations, this may mean locating the inference data 23 and the source identity data 25 within the particular item 21 or proximate (e.g., nearby) to the location of the particular item 21 in the electronic message 20. Similarly, the other inference data (e.g., inference data 24) and the other source identity data (e.g., source identity data 26) included in the electronic message 20 may also be associated with their corresponding item (e.g., another particular item 22) by locating them at specified locations in the electronic message 20. In other alternative approaches, an inference data/source identity data pair (e.g., inference data 23/source identity data 25) may be located anywhere (e.g., randomly) in the electronic message 20 and may be associated with a corresponding item (e.g., particular item 21) by providing to the inference data/source identity data pair (e.g., inference data 23/source identity data 25) an identifier that identifies the corresponding item (e.g., particular item 21). In other implementations, however, rather than providing an identifier for the corresponding item (e.g., particular item 21) to the inference data/source identity data pair (e.g., inference data 23/source identity data 25), an identifier or identifiers of the inference data/source identity data pair may be provided to the corresponding item.

In some alternative implementations, an inference data/source identity data pair may be associated with more than one item. For instance, in some implementations, the inference data 23, which again is inference data indicative of an inferred mental state of the authoring user 18, may be connected to both the particular item 21 and another particular item 22. Note that although inference data 23 and the source identity data 25 are depicted as being located adjacent or in the vicinity of the particular item 21 in the example electronic message 20 of FIG. 2I, in alternative implementations, the inference data 23 and/or the source identity data 25 may be located elsewhere in the electronic message 20 as described above. In yet other implementations, inference data 23 and/or source identity data 25 may be placed in another electronic message (not depicted) instead of in the electronic message 20. In some implementations, inference data 23 and/or source identity data 25 may be included in the electronic message 20 in the form of metadata.

Figure 2J:
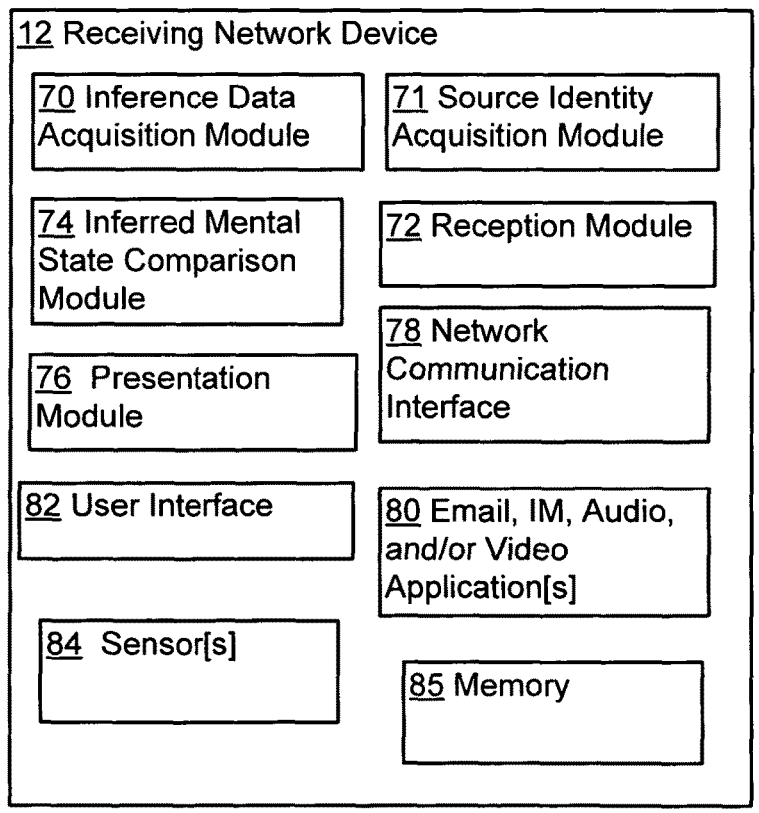
FIG. 2J shows another perspective of the receiving network device 12 of FIG. 1.

Turning now to FIG. 2J, which shows the receiving network device 12 of FIG. 1 in accordance with various implementations. More particularly, FIG. 2J depicts the receiving network device 12 having some of the same components as the authoring network device 10 depicted in FIG. 1. For instance, and similar to the authoring network device 10, the receiving network device 12 may include an inference data acquisition module 70, source identity acquisition module 71, a network communication interface 78, one or more of email, IM, audio, and/or video applications 80, user interface 82, one or more sensors 84, and memory 85. As will be explained, with certain exceptions, each of these components may include the same sub-components or sub-modules as those included in their counterparts in the authoring network device 10. For example, the one or more sensors 84 may include (see FIG. 2K) one or more of an fMRI device 140', an fNIR device 141', an EEG device 142', an MEG device 143', and so forth, while the inference data acquisition module 70 may include (see FIG. 2M) an inference data determination module 102', an mental state inference module 106', an physical characteristic observation module 104', and/or a physical characteristic sensing module 108' similar to their counterparts in the authoring network device 10. Further, these components may serve the same or similar functions as those functions performed by their counterparts in the authoring networking device 10.

Figure 2K:
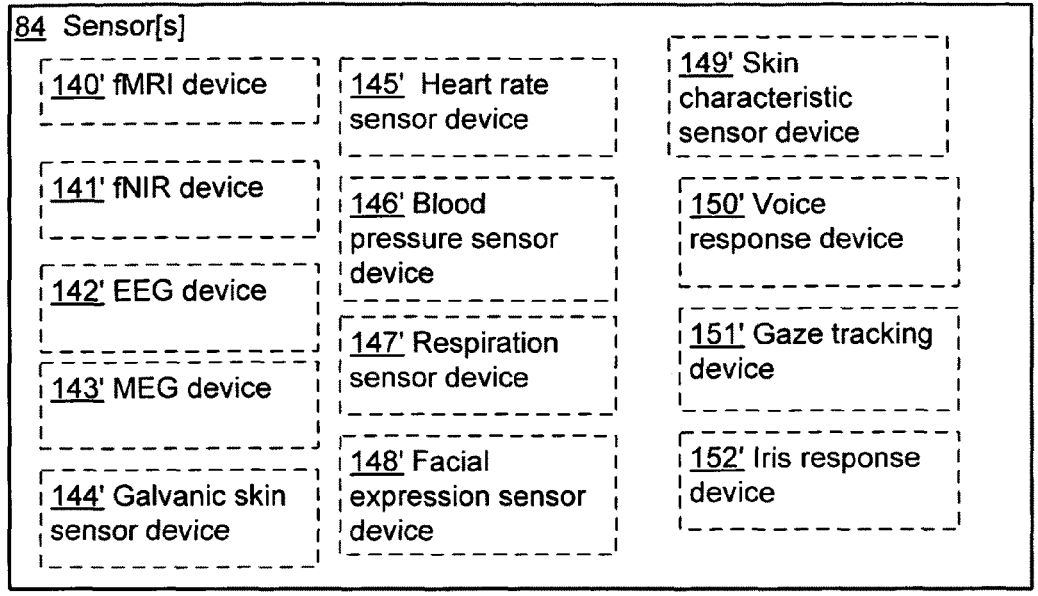
FIG. 2K shows another perspective of the one or more sensors 84 of the receiving network device 12 of FIG. 2J.
Figure 2L:
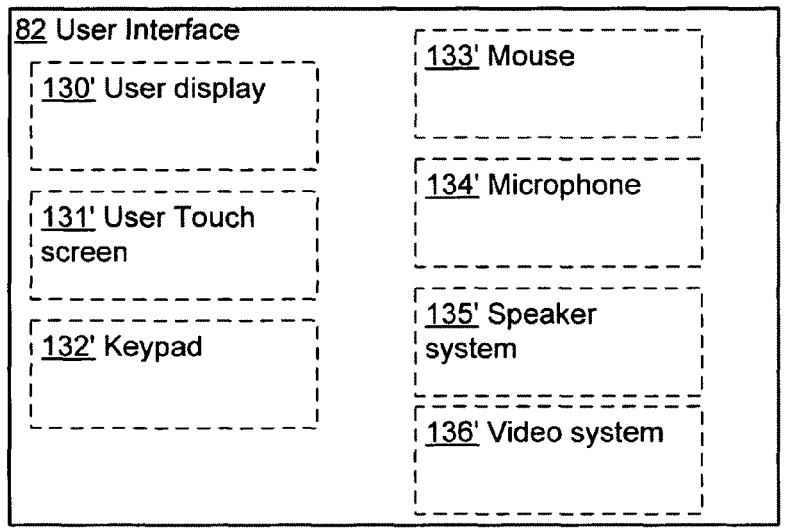
FIG. 2L shows another perspective of the user interface 82 of the receiving network device 12 of FIG. 2J.

Similarly, the user interface 82 of the receiving network device 12 as illustrated in FIG. 2L may include the same type of components as included in the user interface 44 of the authoring network device 10. For instance, in various embodiments, user interface 82 may include a user display 130', a user touch screen 131', a keypad 132', a mouse 133', a microphone 134', a speaker system 135', and/or a video system 136'.

In addition to the above described components, the receiving network device 12 may also include a reception module 72, an inferred mental state comparison module 74, and a presentation module 76. In brief, the reception module 72 may be configured to receive, among other things, a particular item 21 of an electronic message 20, inference data indicative of the inferred mental state of an authoring user 18 in connection with the particular item 21 (which may be included in the electronic message 21 or in another electronic message), source identity data providing one or more identities of one or more sources that is or are basis for the inference data, a time stamp associated with the particular item 21, and/or an indication of an action performed by the authoring user 18 in connection with the particular item 21. The inferred mental state comparison module 74 may be configured to, for example, compare the inferred mental state of the receiving user 22 (e.g., in connection with the presentation of the particular item 21 to the receiving user 22) with the inferred mental state of the authoring user 18 (e.g., in connection with action performed with respect to the particular item 21).

Note that the inference data (e.g., inference data 23) indicative of the inferred mental state of the authoring user 18 that is received by the reception module 72 may be in at least one of two different forms. In the first form, the received inference data may be sensor provided data (e.g., "raw" data) of one or more physical characteristics of the authoring user 18. In some implementations, such data may be further processed by the receiving network device 12 in order to derive one or more inferred mental states of the authoring user 18. In the second form, the received inference data may be "processed" data (e.g., as processed by the authoring network device 10 via, for example, the mental state inference module 106) that may directly indicate or identify an inferred mental state of the authoring user 18 in connection with an action performed by the authoring user 18 with respect to the particular item 21.

Referring back to FIG. 2J, the receiving network device 12 may further include an inferred mental state comparison module 74. The inferred mental state comparison module 74 may be employed in order to compare an inferred mental state of the authoring user 18 with an inferred mental state of the receiving user 22 in connection with a particular item 21 of an electronic message 20. Such a comparison may be used in order to determine the congruity between the inferred mental state of the authoring user 18 and the inferred mental state of the receiving user 22 in connection with the particular item 21. The results of the comparison and congruence determination may then be presented to the receiving user 22 via the presentation module 76. Note that in various implementations the inferred mental state of the receiving user 22 may be obtained, at least in part, by using one or more sensors 84 in order to observe one or more physical characteristics of the receiving user 22 during or proximate to the presentation of the particular item 21.

In order to derive an inferred mental state of the receiving user 22 during or proximate to the presentation. (e.g., display) of the particular item 21 to the receiving user 22, one or more physical characteristics of the receiving user 22 may be observed during or proximate to the presentation of the particular item 21 to the receiving user 22 using the one or more sensors 84. Referring to FIG. 2K which shows the one or more sensors 84 of the receiving network device 12 in accordance with various embodiments. The one or more sensors 80 may include a functional magnetic resonance imaging (fMRI) device 140', a functional near-infrared imaging (fNIR) device 141', an electroencephalography (EEG) device 142', a magnetoencephalography (MEG) device 143', a galvanic skin sensor device 144', a heart rate sensor device 145', a blood pressure sensor device 146', a respiration sensor device 147', a facial expression sensor device 148', a skin characteristic sensor device 149', a voice response device 150', a gaze tracking device 151', and/or an iris response device 152').

Figure 2M:
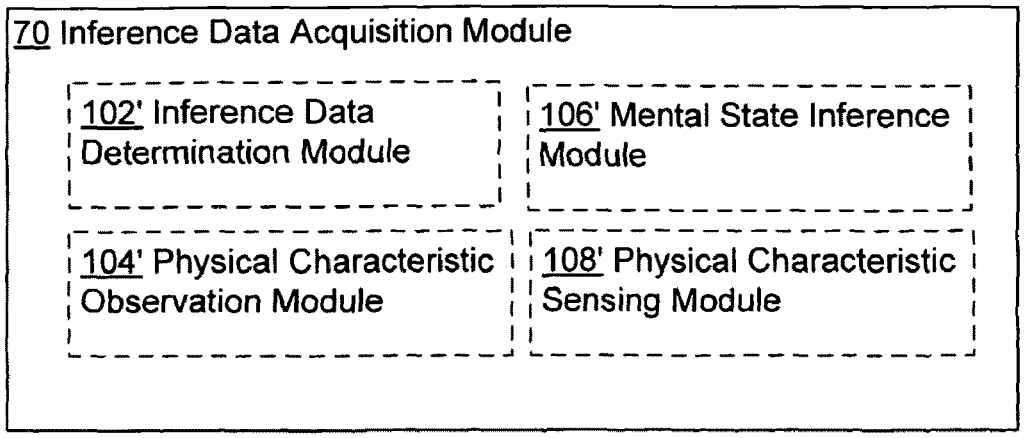
FIG. 2M shows another perspective of the inference data acquisition module 70 of the receiving network device 12 of FIG. 2J.

FIG. 2M illustrates the inference data acquisition module 70 of the receiving network device 12 in accordance with various embodiments. As illustrated, the acquisition module 70 may include one or more sub-modules including an inference data determination module 102', a physical characteristic observation module 104', a mental state inference module 106', and/or physical characteristic sensing module 108', similar to the sub-modules that may be included in the inference data acquisition module 30 of the authoring network device 10. These sub-modules may perform functions similar to the functions performed by their counterparts in the inference data acquisition module 30 of the authoring network device 10. For example, the inference data determination module 102' may be employed in order to determine inference data indicative of an inferred mental state of the receiving user 22 based on one or more physical characteristics of the receiving user 22. The physical characteristic observation module 104' may be employed in order to observe the one or more physical characteristics of the receiving user 22. The mental state inference module 106' may be employed in order to infer a mental state for the receiving user 22 in connection with the particular item 21. And the physical characteristic sensing module 108' may be employed in order to sense one or more physical characteristics of the receiving user 22 in connection with, for example, the presentation to the receiving user 22 of the particular item 21.

In various embodiments, the inference modules 106/106' of the acquisition modules 30/70 of the authoring network device 10 and the receiving network device 12 may employ various techniques or models in order to infer one or more mental states from observed physical characteristics of a subject (e.g., authoring user 18 or receiving user 22). In some implementations, this may mean associating particular physical characteristics or patterns of physical characteristics of a subject to one or more mental states (i.e., inferred mental states).

For example, if the one or more sensors 48 depicted in FIG. 1 include an fMRI device 140, then the fMRI device 140 may be used in order to scan the brain of the subject (e.g., authoring user 18) during or proximate to an action (e.g., creation, modification, deletion, and so forth) performed by the authoring user 18 in connection with the particular item 21. As a result of the functional magnetic resonance imaging (fMRI) procedure performed using the fMRI device 140, a profile or a pattern of brain activities (e.g., blood oxygen and/or blood volume changes of the brain) of the authoring user 18 during or proximate to the execution of the action in connection with the particular item 21 may be obtained. The determined "brain activity pattern" may then be compared to brain activity patterns, which are physical characteristic patterns, that may have been previously recorded and stored in a database or library (each of the stored brain activity patterns being linked with, for example, corresponding mental states). In some implementations, such a database or library may include information relative to the subject (e.g., in this case, the authoring user 18) including, for example, log of raw sensor data or data of mappings between sensor data and known or inferred mental states that may be used in order to "calibrate" data received from the one or more sensors 48. Alternatively, a model may be employed that associates, for example, different patterns of brain activities with different mental states. Such a model may be used in conjunction with data received from other types of sensors (e.g., those types of sensors that do not measure brain activities) in order to associate, for example, a pattern of brain activity with one or more mental states.

Such a database or library may contain numerous brain activity patterns that may have been obtained by sampling a number of people from the general population, having, for example, similar metrics (e.g., age, gender, race, education, and so forth) as the subject (e.g., authoring user 18). By asking each person what they felt (e.g., mental state) at the time when their brain activity pattern was recorded, or by using, for example, some other established testing procedures, each brain activity pattern stored in the library or database may be associated with one or more mental states. As a result, by comparing the determined brain activity pattern of the authoring user 18 with the brain activity patterns (e.g., physical characteristic patterns) stored in the database or library, one or more mental states may be inferred from the observed physical characteristics of the authoring user 18.

Figure 2N:
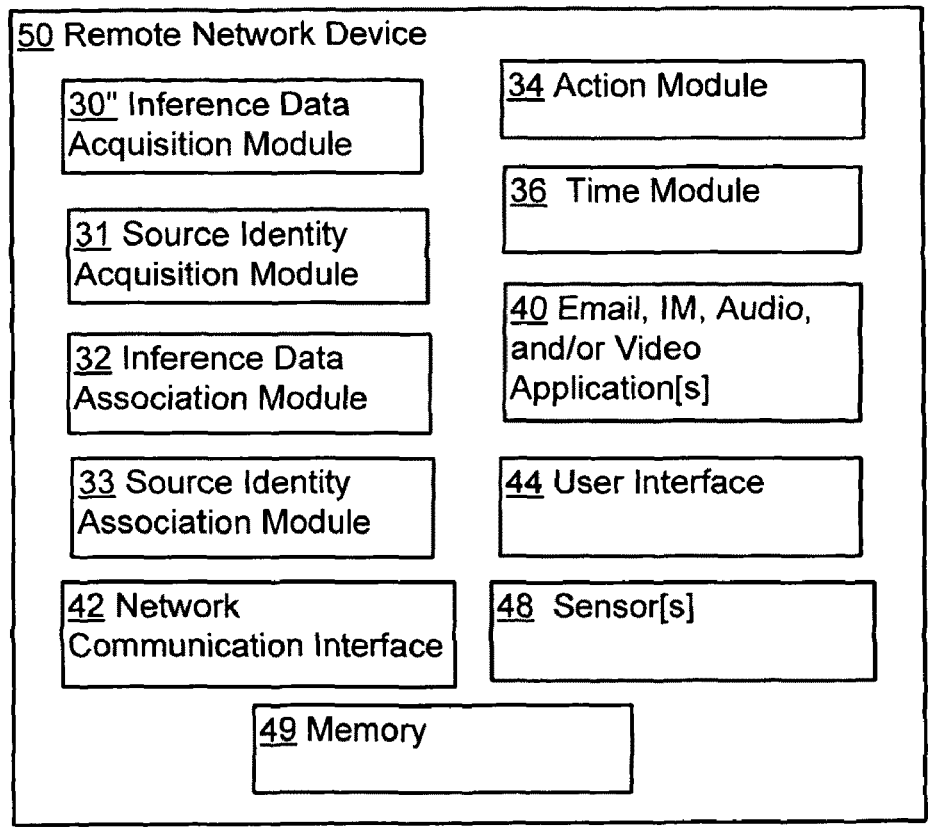
FIG. 2N shows another perspective of the remote network device 50 of FIG. 1.

Referring to FIG. 2N, which illustrates the remote network device 50 of FIG. 1, in accordance with various embodiments. As briefly described earlier, a remote network device 50 may be employed in some circumstances when, for example, the authoring network device 10 is a network server and a remote network device 50 may be needed in order to collect data with respect to the particular item 21 and/or inference data indicative of the inferred mental state of the authoring user 18 in connection with the particular item 21. As depicted, the remote network devices 50 may include components similar to those components depicted in the authoring network device 10 of FIG. 1. For example, and as illustrated, the remote network device 50 may include an inference data acquisition module 30", a source identity acquisition module 31". an inference data association module 32", a source identity association module 33, an action module 34", a time module 36", one or more email, IM, audio, and/or video applications 40", a network communication interface 42", a user interface 44", and one or more sensors 48". These components may further include sub-components and/or sub-modules similar to the sub-components and sub-modules previously depicted for the authoring network device 10.

Referring back to FIG. 1, the various components (e.g., inference data acquisition module 30, source identity acquisition module 31, inference data association module 32, source identity association module 33, action module 34, time module 36, and so forth) along with their sub-components or sub-modules included with the authoring network device 10 may be embodied by hardware, software and/or firmware. For example, in some implementations the inference data acquisition module 30, the source identity acquisition module 31, the inference data association module 32, the source identity association module 33, the action module 34, and the time module 36 may be implemented with a processor (e.g., microprocessor, controller, and so forth) executing computer readable instructions (e.g., computer program product) stored in a storage medium (e.g., volatile or nonvolatile memory) such as a signal-bearing medium. Alternatively, hardware such as application specific integrated circuit (ASIC) may be employed in order to implement such modules in some alternative implementations.

Figure 3:
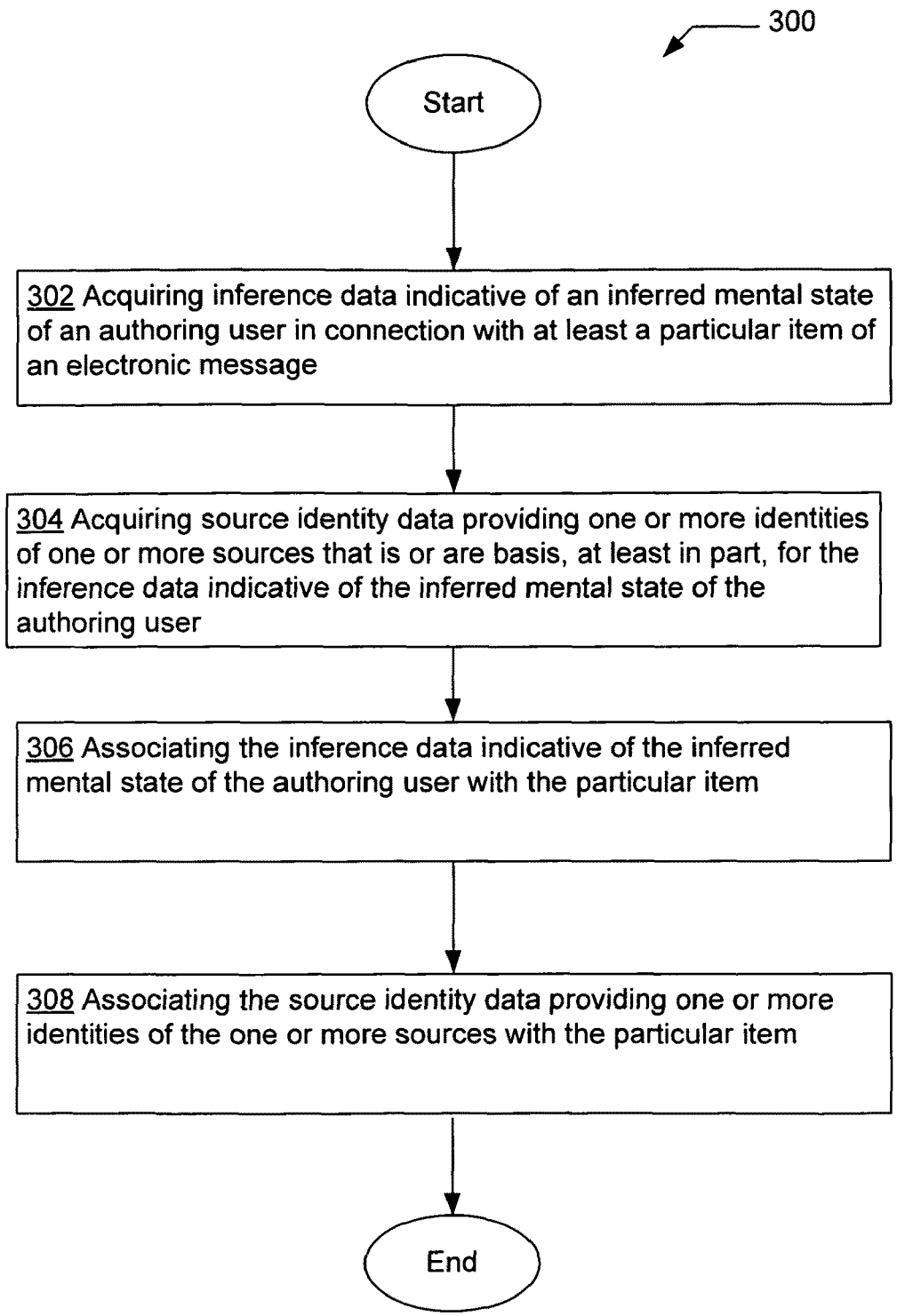
FIG. 3 is a high-level logic flowchart of a process.

FIG. 3 illustrates an operational flow 300 representing example operations related to acquisition and association of inference data indicative of an inferred mental state of an authoring user in connection with at least a particular item of an electronic message. In various embodiments, the operational flow 300 may be executed by, for example, the authoring network device 10 or the remote network device 50 of FIG. 1. That is, although operational flow 300 and the subsequent processes and operations (e.g., see FIGS. 4 to 12C) will be generally described in the context of the authoring network device 10 executing such processes and operations, these processes and operations may also be executed via the remote network device 50 in various alternative implementations.

In FIG. 3 and in the following figures that include various examples of operational flows, discussions and explanations may be provided with respect to the above-described exemplary environment of FIG. 1, and/or with respect to other examples (e.g., as provided in FIGS. 2A-2N) and contexts. However, it should be understood that the operational flows may be executed in a number of other environments and contexts, and/or in modified versions of FIGS. 1 and 2A-2N. Also, although the various operational flows are presented in the sequence(s) illustrated, it should be understood that the various operations may be performed in other orders than those which are illustrated, or may be performed concurrently.

Further, in FIG. 3 and in following figures, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to an inference data acquisition operation 302, where acquiring inference data indicative of an inferred mental state of an authoring user in connection with at least a particular item of an electronic message may be performed by, for example, the authoring network device 10 of FIG. 1. For instance, the inference data acquisition module 30 of the authoring network device 10 acquiring (e.g., by receiving from a remote network device 50 and/or by determining or deriving locally at the authoring network device 10) inference data indicative of an inferred mental state (e.g., state of happiness, state of anger, state of distress, and so forth) an authoring user 18 in connection with at least a particular item 21 of an electronic message 20.

The inference data indicative of the inferred mental state of the authoring user 18 to be acquired, which may be referred herein as simply "inference data," may be in the form of raw or unprocessed data collected from, for example, one or more sensors 48 (e.g., an fMRI device 140, an fNIR device 141, an EEG device 142, and/or an MEG device 143), which when processed, may provide data that identifies one or more inferred mental states (e.g., state of frustration, state of trust, state of fear, and so forth) of the authoring user 18. Alternatively, the inference data to be acquired may be in the form of data (e.g., as provided by a mental state inference module 106 of the acquisition module 30 as depicted in FIG. 2A) that may directly identify one or more inferred mental states of the authoring user 18.

Operational flow 300 may further include a source identity acquisition operation 304 where acquiring source identity data providing one or more identities of one or more sources that is or are basis, at least in part, for the inference data indicative of the inferred mental state of the authoring user may be performed by, for example, the authoring network device 10 of FIG. 1. For instance, the source identity acquisition module 31 of the authoring network device 10 acquiring (e.g., by receiving or retrieving) source identity data providing one or more identities (e.g., the type or specific model number of the one or more sensors 48) of one or more sources (e.g., fMRI device 140, fNIR device 141, EEG device 142, MEG device 143, and so forth) that is or are the basis, at least in part, for the inference data indicative of the inferred mental state (e.g., state of happiness, state of anger, state of frustration, and so forth) of the authoring user 10.

The operational flow 300 may then move to an inference data association operation 306 where associating the inference data indicative of the inferred mental state of the authoring user with the particular item may be executed by, for example, the authoring network device 10. For example, the inference data association module 32 of the authoring network device 10 associating data (e.g., sensor data as provided by one or more sensors 48 and/or inference data as provided by a mental state inference module 106) indicative of the inferred mental state (e.g., state of happiness, state of anger, state of distress, and so forth) of the authoring user 18 with the particular item 21. In various alternative implementations, the associating of the inference data indicative of the inferred mental state of the authoring user 18 with the particular item 21 may involve linking the inference data to the particular item 21, including the inference data into the particular item 21 or the electronic message 20, or some other way of linking the inference data to the particular item 21.

The operation flow 300 may also include a source identity association operation 308 in which associating the source identity data providing one or more identities of the one or more sources with the particular item may be executed by, for example, the authoring network device 10. For instance, and more particularly, the source identity association module 33 of the authoring network device 10 associating the source identity data providing one or more identities (e.g., name or names) of the one or more sources (e.g., inference technique and/or model used to infer a mental state for the authoring user 18) with the particular item 21.

A number of approaches may be employed in order to associate the source identity data with the particular item 21 in various alternative implementations. For example, various implementations, the associating of the source identity data with the particular item 21 may involve linking the source identity data with the particular item 21, including the source identity data into the particular item 21 or into the electronic message 20, or some other way of associating or relating the source identity data to the particular item 21.

Figure 4:
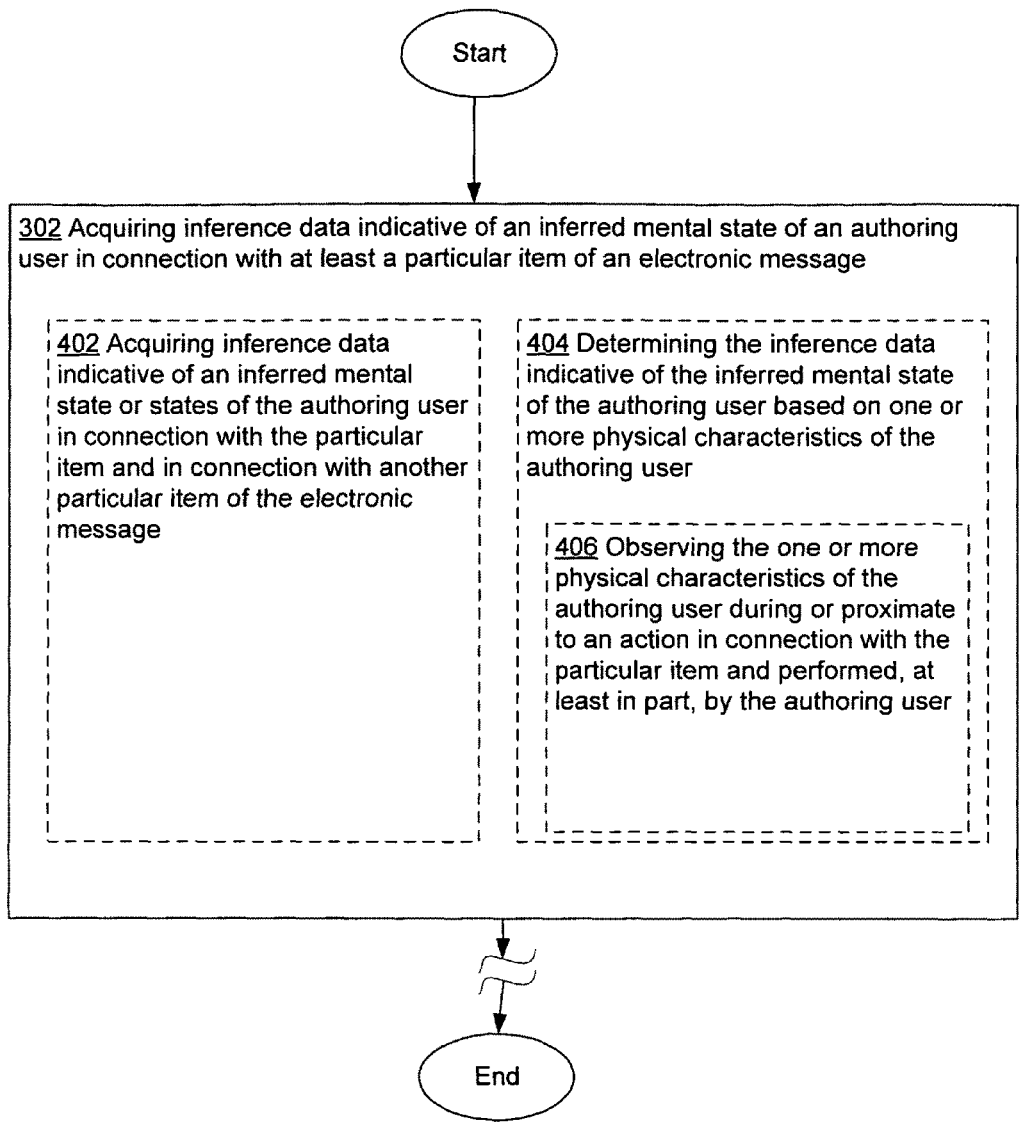
FIG. 4 is a high-level logic flowchart of a process depicting alternate implementations of the inference data acquisition operation 302 of FIG. 3.

In various embodiments, the inference data acquisition operation 302 of FIG. 3 may include one or more additional operations as illustrated in, for instance, FIG. 4. For example, in some embodiments, the acquisition operation 302 may include an operation 402 for acquiring inference data indicative of an inferred mental state or states of the authoring user in connection with the particular item and in connection with another particular item of the electronic message. That is, inference data indicative of an inferred mental state or states of the authoring user 18 that may be connected to more than one item of an electronic message may be acquired in various alternative embodiments. For instance, in some implementations, the inference data acquisition module 30 of the authoring network device 10 acquiring (e.g., as directly or indirectly provided by one or more sensors 48 including an fMRI device 140, an fNIR device 141, an EEG device 142, and/or MEG device 143) inference data indicative of an inferred mental state or states (e.g., state of anger, state of distress, and/or state of pain) of the authoring user 18 in connection with the particular item 21 and in connection with another particular item 22 of the electronic message 20.

In some embodiments, the acquisition operation 302 may include a determination operation 404 for determining the inference data indicative of the inferred mental state of the authoring user based on one or more physical characteristics of the authoring user. For instance, in some implementations, the inference data determination module 102 (see FIG. 2A) of the authoring network device 10 determining the inference data indicative of the inferred mental state (e.g., a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity) of the authoring user 19 based on one or more physical characteristics (e.g., as sensed by one or more sensors including, for example, a galvanic skin sensor device 144, a heart rate sensor device 145, and so forth) of the authoring user 18.

In some embodiments the determination operation 404 may include one or more additional operations. For example, in some embodiments, the determination operation 404 may include an observation operation 406 for observing the one or more physical characteristics of the authoring user during or proximate to an action in connection with the particular item and performed, at least in part, by the authoring user. For instance, in some implementation, the physical characteristic observation module 104 (see FIG. 2A) of the authoring network device 10 observing (e.g. via one or more sensors 48 including, for example, blood pressure sensor device 146, respiration sensor device 147, facial expression sensor device 148, and so forth) the one or more physical characteristics (e.g., blood pressure, respiration, facial expressions, and so forth) of the authoring user 18 during or proximate to an action (e.g., any one or more of creating, modifying, deleting, relocating, and so forth, of the particular item 21) in connection with the particular item 21 and performed, at least in part, by the authoring user 18.

Figure 5A:
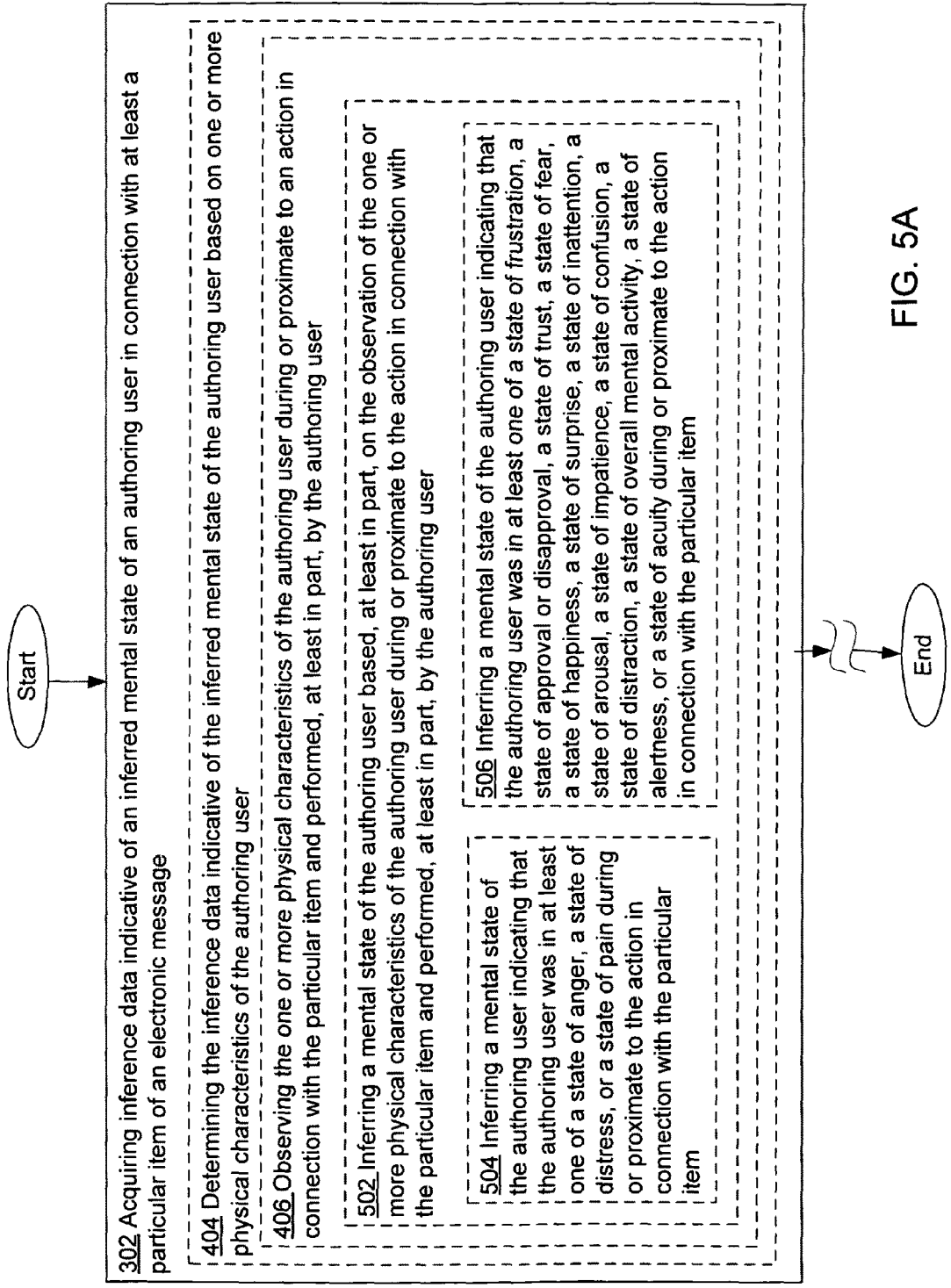
FIG. 5A is a high-level logic flowchart of a process depicting alternate implementations of the observation operation 406 of FIG. 4.

In some embodiments, the observation operation 406 may further include one or more additional operations. For example, and as illustrated in FIG. 5A, the observation operation 406 in some embodiments may include an inference operation 502 for inferring a mental state of the authoring user based, at least in part, on the observing of the one or more physical characteristics of the authoring user during or proximate to the action in connection with the particular item and performed, at least in part, by the authoring user. For instance, in some implementations, the mental state inference module 106 of the authoring network device 10 inferring a mental state of the authoring user 18 based, at least in part, on the observing (e.g., via one or more sensors 48 including, for example, an EEG device 142 and/or MEG device 143) of the one or more physical characteristics (e.g., brain activity) of the authoring user 18 during or proximate to the action (e.g., any one or more of creating, modifying, deleting, and so forth) in connection with the particular item 21 and performed, at least in part, by the authoring user 18. For these implementations, the inference to a particular mental state for the authoring user 18 may be made by, for example, determining a brain activity pattern for the authoring user 18 based on data provided by the one or more sensors 48 (e.g., an EEG device 142 and/or an MEG device 143) and then comparing the determined brain activity pattern of the authoring user 18 to brain activity patterns that may be stored in a database or library (each of the stored brain activity patterns being linked with, for example, a corresponding mental state).

As further depicted in FIG. 5A, inference operation 502 may further include one or more additional operations in various alternative embodiments. For example, in some embodiments, inference operation 502 may include an operation 504 for inferring a mental state of the authoring user indicating that the authoring user was in at least one of a state of anger, a state of distress, or a state of pain during or proximate to the action in connection with the particular item. For instance, the mental state inference module 106 of the authoring network device 10 inferring a mental state of the authoring user 18 (e.g., based on data provided by one or more sensors 48 including, for example, an fMRI device 140 and/or an fNIR device 141) indicating that the authoring user 18 was in at least one of a state of anger, a state of distress, or a state of pain during or proximate to the action (e.g., any one more of extracting, forwarding, storing, and so forth) in connection with the particular item 21.

In the same or alternative embodiments, the inference operation 502 may include an operation 506 for inferring a mental state of the authoring user indicating that the authoring user was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action in connection with the particular item as depicted in FIG. 5A. For instance, the mental state inference module 106 of the authoring network device 10 inferring a mental state of the authoring user 18 (e.g., based on data provided by one or more sensors 48 including, for example, an EEG device 142 and/or an MEG device 143) indicating that the authoring user 18 was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action (e.g., any one or more of activating, deactivating, tagging, associating, and so forth) in connection with the particular item 21.

Figure 5B:
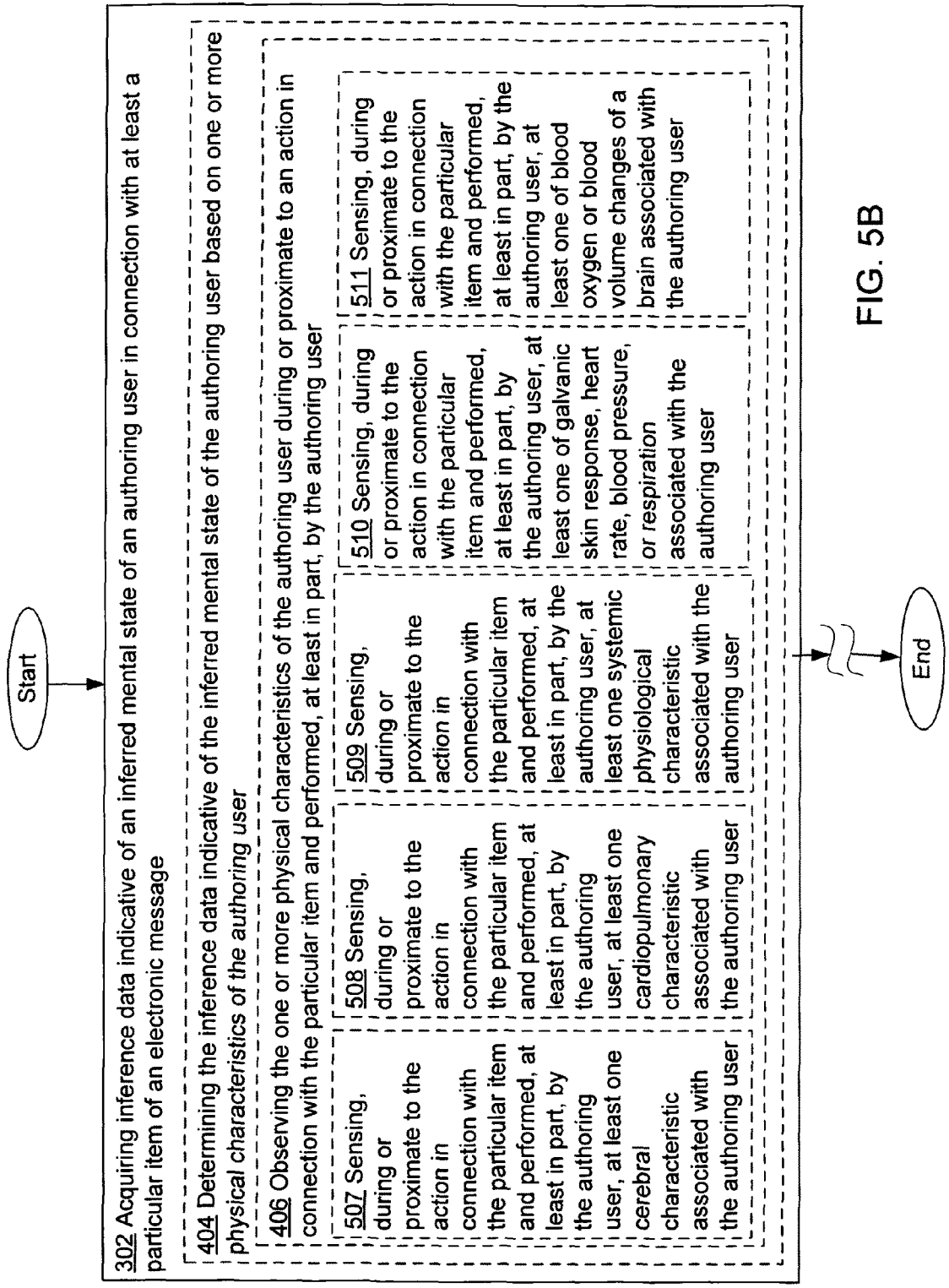
FIG. 5B is a high-level logic flowchart of a process depicting more alternate implementations of the observation operation 406 of FIG. 4.
Figure 5C:
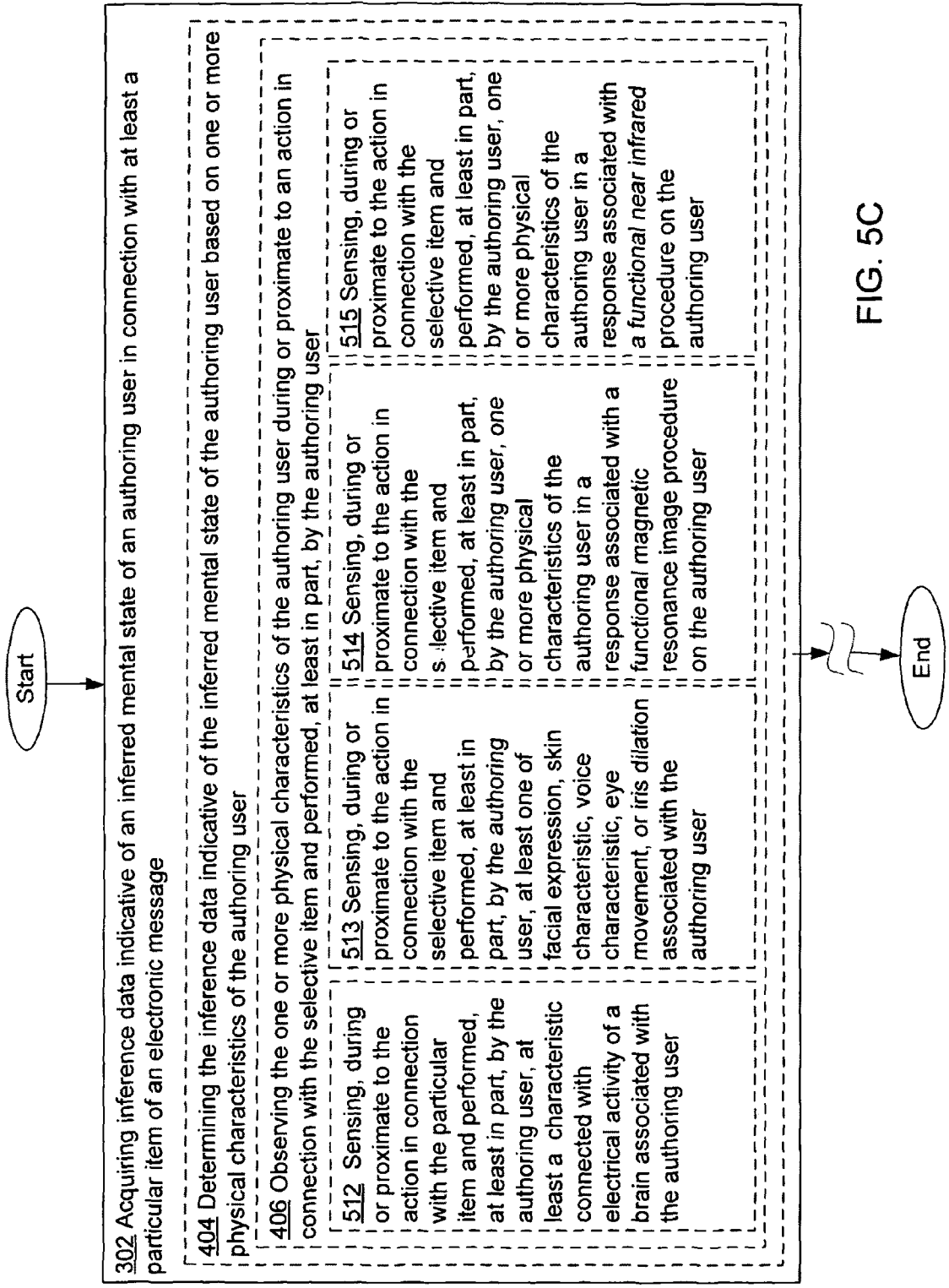
FIG. 5C is a high-level logic flowchart of a process depicting more alternate implementations of the observation operation 406 of FIG. 4.

In some embodiments, the observation operation 406 may include one or more sensing operations as illustrated in FIGS. 5B and 5C. For example, in some implementations, the observation operation 406 may include a sensing operation 507 for sensing, during or proximate to the action in connection with the particular item and performed, at least in part, by the authoring user, at least one cerebral characteristic associated with the authoring user as illustrated in FIG. 5B. For instance, the physical characteristic sensing module 108 (see FIG. 2A) of the authoring network device 10 sensing (e.g., via an fMRI device 140, an fNIR device 141, an EEG device 142, and/or an MEG device 143), during or proximate to the action (e.g., any one or more of categorizing, substituting, inserting, and so forth) in connection with the particular item 21 and performed, at least in part, by the authoring user 18, at least one cerebral characteristic (e.g., characteristic associated with electrical activity or blood oxygen changes of a brain) associated with the authoring user 18.

In the same or alternative embodiments, the observation operation 406 may include a sensing operation 508 for sensing, during or proximate to the action in connection with the particular item and performed, at least in part, by the authoring user, at least one cardiopulmonary characteristic associated with the authoring user as illustrated in FIG. 5B. For instance, the physical characteristic sensing module 108 of the authoring network device 10 sensing (e.g., via a heart rate sensor device 145), during or proximate to the action (e.g., any one or more of creating, modifying, deleting, and so forth) in connection with the particular item 21 and performed, at least in part, by the authoring user 18, at least one cardiopulmonary characteristic (e.g., heart rate) associated with the authoring user 18.

In the same or alternative embodiments, the observation operation 406 may include a sensing operation 509 for sensing, during or proximate to the action in connection with the particular item and performed, at least in part, by the authoring user, at least one systemic physiological characteristic associated with the authoring user as illustrated in FIG. 5B. For instance, the physical characteristic sensing module 108 of the authoring network device 10 sensing (e.g., via a blood pressure sensor device 146 and/or a respiration sensor device 147), during or proximate to the action (e.g., any one or more of relocating, extracting, extracting, and so forth) in connection with the particular item 21 and performed, at least in part, by the authoring user 18, at least one systemic physiological characteristic (e.g., blood pressure and/or respiration) associated with the authoring user 18.

In the same or alternative embodiments, the observation operation 406 may include a sensing operation 510 for sensing, during or proximate to the action in connection with the particular item and performed, at least in part, by the authoring user, at least one of galvanic skin response, heart rate, blood pressure, or respiration associated with the authoring user as illustrated in FIG. 5B. For instance, the physical characteristic sensing module 108 of the authoring network device 10 sensing (e.g., via a galvanic skin sensor device 144, a heart rate sensor device 145, a blood pressure sensor device 146, and/or respiration sensor device 147), during or proximate to the action (e.g., any one or more of forwarding, storing, activating or deactivating, tagging, and so forth) in connection with the particular item 21 and performed, at least in part, by the authoring user 18, at least one of galvanic skin response, heart rate, blood pressure, or respiration associated with the authoring user 18.

In the same or alternative embodiments, the observation operation 406 may include a sensing operation 511 for sensing, during or proximate to the action in connection with the particular item and performed, at least in part, by the authoring user, at least one of blood oxygen or blood volume changes of a brain associated with the authoring user as illustrated ion FIG. 5B. For instance, the physical characteristic sensing module 108 of the authoring network device 10 sensing (e.g., via an fMRI device 140 and/or fNIR device 141), during or proximate to the action (e.g., any one or more of associating, categorizing, substituting inserting, and so forth) in connection with the particular item 21 and performed, at least in part, by the authoring user 18, at least one of blood oxygen or blood volume changes of a brain associated with the authoring user 18.

In the same or alternative embodiments, the observation operation 406 may include a sensing operation 512 for sensing, during or proximate to the action in connection with the particular item and performed, at least in part, by the authoring user, at least a characteristic connected with electrical activity of a brain associated with the authoring user as illustrated in FIG. 5C. For instance, the physical characteristic sensing module 108 of the authoring network device 10 sensing (e.g., via an EEG device 142 and/or an MEG device 143), during or proximate to the action (e.g., any one or more of associating, creating, modifying, deleting, and so forth) in connection with the particular item 21 and performed, at least in part, by the authoring user 18, at least a characteristic connected with electrical activity of a brain associated with the authoring user 18. For example, if an MEG device 143 is employed for sensing physical characteristics of the authoring user 18 then the magnetic fields produced by the electrical activities of the brain of the authoring user 18 may be sensed by the MEG device 143.

In the same or alternative embodiments, the observation operation 406 may include a sensing operation 513 for sensing, during or proximate to the action in connection with the particular item and performed, at least in part, by the authoring user, at least one of facial expression, skin characteristic, voice characteristic, eye movement, or iris dilation associated with the authoring user as illustrated in FIG. 5C. For instance, the physical characteristic sensing module 108 of the authoring network device 10 sensing (e.g., via a facial expression sensor device 148, skin characteristic sensor device 149, voice response device 150, gaze tracking device 151, and/or iris response device 152), during or proximate to the action (e.g., one or more of relocating, extracting forwarding, and so forth) in connection with the particular item 21 and performed, at least in part, by the authoring user 18, at least one of facial expression, skin characteristic, voice characteristic, eye movement, or iris dilation associated with the authoring user 18.

In the same or alternative embodiments, the observation operation 406 may include a sensing operation 514 for sensing, during or proximate to the action in connection with the particular item and performed, at least in part, by the authoring user, one or more physical characteristics of the authoring user in a response associated with a functional magnetic resonance imaging procedure on the authoring user as illustrated in FIG. 5C. For instance, the physical characteristic sensing module 108 of the authoring network device 10 sensing (e.g., via an fMRI device 140), during or proximate to the action (e.g., one or more of storing, activating or deactivating, tagging, associating, and so forth) in connection with the particular item 21 and performed, at least in part, by the authoring user 18, one or more physical characteristics (e.g., blood oxygen or blood volume changes of the brain) of the authoring user 18 in a response associated with a functional magnetic resonance imaging procedure on the authoring user 18.

In the same or alternative embodiments, the observation operation 406 may include a sensing operation 515 for sensing, during or proximate to the action in connection with the particular item and performed, at least in part, by the authoring user, one or more physical characteristics of the authoring user in a response associated with a functional near infrared procedure on the authoring user as illustrated in FIG. 5C. For instance, the physical characteristic sensing module 108 of the authoring network device 10 sensing (e.g., via an fNIR device 141), during or proximate to the action (e.g., one or more of categorizing, substituting, inserting, and so forth) in connection with the particular item 21 and performed, at least in part, by the authoring user 18, one or more physical characteristics (e.g., blood oxygen or blood volume changes of the brain) of the authoring user 18 in a response associated with a functional near infrared procedure on the authoring user 18.

Figure 5D:
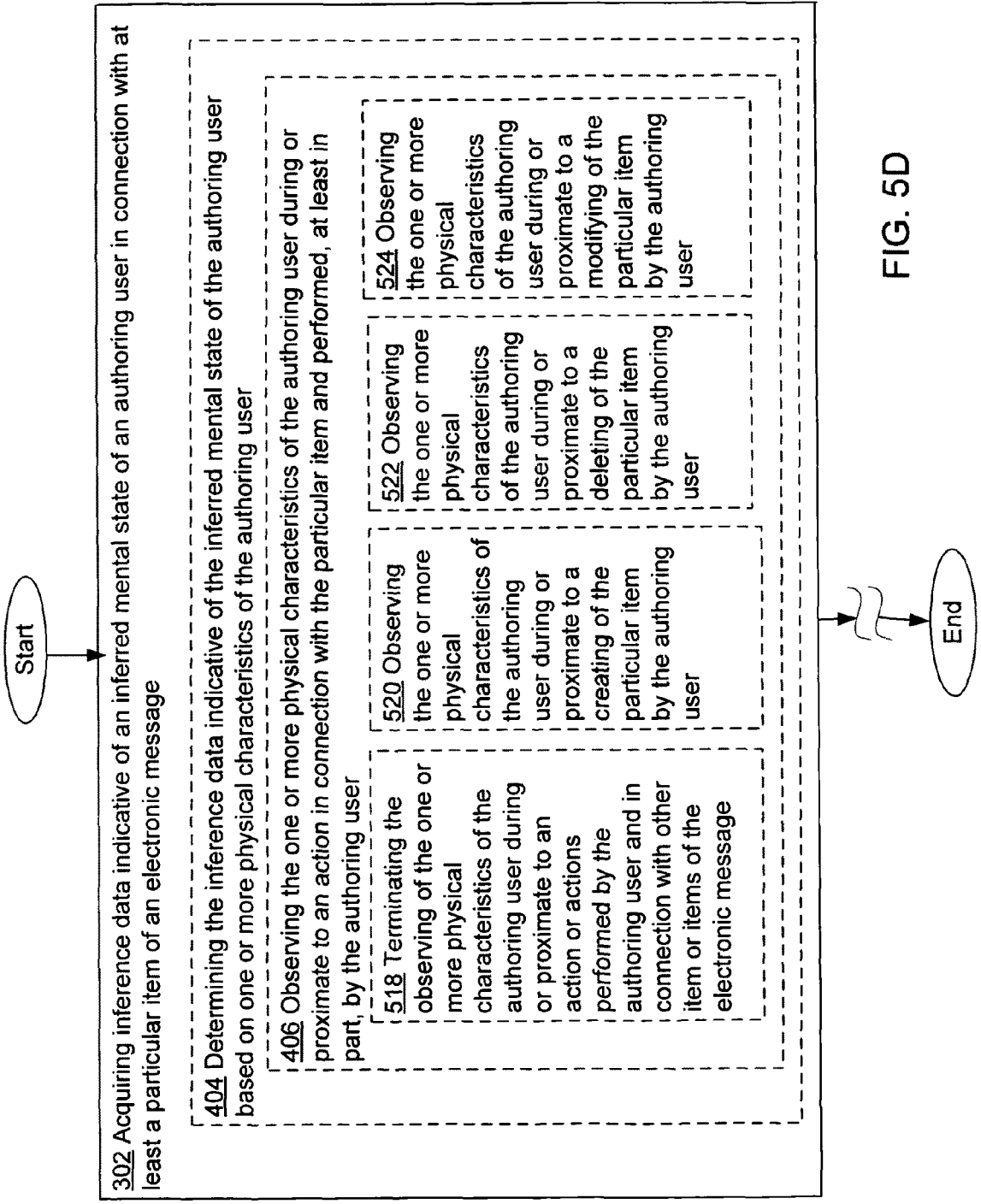
FIG. 5D is a high-level logic flowchart of a process depicting more alternate implementations of the observation operation 406 of FIG. 4.

In the same or alternative embodiments, the observation operation 406 may include a terminating operation 518 for terminating the observing of the one or more physical characteristics of the authoring user during or proximate to an action or actions performed by the authoring user and in connection with other item or items of the electronic message as illustrated in FIG. 5D. For instance, the physical characteristic observation module 104 (see FIG. 2A) of the authoring network device 10 terminating the observing (e.g., via one or more of fMRI device 140, fNIR device 141, EEG device 142, MEG device 143, and so forth) of the one or more physical characteristics (e.g., cerebral characteristics) of the authoring user 18 during or proximate to an action or actions (e.g., one or more of creating, modifying, deleting, and so forth) performed by the authoring user 18 and in connection with other item or items (e.g., another particular item 22, item 3, and/or item 4 in FIG. 2G) of the electronic message 20. In some implementations, this may mean that the physical characteristic observation module 104 controlling the one or more sensors 48 (e.g., via one or more of fMRI device 140, fNIR device 141, EEG device 142, MEG device 143, and so forth) to selectively activating the sensors 48 only at or around the time when an action or actions is being performed by the authoring user 18 in connection with the particular item 21, and to deactivating the sensors 48 when the authoring user 18 is performing an action or actions in connection with other item or items (e.g., another particular item 22, item 3, and/or item 4 in FIG. 2G) of the electronic message 20.

In the same or alternative embodiments, the observation operation 406 may include an observation operation 520 for observing the one or more physical characteristics of the authoring user during or proximate to a creating of the particular item by the authoring user as illustrated in FIG. 5D. For example, the physical characteristic observation module 104 of the authoring network device 10 observing (e.g., via an fMRI device 140) the one or more physical characteristics (e.g., blood oxygen or blood volume changes of a brain) of the authoring user 18 during or proximate to a creating (e.g., via a creation module 112) of the particular item 21 by the authoring user 18.

In the same or alternative embodiments, the observation operation 406 may include an observation operation 522 for observing the one or more physical characteristics of the authoring user during or proximate to a deleting of the particular item by the authoring user as illustrated in FIG. 5D. For example, the physical characteristic observation module 104 of the authoring network device 10 observing (e.g., via an fNIR device 141) the one or more physical characteristics (e.g., blood oxygen or blood volume changes of a brain) of the authoring user 18 during or proximate to a deleting (e.g., via a deletion module 114) of the particular item 21 by the authoring user 18.

In the same or alternative embodiments, the observation operation 406 may include an observation operation 524 for observing the one or more physical characteristics of the authoring user during or proximate to a modifying of the particular item by the authoring user as illustrated in FIG. 5D. For instance, the physical characteristic observation module 104 of the authoring network device 10 observing (e.g., via an EEG device 142) the one or more physical characteristics (e.g., electrical activity of the brain) of the authoring user 18 during or proximate to a modifying (e.g., via a modification module 113) of the particular item 21 by the authoring user 18.

Figure 5E:
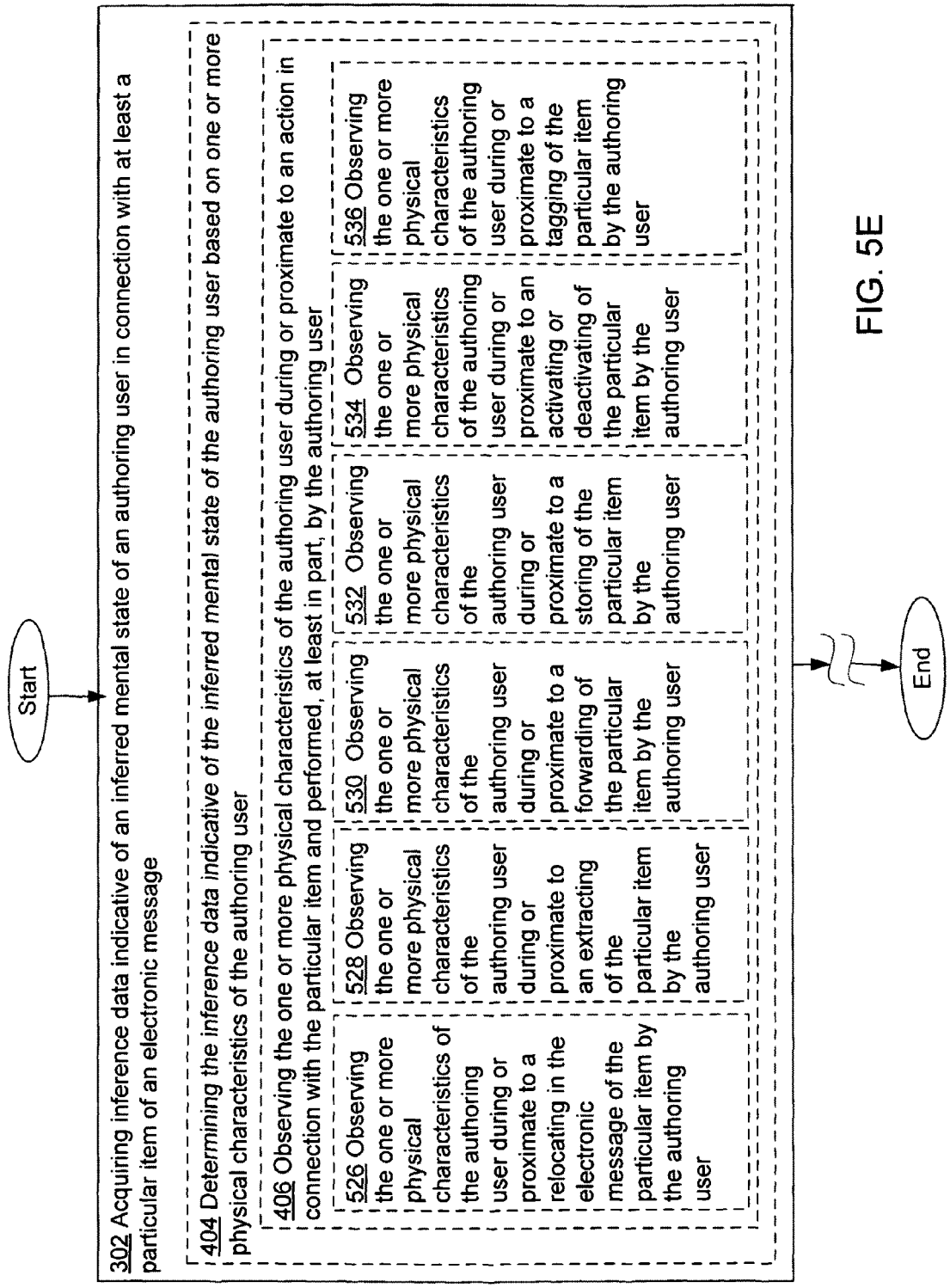
FIG. 5E is a high-level logic flowchart of a process depicting more alternate implementations of the observation operation 406 of FIG. 4.

In the same or alternative embodiments, the observation operation 406 may include an observation operation 526 for observing the one or more physical characteristics of the authoring user during or proximate to a relocating in the electronic message of the particular item by the authoring user as illustrated in FIG. 5E. For instance, the physical characteristic observation module 104 of the authoring network device 10 observing (e.g., via an MEG device 143) the one or more physical characteristics (e.g., a characteristic associated with electrical activity of the brain) of the authoring user 18 during or proximate to a relocating (e.g., via a relocation module 115) in the electronic message 20 of the particular item 21 by the authoring user 18.

In the same or alternative embodiments, the observation operation 406 may include an observation operation 528 for observing the one or more physical characteristics of the authoring user during or proximate to an extracting of the particular item by the authoring user as illustrated in FIG. 5E. For instance, the physical characteristic observation module 104 of the authoring network device 10 observing (e.g., via a galvanic skin sensor device) the one or more physical characteristics (e.g., galvanic skin response) of the authoring user 18 during or proximate to an extracting (e.g., via an extraction module 116) of the particular item 21 by the authoring user 18.

In the same or alternative embodiments, the observation operation 406 may include an observation operation 530 for observing the one or more physical characteristics of the authoring user during or proximate to a forwarding of the particular item by the authoring user as illustrated in FIG. 5E. For instance, the physical characteristic observation module 104 of the authoring network device 10 observing (e.g., via a heart rate sensor device 145) the one or more physical characteristics (e.g., heart rate) of the authoring user 18 during or proximate to a forwarding (e.g., via a forwarding module 117) of the particular item 21 by the authoring user 18.

In the same or alternative embodiments, the observation operation 406 may include an observation operation 532 for observing the one or more physical characteristics of the authoring user during or proximate to a storing of the particular item by the authoring user as illustrated in FIG. 5E. For instance, the physical characteristic observation module 104 of the authoring network device 10 observing (e.g., via a blood pressure sensor device 146) the one or more physical characteristics (e.g., blood pressure) of the authoring user 18 during or proximate to a storing (e.g., via a storing module 118) of the particular item 21 by the authoring user 18.

In the same or alternative embodiments, the observation operation 406 may include an observation operation 534 for observing the one or more physical characteristics of the authoring user during or proximate to an activating or deactivating of the particular item by the authoring user as illustrated in FIG. 5E. For instance, the physical characteristic observation module 104 of the authoring network device 10 observing (e.g., via a respiration sensor device 147) the one or more physical characteristics (e.g., respiration) of the authoring user 18 during or proximate to an activating or deactivating (e.g., via an activating and deactivating module 119) of the particular item 21 by the authoring user 18.

In the same or alternative embodiments, the observation operation 406 may include an observation operation 536 for observing the one or more physical characteristics of the authoring user during or proximate to a tagging of the particular item by the authoring user as illustrated in FIG. 5E. For instance, the physical characteristic observation module 104 of the authoring network device 10 observing (e.g., via a facial expression sensor device 148) the one or more physical characteristics (e.g., facial expression) of the authoring user 18 during or proximate to a tagging (e.g., via a tagging module 120) of the particular item 21 by the authoring user 18.

Figure 5F:
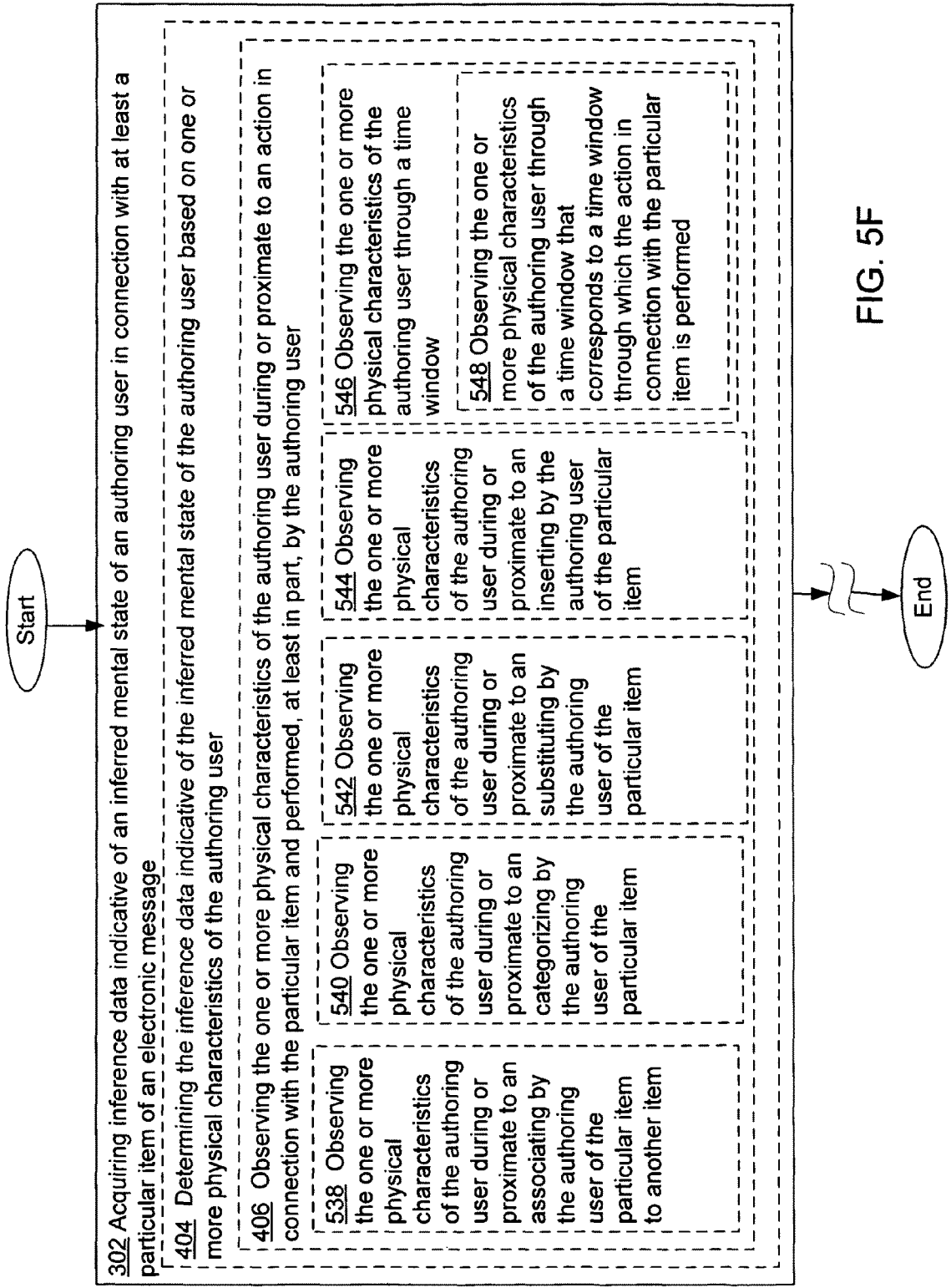
FIG. 5F is a high-level logic flowchart of a process depicting more alternate implementations of the observation operation 406 of FIG. 4.

In the same or alternative embodiments, the observation operation 406 may include an observation operation 538 for observing the one or more physical characteristics of the authoring user during or proximate to an associating by the authoring user of the particular item to another item as illustrated in FIG. 5F. For instance, the physical characteristic observation module 104 of the authoring network device 10 observing (e.g., via a skin characteristic sensor device 149) the one or more physical characteristics (e.g., skin characteristics) of the authoring user 18 during or proximate to an associating (e.g., via an associating module 121) by the authoring user 18 of the particular item 21 to another item (e.g., item 3 of electronic message 20 of FIG. 2G).

In the same or alternative embodiments, the observation operation 406 may include an observation operation 540 for observing the one or more physical characteristics of the authoring user during or proximate to a categorizing by the authoring user of the particular item as illustrated in FIG. 5F. For instance, the physical characteristic observation module 104 of the authoring network device 10 observing (e.g., via a voice response device 150) the one or more physical characteristics (e.g., voice characteristics) of the authoring user 18 during or proximate to a categorizing (e.g., via a categorizing module 122) by the authoring user 18 of the particular item 21.

In the same or alternative embodiments, the observation operation 406 may include an observation operation 542 for observing the one or more physical characteristics of the authoring user during or proximate to a substituting by the authoring user of the particular item as illustrated in FIG. 2F. For instance, the physical characteristic observation module 104 of the authoring network device 10 observing (e.g., via a gaze tracking device 151) the one or more physical characteristics (e.g., eye or iris movement) of the authoring user 18 during or proximate to a substituting (e.g., via a substituting module 123) by the authoring user 18 of the particular item 21.

In some embodiments, the observation operation 406 may include an observation operation 544 for observing the one or more physical characteristics of the authoring user during or proximate to an inserting by the authoring user of the particular item as illustrated in FIG. 5F. For instance, the physical characteristic observation module 104 of the authoring network device 10 observing (e.g., via iris response device 152) the one or more physical characteristics (e.g., iris dilation) of the authoring user 18 during or proximate to an inserting (e.g., via an inserting module 124) by the authoring user 18 of the particular item 21 into the electronic message 20.

In various alternative embodiments, the observation of the one or more physical characteristics of the authoring user 18 may occur during or proximate to other types of actions (which may be directly or indirectly connected to the particular item 21) other than those described above (e.g., creating, deleting, modifying, and so forth). For instance, in some alternative implementations, the observation of the one or more physical characteristics of the authoring user 18 may occur during or proximate to a searching operation (e.g., in order to find particular information) initiated by the authoring user 18 and that may have been prompted while accessing the particular item 21.

In some embodiments, the observation operation 406 may include an observation operation 546 for observing the one or more physical characteristics of the authoring user through a time window as illustrated in FIG. 2F. For instance, the physical characteristic observation module 104 of the authoring network device 10 observing (e.g., via an fMRI device 140 and/or an fNIR device 141) the one or more physical characteristics (e.g., blood oxygen or blood volume changes of a brain) of the authoring user 18 through a time window (e.g., as provided by a time window module 126 of time module 36—see FIG. 2D).

In some embodiments, the observation operation 546 may also include an observation operation 548 for observing the one or more physical characteristics of the authoring user through a time window that corresponds to a time window through which the action in connection with the particular item is performed as illustrated in FIG. 2F. For instance, the physical characteristic observation module 104 of the authoring network device 10 observing (e.g., via an EEG device 142) the one or more physical characteristics (e.g., electrical activities of the brain) of the authoring user 18 through a time window (e.g., as provided by a time window module 126) that corresponds to a time window (e.g., may be the same time window or a different time window) through which the action (e.g., creating, modifying, deleting, and so forth) in connection with the particular item 21 is performed.

Figure 6:
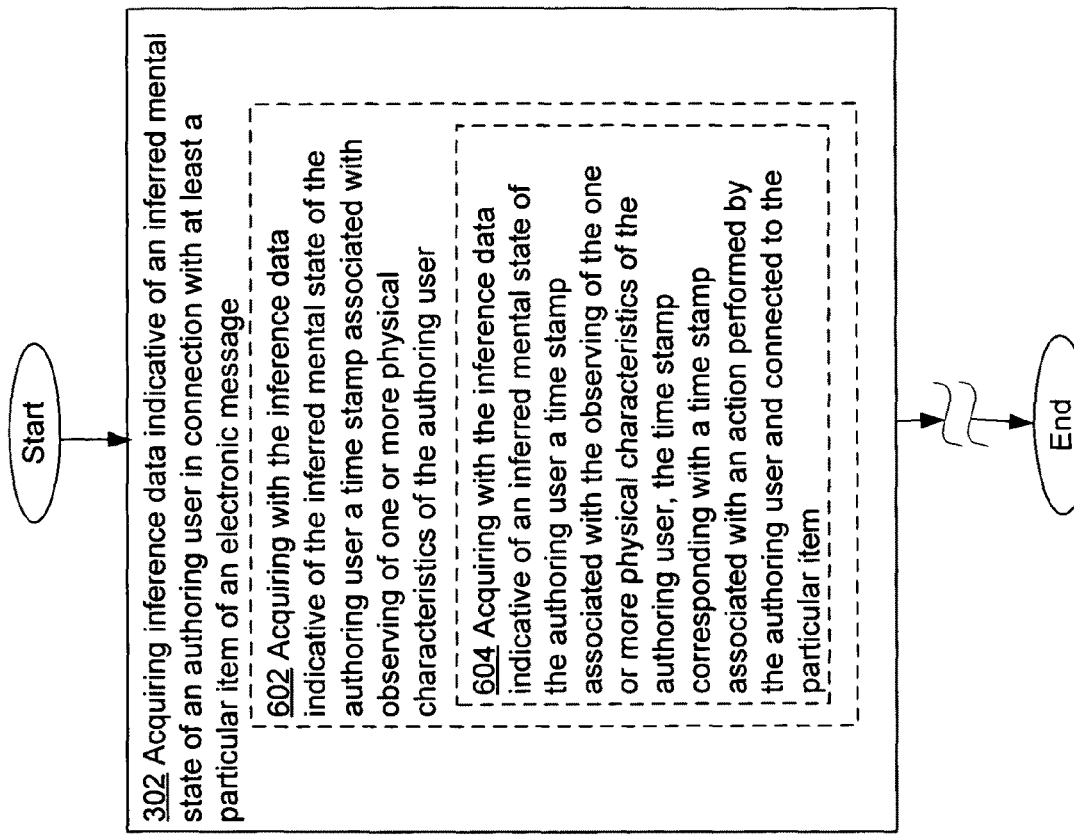
FIG. 6 is a high-level logic flowchart of a process depicting more alternate implementations of the inference data acquisition operation 302 of FIG. 3.

In various embodiments, the acquisition operation 302 may include an operation 602 for acquiring with the inference data indicative of the inferred mental state of the authoring user a time stamp associated with observing of one or more physical characteristics of the authoring user as illustrated in FIG. 6. For instance, the inference data acquisition module 30 of the authoring network device 10 acquiring with the inference data indicative of the inferred mental state of the authoring user 18 a time stamp (e.g., as provided by a time stamp module 125 of a time module 36—see FIG. 2D) associated with observing (e.g., as performed, at least in part, by one or more sensors 48) of one or more physical characteristics of the authoring user 18.

In some embodiments, operation 602 may further include an operation 604 for acquiring with the inference data indicative of the inferred mental state of the authoring user a time stamp associated with the observing of the one or more physical characteristics of the authoring user, the time stamp corresponding with a time stamp associated with an action performed by the authoring user and connected to the particular item as further illustrated in FIG. 6. For instance, the inference data acquisition module 30 of the authoring network device 10 acquiring with the inference data indicative of the inferred mental state of the authoring user 18 a time stamp (e.g., as provided by a time stamp module 125) associated with the observing of the one or more physical characteristics of the authoring user 18, the time stamp corresponding with a time stamp (e.g., may be the same or a different time stamp) associated with an action (e.g., at least one of creating, modifying, deleting, and so forth) performed by the authoring user 18 and connected to the particular item 21.

Figure 7A:
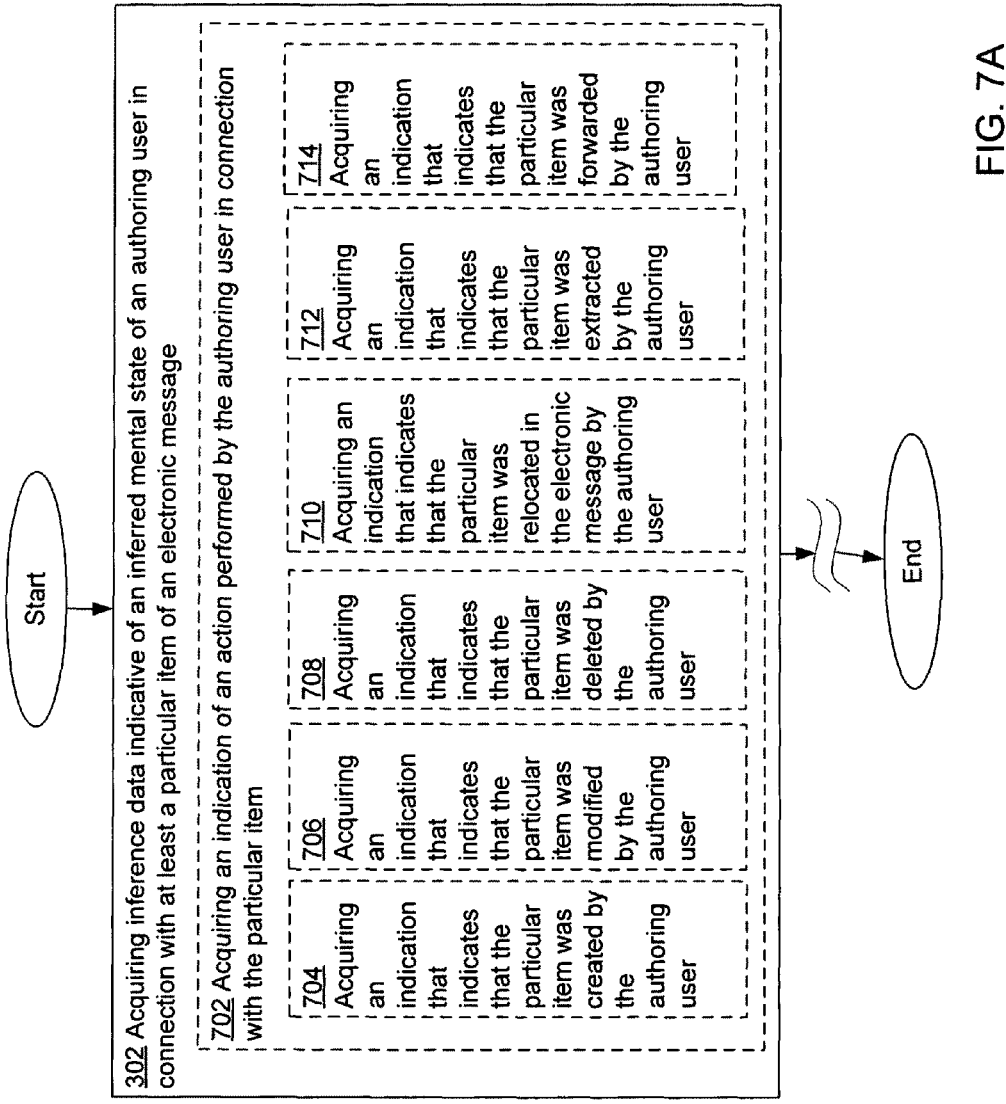
FIG. 7A is a high-level logic flowchart of a process depicting some more alternate implementations of the inference data acquisition operation 302 of FIG. 3.
Figure 7B:
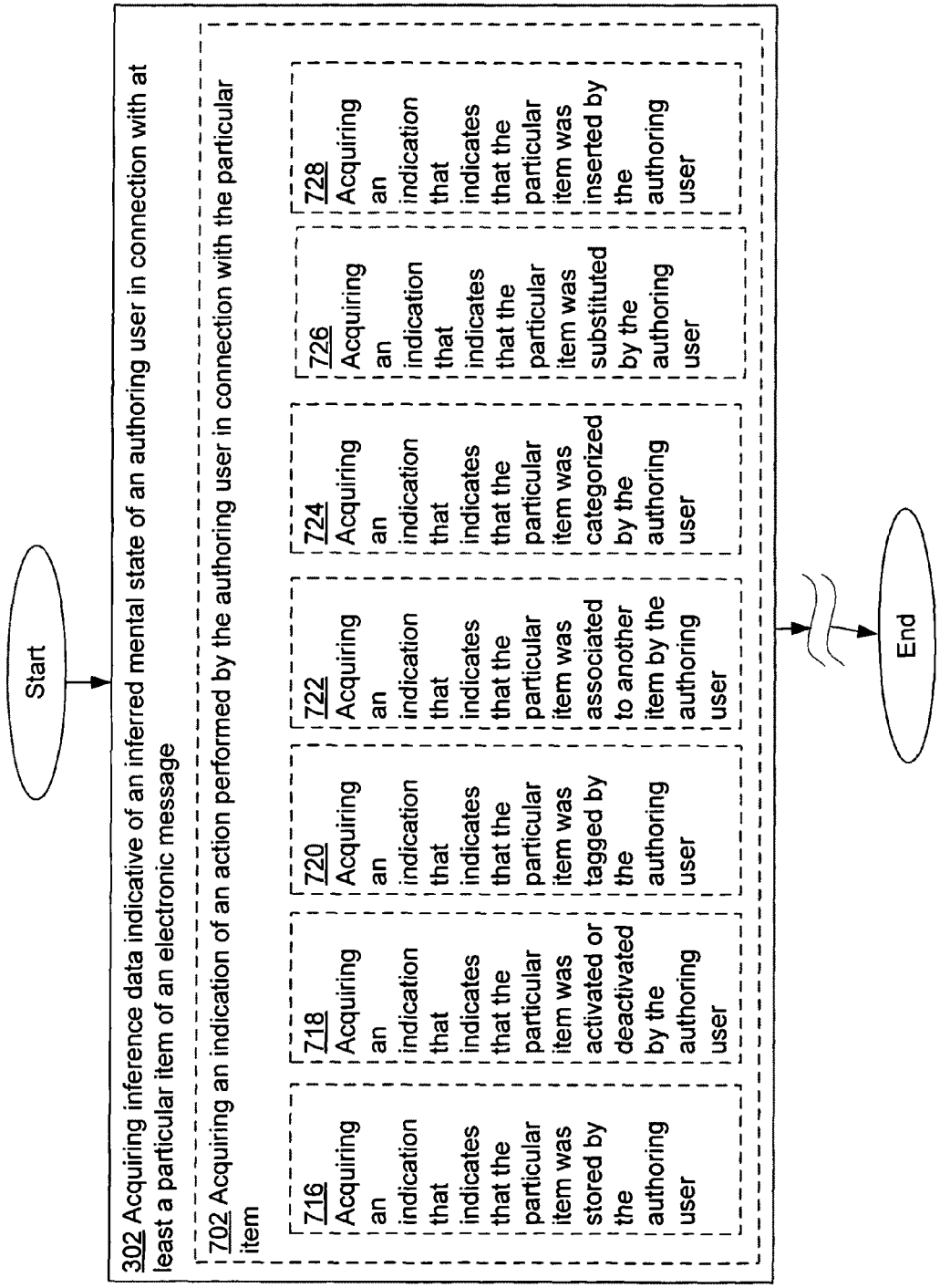
FIG. 7B is a high-level logic flowchart of a process depicting some more alternate implementations of the inference data acquisition operation 302 of FIG. 3.

In various embodiments, inference data acquisition operation 302 may included an operation 702 for acquiring an indication of an action performed by the authoring user in connection with the particular item as illustrated in FIGS. 7A and 7B. For instance, the inference data acquisition module 30 of the authoring network device 10 acquiring an indication (e.g., an identifier or symbolic representation) of an action (e.g., via an action module 34) performed by the authoring user 18 in connection with the particular item 21.

In some embodiments, operation 702 may include one or more additional operations as illustrated in FIGS. 7A and 7B. For example, in particular embodiments operation 702 may include an operation 704 for acquiring an indication that indicates that the particular item was created by the authoring user as illustrated in FIG. 7A. For instance, the inference data acquisition module 30 of the authoring network device 10 acquiring an indication (e.g., as provided by action module 34) that indicates that the particular item 21 was created (e.g., via a creation module 112) by the authoring user 18.

In the same or alternative embodiments, operation 702 may include an operation 706 for acquiring an indication that indicates that the particular item was modified by the authoring user as illustrated in FIG. 7A. For instance, inference data acquisition module 30 of the authoring network device 10 acquiring an indication (e.g., as provided by action module 34) that indicates that the particular item 21 was modified (e.g., via a modification module 113) by the authoring user 18.

In the same or alternative embodiments, operation 702 may include an operation 708 for acquiring an indication that indicates that the particular item was deleted by the authoring user as illustrated in FIG. 7A. For instance, the inference data acquisition module 30 of the authoring network device 10 acquiring an indication (e.g., as provided by action module 34) that indicates that the particular item 21 was deleted (e.g., via a deletion module 114) by the authoring user 18.

In the same or alternative embodiments, operation 702 may include an operation 710 for acquiring an indication that indicates that the particular item was relocated in the electronic message by the authoring user as illustrated in FIG. 7A. For instance, the inference data acquisition module 30 of the authoring network device 10 acquiring an indication (e.g., as provided by action module 34) that indicates that the particular item 21 was relocated (e.g., via a relocation module 115) in the electronic message 20 by the authoring user 18.

In the same or alternative embodiments, operation 702 may include an operation 712 for acquiring an indication that indicates that the particular item was extracted by the authoring user as illustrated in FIG. 7A. For instance, the inference data acquisition module 30 of the authoring network device 10 acquiring an indication (e.g., as provided by action module 34) that indicates that the particular item 21 was extracted (e.g., via an extraction module 116) by the authoring user 18.

In the same or alternative embodiments, operation 702 may include an operation 714 for acquiring an indication that indicates that the particular item was forwarded by the authoring user as illustrated in FIG. 7A. For instance, the inference data acquisition module 30 of the authoring network device 10 acquiring an indication (e.g., as provided by action module 34) that indicates that the particular item 21 was forwarded (e.g., via a forwarding module 117) by the authoring user 18.

In the same or alternative embodiments, operation 702 may include an operation 716 for acquiring an indication that indicates that the particular item was stored by the authoring user as illustrated in FIG. 7B. For instance, the inference data acquisition module 30 of the authoring network device 10 acquiring an indication (e.g., as provided by action module 34) that indicates that the particular item 21 was stored (e.g., via a storing module 118) by the authoring user 18.

In the same or alternative embodiments, operation 702 may include an operation 718 for acquiring an indication that indicates that the particular item was activated or deactivated by the authoring user as illustrated in FIG. 7B. For instance, the inference data acquisition module 30 of the authoring network device 10 acquiring an indication (e.g., as provided by action module 34) that indicates that the particular item 21 was activated or deactivated (e.g., via an activating and deactivating module 119) by the authoring user 18.

In the same or alternative embodiments, operation 702 may include an operation 720 for acquiring an indication that indicates that the particular item was tagged by the authoring user as illustrated in FIG. 7B. For instance, the inference data acquisition module 30 of the authoring network device 10 acquiring an indication (e.g., as provided by action module 34) that indicates that the particular item 21 was tagged (e.g., via a tagging module 120) by the authoring user 18.

In the same or alternative embodiments, operation 702 may include an operation 722 for acquiring an indication that indicates that the particular item was associated to another item by the authoring user as illustrated in FIG. 7B. For instance, the inference data acquisition module 30 of the authoring network device 10 acquiring an indication (e.g., as provided by action module 34) that indicates that the particular item 21 was associated (e.g., via an associating module 121) to another item by the authoring user 18.

In the same or alternative embodiments, operation 702 may include an operation 724 for acquiring an indication that indicates that the particular item was categorized by the authoring user as illustrated in FIG. 7B. For instance, the inference data acquisition module 30 of the authoring network device 10 acquiring an indication (e.g., as provided by action module 34) that indicates that the particular item 21 was categorized (e.g., via a categorizing module 122) by the authoring user 18.

In the same or alternative embodiments, operation 702 may include an operation 726 for acquiring an indication that indicates that the particular item was substituted by the authoring user as illustrated in FIG. 7B. For instance, the inference data acquisition module 30 of the authoring network device 10 acquiring an indication (e.g., as provided by action module 34) that indicates that the particular item 21 was substituted (e.g., via a substituting module 123) by the authoring user 18.

In the same or alternative embodiments, operation 702 may include an operation 728 for acquiring an indication that indicates that the particular item was inserted by the authoring user as illustrated in FIG. 7B. For instance, the inference data acquisition module 30 of the authoring network device 10 acquiring an indication (e.g., as provided by action module 34) that indicates that the particular item 21 was inserted (e.g., via an inserting module 124) into the electronic message 20 by the authoring user 18.

Figure 8A:
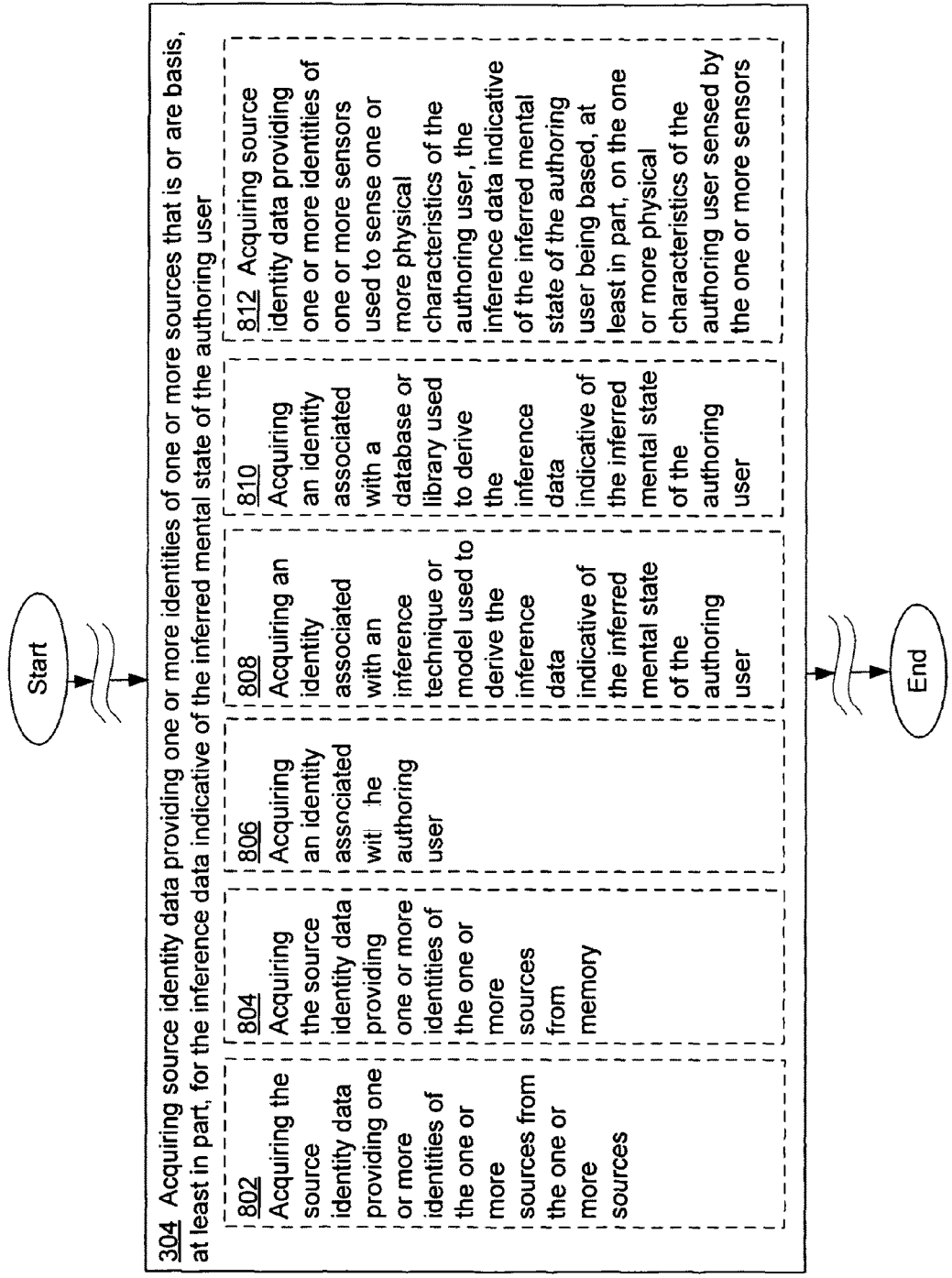
FIG. 8A is a high-level logic flowchart of a process depicting alternate implementations of the source identity acquisition operation 304 of FIG. 1.

In various embodiments, the source identity acquisition operation 304 depicted in FIG. 3 may include one or more additional operations. For example, in some implementations, source identity acquisition operation 304 may include an operation 802 for acquiring the source identity data providing one or more identities of the one or more sources from the one or more sources as illustrated in FIG. 8A. For instance, the source identity acquisition module 31 of the authoring network device 10 acquiring the source identity data providing one or more identities (e.g., name or address) of the one or more sources (e.g., database or library storing physical characteristics patterns that may be used in order to derive an inferred mental state for the authoring user 18) from the one or more sources.

In the same or different implementations, the source identity acquisition operation 304 may include an operation 804 for acquiring the source identity data providing one or more identities of the one or more sources from memory as illustrated in FIG. 8A. For instance, the source identity acquisition module 31 of the authoring network device 10 acquiring the source identity data providing one or more identities (e.g., identifying the model numbers or the sensor types of the one or more sensors 48 that may be used to acquire the inference data indicative of the inferred mental state of the authoring user 18) of the one or more sources (e.g., one or more sensors 48 including, for example, any one or more of an fMRI device 140, an fNIR device 141, and so forth) from memory 49.

In some implementations, the source identity acquisition operation 304 may include an operation 806 for acquiring an identity associated with the authoring user as illustrated in FIG. 8A. For example, the authoring user identification (ID) acquisition module 201 of the authoring network device 10 acquiring (e.g., from memory 49) an identity (e.g., user name or identification) associated with the authoring user 18.

In some implementations, the source identity acquisition operation 304 may include an operation 808 for acquiring an identity associated with an inference technique or model used to derive the inference data indicative of the inferred mental state of the authoring user as illustrated in FIG. 8A. For instance, the inference technique or model identification (ID) acquisition module 202 of the authoring network device 10 acquiring (e.g., from memory 49) an identity (e.g., name) associated with an inference technique or model used to derive the inference data indicative of the inferred mental state of the authoring user 18.

In some implementations, the source identity acquisition operation 304 may include an operation 810 for acquiring an identity associated with a database or library used to derive the inference data indicative of the inferred mental state of the authoring user as illustrated in FIG. 8A. For instance, the database or library acquisition module 203 of the authoring network device 10 acquiring (e.g., from memory 49) an identity (e.g., name or address) associated with a database or library used to derive the inference data indicative of the inferred mental state (e.g., state of happiness, state of anger, and so forth) of the authoring user 18.

In some implementations, the source identity acquisition operation 304 may include an operation 812 for acquiring source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors as illustrated in FIG. 8A. For instance, the sensor identification (ID) acquisition module 204 of the authoring network device 10 acquiring (e.g., from memory 49 or from the one or more sensors 48) source identity data providing one or more identities (e.g., sensor type or sensor model number) of one or more sensors 48 (e.g., fMRI device 140, an fNIR device 141, an EEG device 142, and/or MEG device 143) used to sense one or more physical characteristics (e.g., cerebral characteristic) of the authoring user 18, the data (e.g., as provided directly by the one or more sensors 48 or by the mental state inference module 106) indicative of the inferred mental state of the authoring user 18 being based, at least in part, on the one or more physical characteristics of the authoring user 18 sensed by the one or more sensors 48.

Figure 8B:
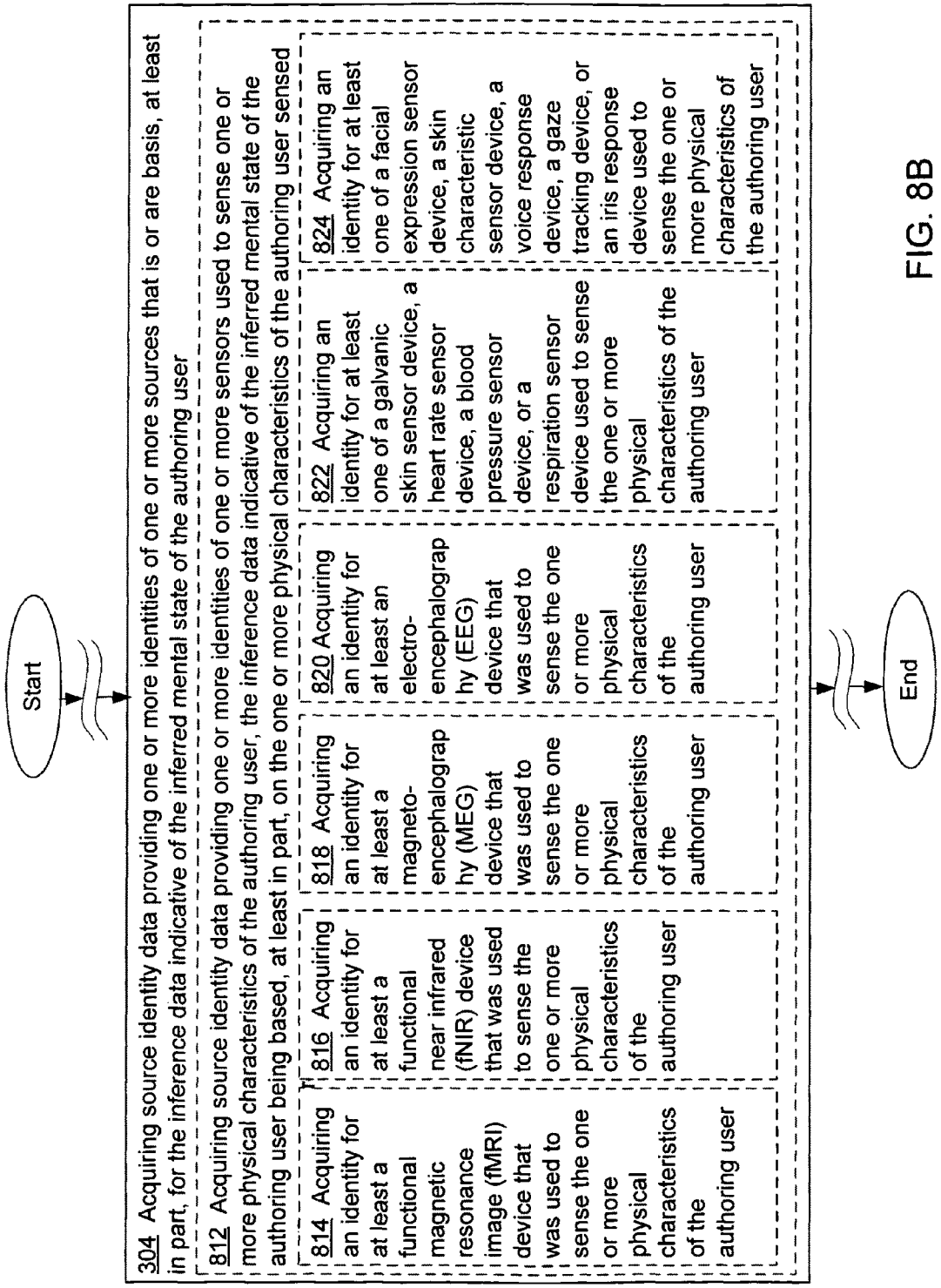
FIG. 8B is a high-level logic flowchart of a process depicting some more alternate implementations of the source identity acquisition operation 304 of FIG. 1.

In various implementations, operation 812 may include one or more additional operations as illustrated in FIG. 8B. For example, in some implementations, operation 812 may include an operation 814 for acquiring an identity for at least a functional magnetic resonance image (fMRI) device that was used to sense the one or more physical characteristics of the authoring user. For instance, the sensor identification (ID) acquisition module 204 of the authoring network device 10 acquiring an identity (e.g., sensor type or model number) for at least a functional magnetic resonance image (fMRI) device 140 that was used to sense the one or more physical characteristics (e.g., blood oxygen or blood volume changes of a brain) of the authoring user 18.

In some implementations, operation 812 may include an operation 816 for acquiring an identity for at least a functional near infrared (fNIR) device that was used to sense the one or more physical characteristics of the authoring user. For instance, the sensor identification (ID) acquisition module 204 of the authoring network device 10 acquiring from the memory 49 or from the one or more sensors 48 an identity (e.g., sensor type or model number) for at least a functional near infrared (fNIR) device 141 that was used to sense the one or more physical characteristics (e.g., blood oxygen or blood volume changes of a brain) of the authoring user 18.

In some implementations, operation 812 may include an operation 818 for acquiring an identity for at least a magnetoencephalography (MEG) device that was used to sense the one or more physical characteristics of the authoring user. For instance, the sensor identification (ID) acquisition module 204 of the authoring network device 10 acquiring from the memory 49 or from the one or more sensors 48 an identity (e.g., sensor type or model number) for at least a magnetoencephalography (MEG) device 143 that was used to sense the one or more physical characteristics (e.g., a cerebral characteristic including, for example, a characteristic associated with electrical activities of a brain) of the authoring user 18.

In some implementations, operation 812 may include an operation 820 for acquiring an identity for at least an electroencephalography (EEG) device that was used to sense the one or more physical characteristics of the authoring user. For instance, the sensor identification (ID) acquisition module 204 of the authoring network device 10 acquiring from the memory 49 or from the one or more sensors 48 an identity (e.g., sensor type or model number) for at least an electroencephalography (EEG) device 142 that was used to sense the one or more physical characteristics (e.g., a cerebral characteristic including, for example, a characteristic associated with electrical activities of a brain) of the authoring user 18.

In some implementations, operation 812 may include an operation 822 for acquiring an identity for at least one of a galvanic skin sensor device, heart rate sensor device, a blood pressure sensor device, or a respiration sensor device used to sense the one or more physical characteristics of the authoring user. For instance, the sensor identification (ID) acquisition module 204 of the authoring network device 10 acquiring from the memory 49 or from the one or more sensors 48 an identity (e.g., sensor type or model number) for at least one of a galvanic skin sensor device 144, a heart rate sensor device 145, a blood pressure sensor device 146, or a respiration sensor device 147 used to sense the one or more physical characteristics (e.g., heart rate, blood pressure, or respiration) of the authoring user 18.

In some implementations, operation 812 may include an operation 824 for acquiring an identity for at least one of a facial expression sensor device, a skin characteristic sensor device, a voice response device, a gaze tracking device, or an iris response device used to sense the one or more physical characteristics of the authoring user. For instance, the sensor identification (ID) acquisition module 204 of the authoring network device 10 acquiring from the memory 49 or from the one or more sensors 48 an identity (e.g., sensor type or model number) for at least one of a facial expression sensor device 148, a skin characteristic sensor device 149, a voice response device 150, a gaze tracking device 151, or an iris response device 152 used to sense the one or more physical characteristics (e.g., facial expression, skin characteristic, voice characteristic, eye movement, or iris characteristic) of the authoring user 18.

Figure 9A:
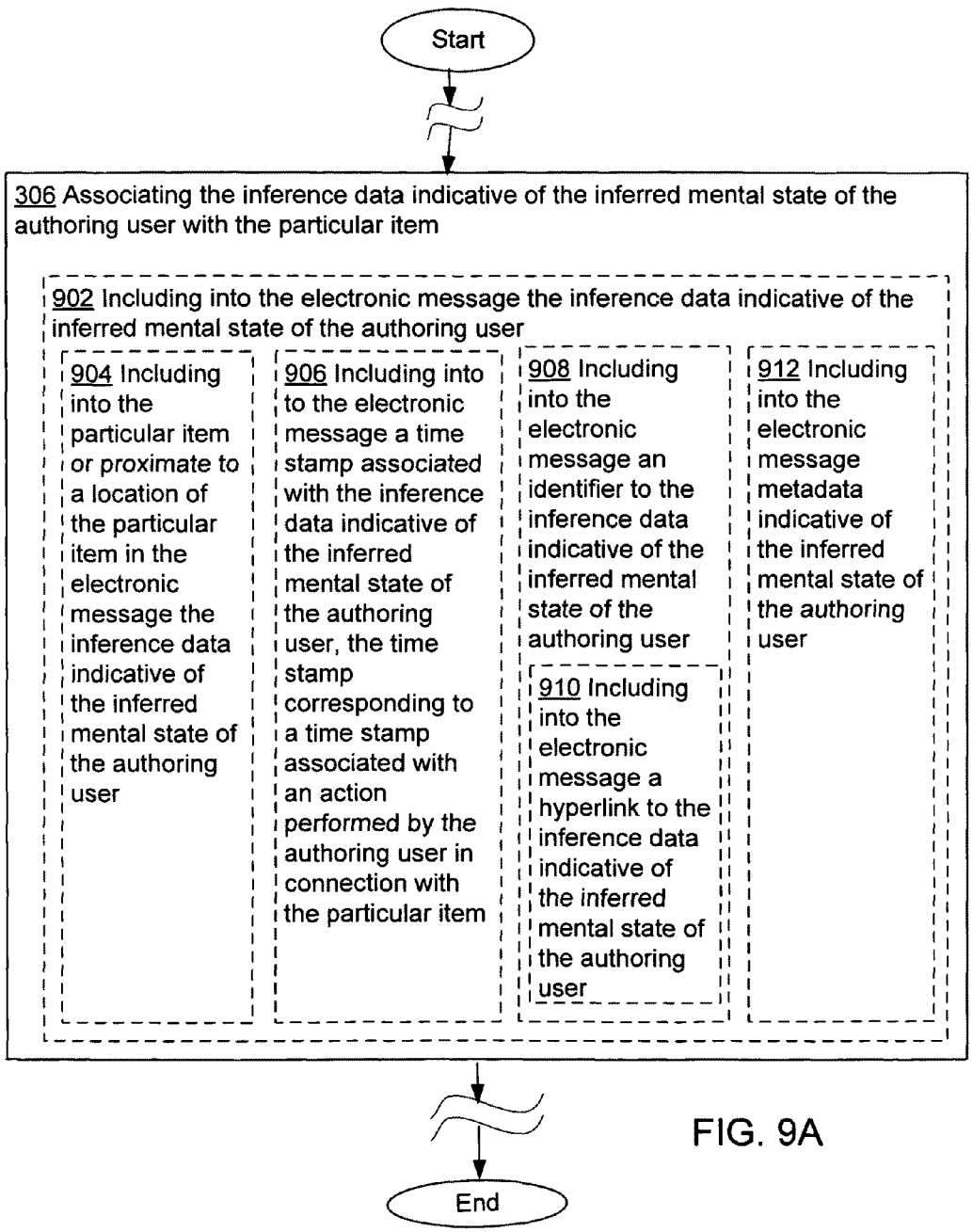
FIG. 9A is a high-level logic flowchart of a process depicting alternate implementations of the inference data association operation 306 of FIG. 3.

In various embodiments, the inference data association operation 306 depicted in FIG. 3 may include one or more additional operations. For example, in some embodiments, the inference data association operation 306 may include an inclusion operation 902 for including into the electronic message the inference data indicative of the inferred mental state of the authoring user as illustrated in FIG. 9A. For instance, the inference data inclusion module 110 of the authoring network device 10 including into the electronic message 20 (e.g., in the proximate location of the particular item 21, in the particular item 21 itself, or in other locations in the electronic message 21) the inference data indicative of the inferred mental state (e.g., state of anger, state of happiness, and so forth) of the authoring user 18. The inference data to be included may be in various forms including, for example, "raw" data provided by one or more sensors 48, data provided by a mental state inference module 106 that may directly identify an inferred mental state for the authoring user 18, or in some other form.

In some embodiments, operation 902 may further include one or more additional operations. For example, in some implementations, operation 902 may include an operation 904 for including into the particular item or proximate to a location of the particular item in the electronic message the inference data indicative of the inferred mental state of the authoring user as illustrated in FIG. 9A. For instance, the inference data inclusion module 110 of the authoring network device 10 including into the particular item 21 or proximate (e.g., nearby) to a location of the particular item 21 in the electronic message 20 the data (e.g., as acquired by the inference data acquisition module 30) indicative of the inferred mental state (e.g., state of frustration, state of approval or disapproval, state of trust, and so forth) of the authoring user 18.

In some implementations, operation 902 may include an operation 906 for including into to the electronic message a time stamp associated with the inference data indicative of the inferred mental state of the authoring user, the time stamp corresponding to a time stamp associated with an action performed by the authoring user in connection with the particular item as illustrated in FIG. 9A. For instance, the inference data inclusion module 110 of the authoring network device 10 including into to the electronic message 20 a time stamp (e.g., as provided by a time stamp module 125) associated with the inference data indicative of the inferred mental state (e.g., one or more of state of anger, state of distress, state of pain, and so forth) of the authoring user 18, the time stamp corresponding to a time stamp associated with an action (e.g., creating, modifying, deleting, and so forth) performed by the authoring user 18 in connection with the particular item 21.

In some implementations, operation 902 may include an operation 908 for including into the electronic message an identifier to the inference data indicative of the inferred mental state of the authoring user as illustrated in FIG. 9A. For instance, the inference data inclusion module 110 of the authoring network device 10 including into the electronic message 20 an identifier (e.g., a name, an address, a hyperlink, and so forth) to the inference data indicative of the inferred mental state (e.g., one or more of state of happiness, state of surprise, state of inattention, and so forth) of the authoring user 18.

In some implementations, operation 908 may further include an operation 910 for including into the electronic message a hyperlink to the inference data indicative of the inferred mental state of the authoring user as illustrated in FIG. 9A. For instance, the inference data inclusion module 110 of the authoring network device 10 including into the electronic message 20 a hyperlink to the inference data indicative of the inferred mental state (e.g., one or more of state of arousal, state of impatience, state of confusion, and so forth) of the authoring user 18.

In some implementations, operation 902 may include an operation 912 for including into the electronic message metadata indicative of the inferred mental state of the authoring user as illustrated in FIG. 9A. For instance, the inference data inclusion module 110 of the authoring network device 10 including into the electronic message 20 metadata indicative of the inferred mental state (e.g., one or more of state of distraction, state of overall mental activity, state of alertness, state of acuity, and so forth) of the authoring user 18.

Figure 9B:
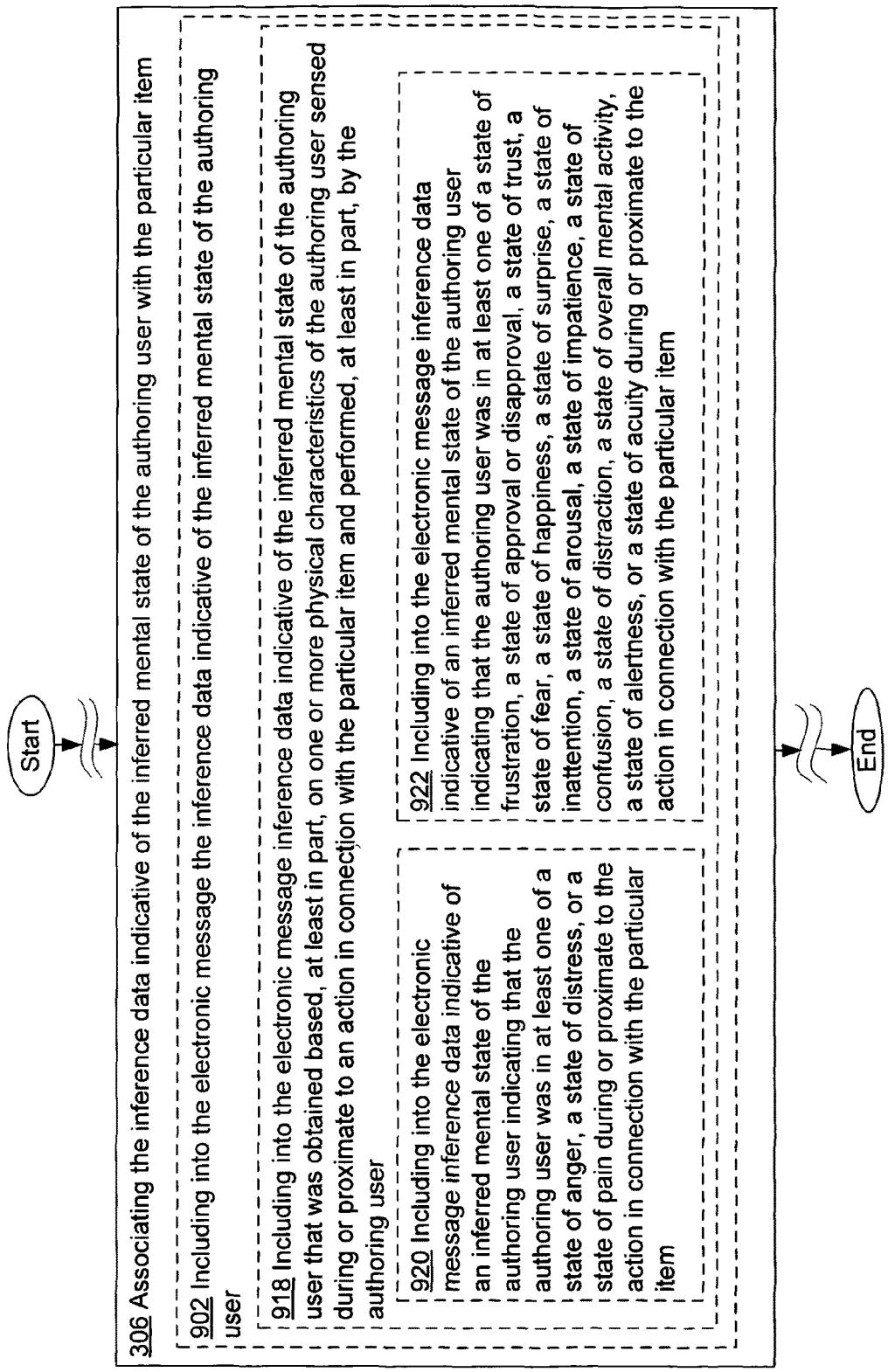
FIG. 9B is a high-level logic flowchart of a process depicting alternate implementations of the inclusion operation 902 of FIG. 9A.

In some implementations, operation 902 may include an operation 918 for including into the electronic message inference data indicative of the inferred mental state of the authoring user that was obtained based, at least in part, on one or more physical characteristics of the authoring user sensed during or proximate to an action in connection with the particular item and performed, at least in part, by the authoring user as illustrated in FIG. 9B. For instance, the inference data inclusion module 110 of the authoring network device 10 including into the electronic message 20 data (e.g., as provided by an inference data acquisition module 30 via a physical characteristic sensing module 108) indicative of the inferred mental state (e.g., one or more of state of anger, state of distress, state of pain, and so forth) of the authoring user 18 that was obtained based, at least in part, on one or more physical characteristics (e.g., cerebral, cardiopulmonary, or system physiological characteristic) of the authoring user 18 sensed (e.g., by a physical characteristic sensing module 108 via one or more sensors 48) during or proximate to an action (e.g., relocating, extracting, forwarding, and so forth) in connection with the particular item 21 and performed, at least in part, by the authoring user 18.

Operation 918 in various implementations my further include one or more additional operations as illustrated in FIGS. 9B to 9H. For instance, in some implementations, operation 918 may include an operation 920 for including into the electronic message inference data indicative of an inferred mental state of the authoring user indicating that the authoring user was in at least one of a state of anger, a state of distress, or a state of pain during or proximate to the action in connection with the particular item as illustrated in FIG. 9B. For instance, the inference data inclusion module 110 of the authoring network device 10 including into the electronic message 20 inference data indicative of an inferred mental state of the authoring user 18 (e.g., as provided by inference data acquisition module 30) indicating that the authoring user 18 was in at least one of a state of anger, a state of distress, or a state of pain during or proximate to the action (e.g., storing, activating or deactivating, tagging, and so forth) in connection with the particular item 21.

In some implementations, operation 918 may include an operation 922 for including into the electronic message inference data indicative of an inferred mental state of the authoring user indicating that the authoring user was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action in connection with the particular item as illustrated in FIG. 9B. For instance, the inference data inclusion module 110 of the authoring network device 10 including into the electronic message 20 inference data indicative of an inferred mental state of the authoring user 18 (e.g., as provided by inference data acquisition module 30) indicating that the authoring user 18 was in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity during or proximate to the action (e.g., associating, categorizing, substituting, inserting, and so forth) in connection with the particular item 21.

Figure 9C:
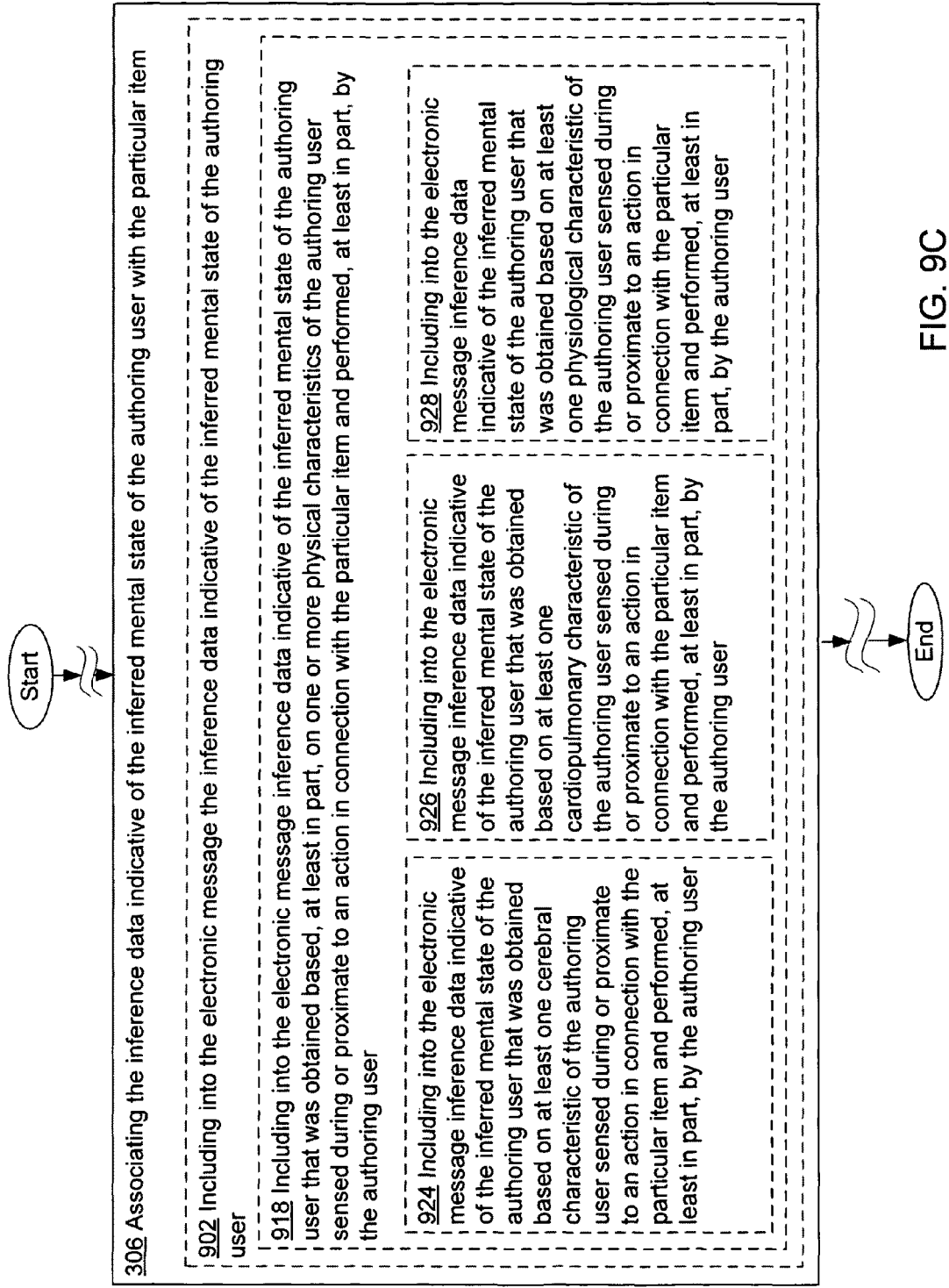
FIG. 9C is a high-level logic flowchart of a process depicting alternate implementations of the inclusion operation 918 of FIG. 9B.

In some implementations, operation 918 may include an operation 924 for including into the electronic message inference data indicative of the inferred mental state of the authoring user that was obtained based on at least one cerebral characteristic of the authoring user sensed during or proximate to an action in connection with the particular item and performed, at least in part, by the authoring user as illustrated in FIG. 9C. For instance, the inference data inclusion module 110 of the authoring network device 10 including into the electronic message 20 inference data indicative of the inferred mental state (e.g., state of anger, state of distress, state of pain, and so forth) of the authoring user 18 that was obtained (e.g., via inference data acquisition module 30) based on at least one cerebral characteristic (e.g., a characteristic associated with electrical activity of a brain) of the authoring user 18 sensed (e.g., via an EEG device 142 and/or an MEG device 143) during or proximate to an action (e.g., creating, modifying, deleting, and so forth) in connection with the particular item 21 and performed, at least in part, by the authoring user 18.

In some implementations, operation 918 may include an operation 926 for including into the electronic message inference data indicative of the inferred mental state of the authoring user that was obtained based on at least one cardiopulmonary characteristic of the authoring user sensed during or proximate to an action in connection with the particular item and performed, at least in part, by the authoring user as illustrated in FIG. 9C. For instance, the inference data inclusion module 110 of the authoring network device 10 including into the electronic message 20 inference data indicative of the inferred mental state (e.g., state of frustration, state of approval or disapproval, state of trust, and so forth) of the authoring user 18 that was obtained (e.g., via inference data acquisition module 30) based on at least one cardiopulmonary characteristic (e.g., heart rate) of the authoring user 18 sensed (e.g., via heart rate sensor device 145) during or proximate to an action (e.g., relocating, extracting, forwarding, and so forth) in connection with the particular item 21 and performed, at least in part, by the authoring user 18.

In some implementations, operation 918 may include an operation 928 for including into the electronic message inference data indicative of the inferred mental state of the authoring user that was obtained based on at least one systemic physiological characteristic of the authoring user sensed during or proximate to an action in connection with the particular item and performed, at least in part, by the authoring user as illustrated in FIG. 9C. For instance, the inference data inclusion module 110 of the authoring network device 10 including into the electronic message 20 inference data indicative of the inferred mental state (e.g., state of fear, state of happiness, state of surprise, and so forth) of the authoring user 18 that was obtained (e.g., via inference data acquisition module 30) based on at least one systemic physiological characteristic (e.g., blood pressure) of the authoring user 18 sensed (e.g., via a blood pressure sensor device 146) during or proximate to an action (e.g., storing, activating or deactivating, tagging, associating, and so forth) in connection with the particular item 21 and performed, at least in part, by the authoring user 18.

Figure 9D:
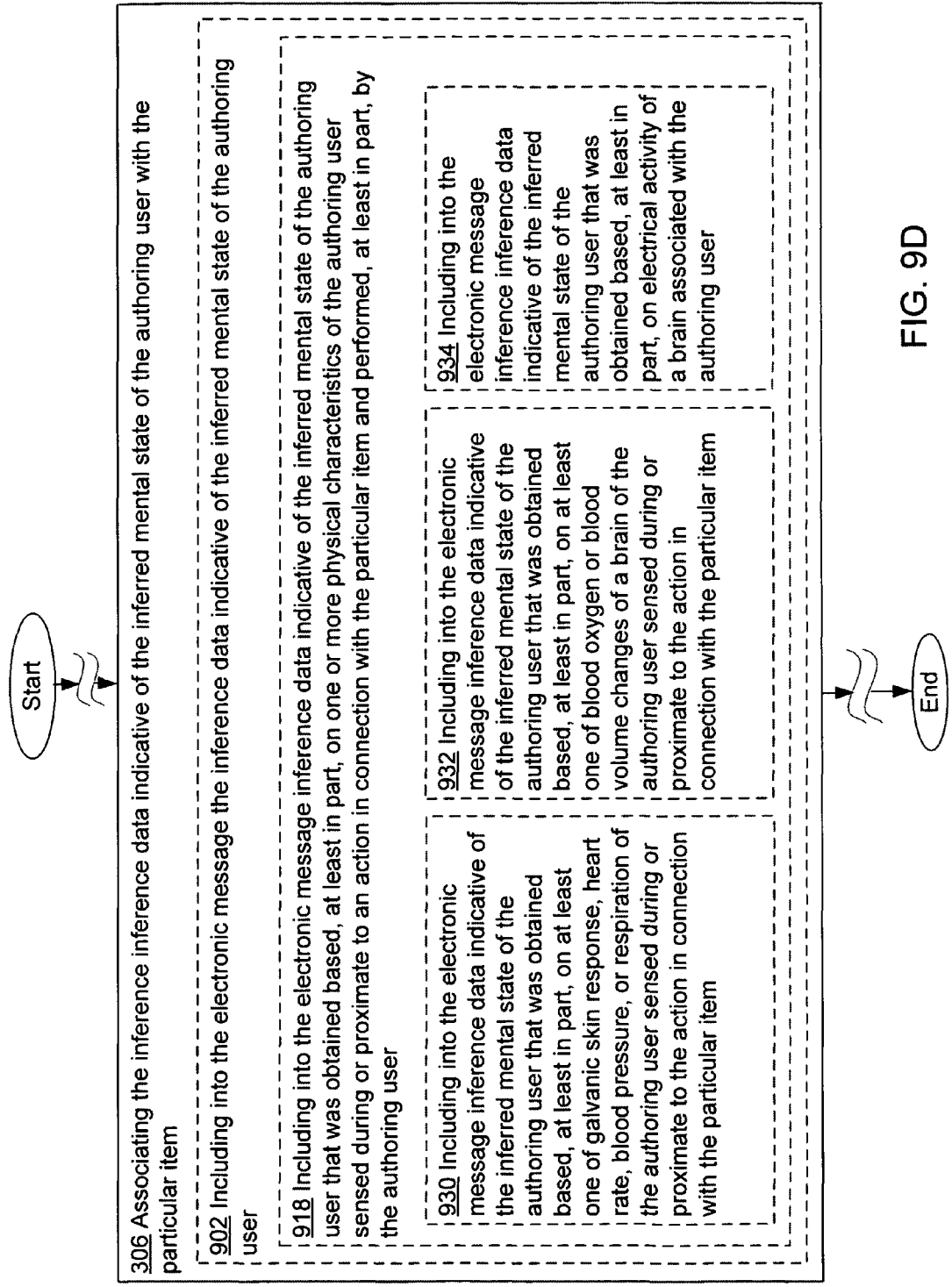
FIG. 9D is a high-level logic flowchart of a process depicting more alternate implementations of the inclusion operation 918 of FIG. 9B.

In some implementations, operation 918 may include an operation 930 for including into the electronic message inference data indicative of the inferred mental state of the authoring user that was obtained based, at least in part, on at least one of galvanic skin response, heart rate, blood pressure, or respiration of the authoring user sensed during or proximate to the action in connection with the particular item as illustrated in FIG. 9D. For instance, the inference data inclusion module 110 of the authoring network device 10 including into the electronic message 20 inference data indicative of the inferred mental state (e.g., state of inattention, state of arousal, state of impatience, state of confusion, and so forth) of the authoring user 18 that was obtained (e.g., via inference data acquisition module 30) based, at least in part, on at least one of galvanic skin response, heart rate, blood pressure, or respiration of the authoring user sensed (e.g., via a galvanic skin sensor device 144, heart rate sensor device 145, blood pressure sensor device 146, or respiration sensor device 147) during or proximate to the action (e.g., categorizing, substituting, inserting, and so forth) in connection with the particular item 21.

In some implementations, operation 918 may include an operation 932 for including into the electronic message inference data indicative of the inferred mental state of the authoring user that was obtained based, at least in part, on at least one of blood oxygen or blood volume changes of a brain of the authoring user sensed during or proximate to the action in connection with the particular item as illustrated in FIG. 9D. For instance, the inference data inclusion module 110 of the authoring network device 10 including into the electronic message 20 inference data indicative of the inferred mental state (e.g., state of distraction, state of overall mental activity, state of alertness, state of acuity, and so forth) of the authoring user 18 that was obtained (e.g., via inference data acquisition module 30) based, at least in part, on at least one of blood oxygen or blood volume changes of a brain of the authoring user 18 sensed (e.g., via an fMRI device 140 and/or an fNIR device 141) during or proximate to the action (e.g., creating, modifying, deleting, and so forth) in connection with the particular item 21.

In some implementations, operation 918 may include an operation 934 for including into the electronic message inference data indicative of the inferred mental state of the authoring user that was obtained based, at least in part, on electrical activity of a brain associated with the authoring user as illustrated in FIG. 9D. For instance, the inference data inclusion module 110 of the authoring network device 10 including into the electronic message 20 inference data indicative of the inferred mental state (e.g., state of anger, state of distress, state of pain, and so forth) of the authoring user 18 that was obtained (e.g., via inference data acquisition module 30) based, at least in part, on electrical activity of a brain (e.g., as sensed by EEG device 142) associated with the authoring user 18.

In some implementations, operation 918 may include an operation 936 for including into the electronic message inference data indicative of the inferred mental state of the authoring user that was obtained based, at least in part, on at least one of facial expression, skin characteristic, voice characteristic, eye movement, or iris dilation of the authoring user sensed during or proximate to the action in connection with the particular item as illustrated in FIG. 9E. For instance, the inference data inclusion module 110 of the authoring network device 10 including into the electronic message 20 inference data indicative of the inferred mental state (e.g., state of happiness, state of surprise, state of inattention, and so forth) of the authoring user 18 that was obtained (e.g., via inference data acquisition module 30) based, at least in part, on at least one of facial expression, skin characteristic, voice characteristic, eye movement, or iris dilation of the authoring user 18 sensed (e.g., via facial expression sensor device 148, skin characteristic sensor device 149, voice response device 150, gaze tracking device 151, and/or iris response device 152) during or proximate to the action (e.g., creating, modifying, deleting, and so forth) in connection with the particular item 21.

In some implementations, operation 918 may include an operation 938 for including into the electronic message inference data indicative of the inferred mental state of the authoring user that was obtained based, at least in part, on data obtained in response to a functional magnetic resonance imaging procedure or a functional near infrared procedure performed on the authoring user during or proximate to the action in connection with the particular item as illustrated in FIG. 9E. For instance, the inference data inclusion module 110 of the authoring network device 10 including into the electronic message 20 inference data indicative of the inferred mental state (e.g., state of arousal, state impatience, state of confusion, and so forth) of the authoring user 18 that was obtained (e.g., via inference data acquisition module 30) based, at least in part, on data obtained in response to a functional magnetic resonance imaging procedure (e.g., using an fMRI device 140) or a functional near infrared procedure (e.g., using an fNIR device 141) performed on the authoring user 18 during or proximate to the action (e.g., creating, modifying, deleting, and so forth) in connection with the particular item 21.

In some implementations, operation 918 may include an operation 940 for including into the electronic message inference data indicative of the inferred mental state of the authoring user that was obtained based, at least in part, on data obtained in response to a magnetoencephalography (MEG) procedure or an electroencephalography (EEG) procedure performed on the authoring user during or proximate to the action in connection with the particular item as illustrated in FIG. 9E. For instance, the inference data inclusion module 110 of the authoring network device 10 including into the electronic message 20 inference data indicative of the inferred mental state (e.g., state of distraction, state of overall mental activity, state of alertness, state of acuity, and so forth) of the authoring user 18 that was obtained (e.g., via inference data acquisition module 30) based, at least in part, on data obtained in response to a magnetoencephalography (MEG) procedure (e.g., using an MEG device 143) or an electroencephalography (EEG) procedure (e.g., using an EEG device 142) performed on the authoring user 18 during or proximate to the action (e.g., creating, modifying, deleting, and so forth) in connection with the particular item 21.

Figure 9F:
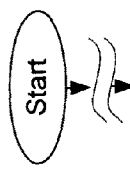
FIG. 9F is a high-level logic flowchart of a process depicting more alternate implementations of the inclusion operation 918 of FIG. 9B.
Figure 9F:
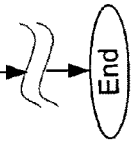
Figure 9G:
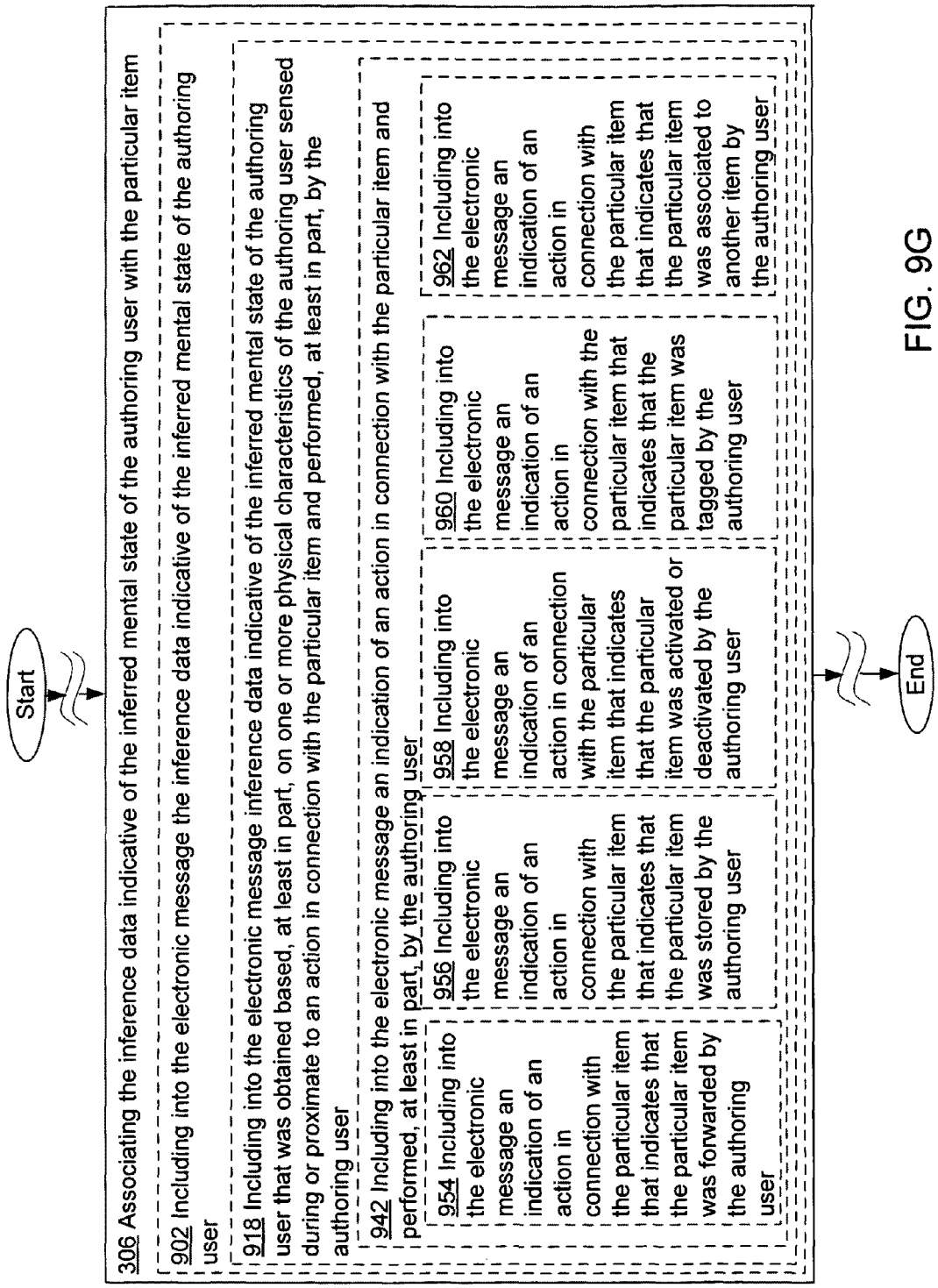
FIG. 9G is a high-level logic flowchart of a process depicting more alternate implementations of the inclusion operation 918 of FIG. 9B.
Figure 9H:
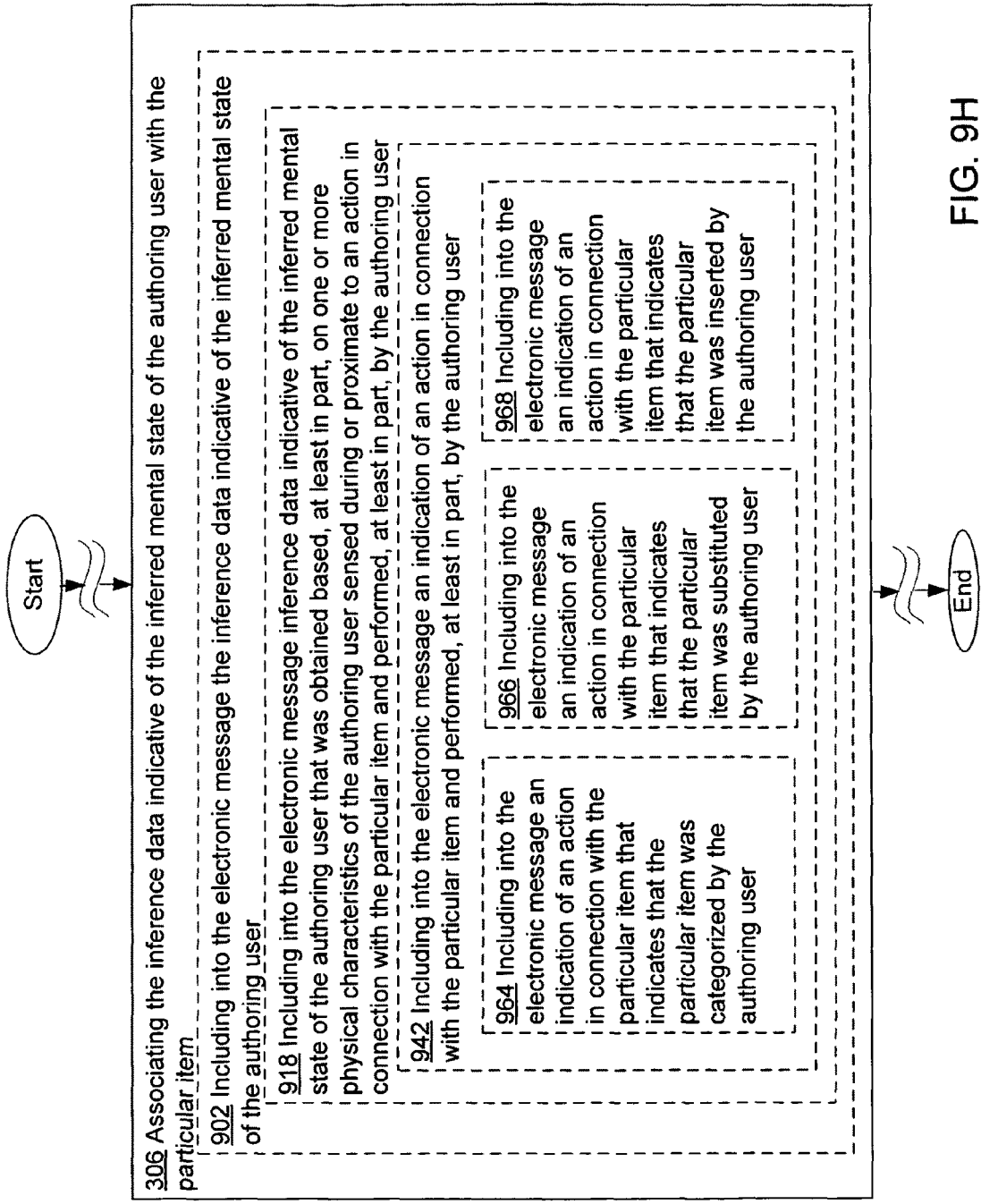
FIG. 9H is a high-level logic flowchart of a process depicting more alternate implementations of the inclusion operation 918 of FIG. 9B.

In some implementations, operation 918 may include an operation 942 for including into the electronic message an indication of an action in connection with the particular item and performed, at least in part, by the authoring user as illustrated in FIGS. 9F to 9H. For instance, the inference data inclusion module 110 of the authoring network device 10 including into the electronic message 20 an indication (e.g., as provided by an action module 34) of an action (e.g., creating, modifying, deleting, and so forth) in connection with the particular item 21 and performed, at least in part, by the authoring user 18.

In various implementations, operation 942 may include one or more additional operations. For example, in some implementations, operation 942 may include an operation 944 for including into the electronic message an indication of an action in connection with the particular item that indicates that the particular item was created by the authoring user as illustrated in FIG. 9F. For instance, the inference data inclusion module 110 of the authoring network device 10 including into the electronic message 20 an indication of an action (e.g., as provided by an action module 34) in connection with the particular item 21 that indicates that the particular item 21 was created (e.g., via a creation module 112) by the authoring user 18.

In some implementations, operation 942 may include an operation 946 for including into the electronic message an indication of an action in connection with the particular item that indicates that the particular item was modified by the authoring user as illustrated in FIG. 9F. For instance, the inference data inclusion module 110 of the authoring network device 10 including into the electronic message 20 an indication of an action (e.g., as provided by an action module 34) in connection with the particular item 21 that indicates that the particular item 21 was modified (e.g., via a modification module 113) by the authoring user 18.

In some implementations, operation 942 may include an operation 948 for including into the electronic message an indication of an action in connection with the particular item that indicates that the particular item was deleted by the authoring user as illustrated in FIG. 9F. For instance, the inference data inclusion module 110 of the authoring network device 10 including into the electronic message 20 an indication of an action (e.g., as provided by an action module 34) in connection with the particular item 21 that indicates that the particular item 21 was deleted (e.g., via a deletion module 114) by the authoring user 18.

In some implementations, operation 942 may include an operation 950 for including into the electronic message an indication of an action in connection with the particular item that indicates that the particular item was relocated in the electronic message by the authoring user as illustrated in FIG. 9F. For instance, the inference data inclusion module 110 of the authoring network device 10 including into the electronic message 20 an indication of an action (e.g., as provided by an action module 34) in connection with the particular item 21 that indicates that the particular item 21 was relocated (e.g., via a relocation module 115) in the electronic message 20 by the authoring user 18.

In some implementations, operation 942 may include an operation 952 for including into the electronic message an indication of an action in connection with the particular item that indicates that the particular item was extracted by the authoring user as illustrated in FIG. 9F. For instance, the inference data inclusion module 110 of the authoring network device 10 including into the electronic message 20 an indication of an action (e.g., as provided by an action module 34) in connection with the particular item 21 that indicates that the particular item 21 was extracted (e.g., via an extraction module 116) by the authoring user 18.

In some implementations, operation 942 may include an operation 954 for including into the electronic message an indication of an action in connection with the particular item that indicates that the particular item was forwarded by the authoring user as illustrated in FIG. 9G. For instance, the inference data inclusion module 110 of the authoring network device 10 including into the electronic message 20 an indication of an action (e.g., as provided by an action module 34) in connection with the particular item 21 that indicates that the particular item 21 was forwarded (e.g., via a forwarding module 117) by the authoring user 18.

In some implementations, operation 942 may include an operation 956 for including into the electronic message an indication of an action in connection with the particular item that indicates that the particular item was stored by the authoring user as illustrated in FIG. 9G. For instance, the inference data inclusion module 110 of the authoring network device 10 including into the electronic message 20 an indication of an action (e.g., as provided by an action module 34) in connection with the particular item 21 that indicates that the particular item 21 was stored (e.g., via a storing module 118) into, for example, memory 49 by the authoring user 18.

In some implementations, operation 942 may include an operation 958 for including into the electronic message an indication of an action in connection with the particular item that indicates that the particular item was activated or deactivated by the authoring user as illustrated in FIG. 9G. For instance, the inference data inclusion module 110 of the authoring network device 10 including into the electronic message 20 an indication of an action (e.g., as provided by an action module 34) in connection with the particular item 21 that indicates that the particular item 21 was activated or deactivated (e.g., via an activating and deactivating module 119) by the authoring user 18.

In some implementations, operation 942 may include an operation 960 for including into the electronic message an indication of an action in connection with the particular item that indicates that the particular item was tagged by the authoring user as illustrated in FIG. 9G. For instance, the inference data inclusion module 110 of the authoring network device 10 including into the electronic message 20 an indication of an action (e.g., as provided by an action module 34) in connection with the particular item 21 that indicates that the particular item 21 was tagged (e.g., via a tagging module 120) by the authoring user 18.

In some implementations, operation 942 may include an operation 962 for including into the electronic message an indication of an action in connection with the particular item that indicates that the particular item was associated to another item by the authoring user as illustrated in FIG. 9G. For instance, the inference data inclusion module 110 of the authoring network device 10 including into the electronic message 20 an indication of an action (e.g., as provided by an action module 34) in connection with the particular item 21 that indicates that the particular item 21 was associated (e.g., via an associating module 121) to another item (e.g., which may or may not be external to the electronic message 20) by the authoring user 18.

In some implementations, operation 942 may include an operation 964 for including into the electronic message an indication of an action in connection with the particular item that indicates that the particular item was categorized by the authoring user as illustrated in FIG. 9H. For instance, the inference data inclusion module 110 of the authoring network device 10 including into the electronic message 20 an indication of an action (e.g., as provided by an action module 34) in connection with the particular item 21 that indicates that the particular item 21 was categorized (e.g., via a categorizing module 122) by the authoring user 18.

In some implementations, operation 942 may include an operation 966 for including into the electronic message an indication of an action in connection with the particular item that indicates that the particular item was substituted by the authoring user as illustrated in FIG. 9H. For instance, the inference data inclusion module 110 of the authoring network device 10 including into the electronic message 20 an indication of an action (e.g., as provided by an action module 34) in connection with the particular item 21 that indicates that the particular item 21 was substituted (e.g., via a substituting module 123) by the authoring user 18.

In some implementations, operation 942 may include an operation 968 for including into the electronic message an indication of an action in connection with the particular item that indicates that the particular item was inserted by the authoring user as illustrated in FIG. 9H. For instance, the inference data inclusion module 110 of the authoring network device 10 including into the electronic message 20 an indication of an action (e.g., as provided by an action module 34) in connection with the particular item 21 that indicates that the particular item 21 was inserted (e.g., via an inserting module 124) by the authoring user 18.

Figure 10A:
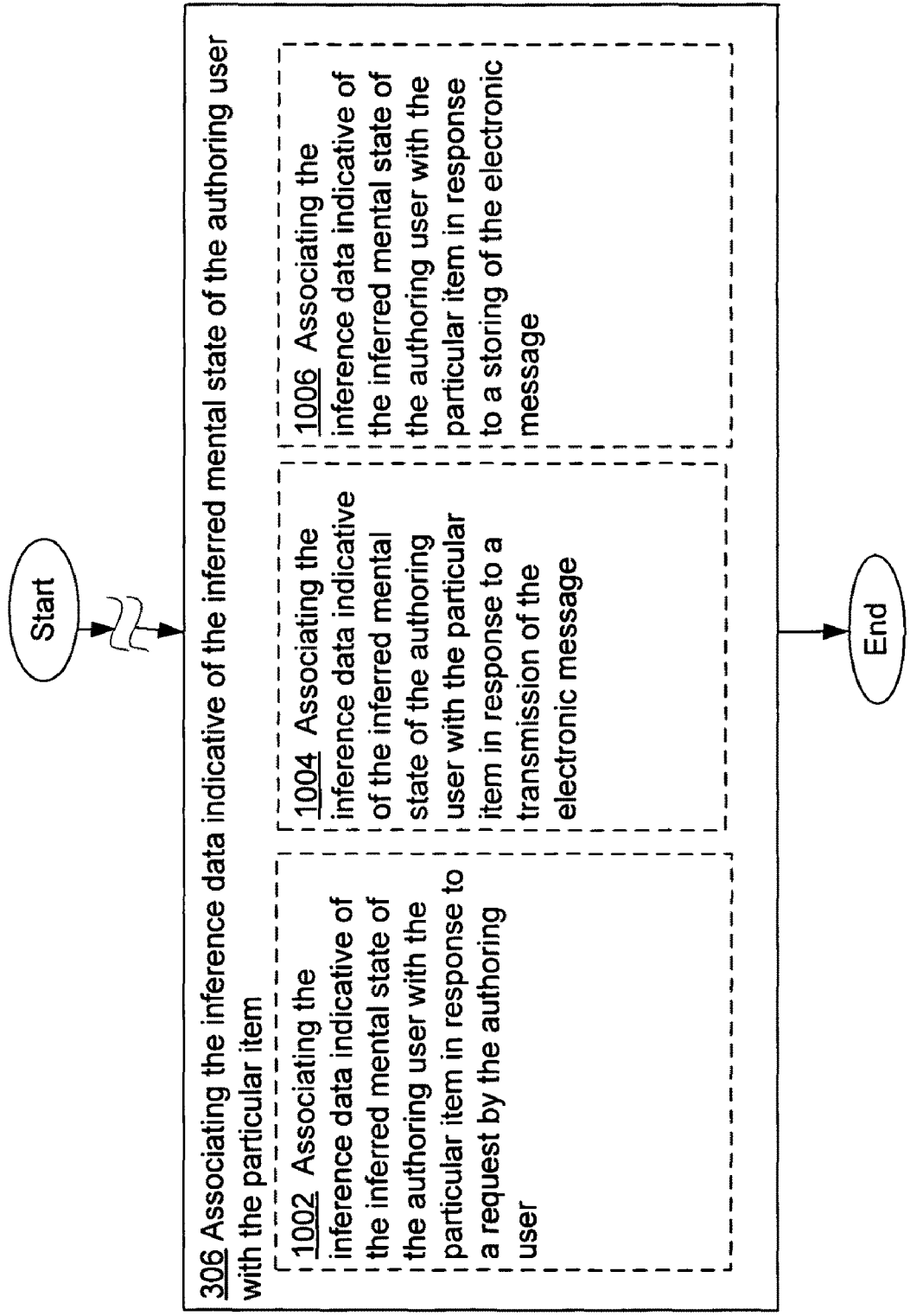
FIG. 10A is a high-level logic flowchart of a process depicting more alternate implementations of the inference data association operation 306 of FIG. 3.

The inference data association operation 306 of FIG. 3 may further include other additional or alternative operations in various alternative embodiments. For example, the inference data association operation 306 in some implementations may include an operation 1002 for associating the inference data indicative of the inferred mental state of the authoring user with the particular item in response to a request by the authoring user as illustrated in FIG. 10A. For instance, the inference data association module 32 of the authoring network device 10 associating (e.g., by including into the electronic message 20) the data (e.g., as provided by an inference data acquisition module 30) indicative of the inferred mental state (e.g., state of anger, state of distress, state of pain, and so forth) of the authoring user 18 with the particular item 21 in response to a request (e.g., as provided through a user interface 44) by the authoring user 18.

In some implementations, the inference data association operation 306 may include an operation 1004 for associating the inference data indicative of the inferred mental state of the authoring user with the particular item in response to a transmission of the electronic message as illustrated in FIG. 10A. For instance, the inference data association module 32 of the authoring network device 10 associating (e.g., by including into the electronic message 20) the inference data (e.g., as provided by an inference data acquisition module 30) indicative of the inferred mental state (e.g., state of frustration, state of approval or disapproval, state of trust, and so forth) of the authoring user 18 with the particular item 21 in response to a transmission of the electronic message 20.

In some implementations, the inference data association operation 306 may include an operation 1006 for associating the inference data indicative of the inferred mental state of the authoring user with the particular item in response to a storing of the electronic message as illustrated in FIG. 10A. For instance, the inference data association module 32 of the authoring network device 10 associating (e.g., by including into the electronic message 20) the inference data (e.g., as provided by an inference data acquisition module 30) indicative of the inferred mental state (e.g., state of fear, state of happiness, state of surprise, and so forth) of the authoring user 18 with the particular item 21 in response to a storing (e.g., in memory 49 or in a network server) of the electronic message 20.

Figure 10C:
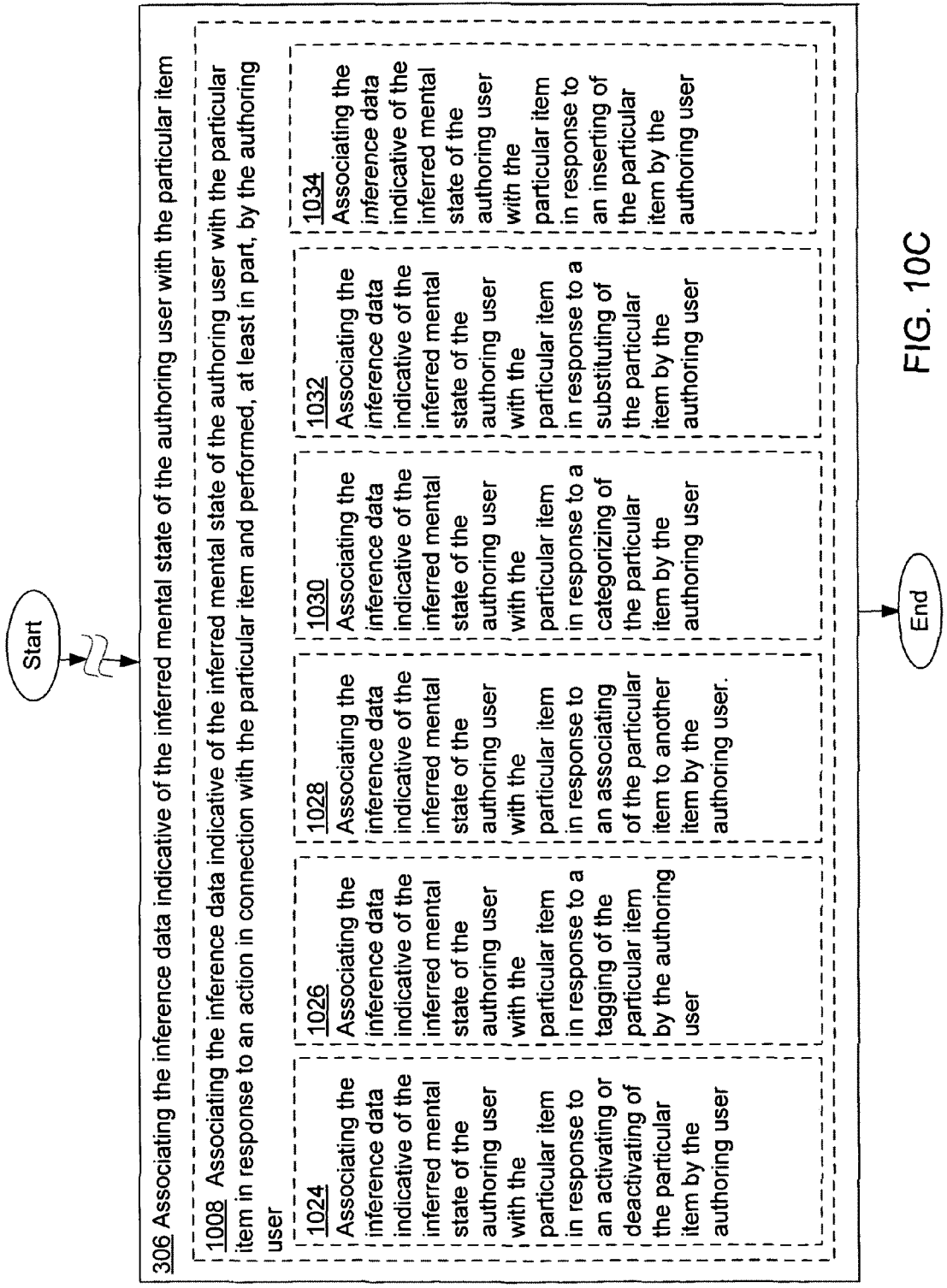
FIG. 10C is a high-level logic flowchart of a process depicting some more alternate implementations of the inference data association operation 306 of FIG. 3.

In some implementations, the inference data association operation 306 may include an operation 1008 for associating the inference data indicative of the inferred mental state of the authoring user with the particular item in response to an action in connection with the particular item and performed, at least in part, by the authoring user as illustrated in FIGS. 10B and 10C. For instance, the inference data association module 32 of the authoring network device 10 associating (e.g., by including into the electronic message 20) the inference data (e.g., as provided by an inference data acquisition module 30) indicative of the inferred mental state (e.g., state of inattention, state of arousal, state of impatience, and so forth) of the authoring user 18 with the particular item 21 in response to an action (e.g., creating, modifying, deleting, and so forth) in connection with the particular item 21 and performed, at least in part, by the authoring user 18 (e.g., via an action module 34).

In various embodiments, operation 1008 may include one or more additional operations as illustrated in FIGS. 10B and 10C. For example, in some implementations, operation 1008 may include an operation 1010 for associating the inference data indicative of the inferred mental state of the authoring user with the particular item in response to a creating of the particular item by the authoring user as illustrated in FIG. 10B. For instance, the inference data association module 32 of the authoring network device 10 associating the inference data (e.g., as provided by an inference data acquisition module 30) indicative of the inferred mental state (e.g., state of confusion, state of distraction, state of overall mental activity, state of alertness, state of acuity, and so forth) of the authoring user 18 with the particular item 21 in response to a creating (e.g., via a creation module 112) of the particular item 21 by the authoring user 18.

In some implementations, operation 1008 may include an operation 1012 for associating the inference data indicative of the inferred mental state of the authoring user with the particular item in response to a modifying of the particular item by the authoring user as illustrated in FIG. 9B. For instance, the inference data association module 32 of the authoring network device 10 associating the inference data (e.g., as provided by an inference data acquisition module 30) indicative of the inferred mental state (e.g., state of anger, state of distress, state of pain, and so forth) of the authoring user 18 with the particular item 21 in response to a modifying (e.g., via a modification module 113) of the particular item 21 by the authoring user 18.

In some implementations, operation 1008 may include an operation 1014 for associating the inference data indicative of the inferred mental state of the authoring user with the particular item in response to a deleting of the particular item by the authoring user as illustrated in FIG. 10B. For instance, the inference data association module 32 of the authoring network device 10 associating the inference data (e.g., as provided by an inference data acquisition module 30) indicative of the inferred mental state (e.g., state of frustration, state of approval or disapproval, state of trust, and so forth) of the authoring user 18 with the particular item 21 in response to a deleting (e.g., via a deletion module 114) of the particular item 21 by the authoring user 18.

In some implementations, operation 1008 may include an operation 1016 for associating the inference data indicative of the inferred mental state of the authoring user with the particular item in response to a relocating of the particular item in the electronic message by the authoring user as illustrated in FIG. 10B. For instance, the inference data association module 32 of the authoring network device 10 associating the inference data (e.g., as provided by an inference data acquisition module 30) indicative of the inferred mental state (e.g., state of fear, state of happiness, state of surprise, and so forth) of the authoring user 18 with the particular item 21 in response to a relocating (e.g., via a relocation module 115) of the particular item 21 in the electronic message 20 by the authoring user 18.

In some implementations, operation 1008 may include an operation 1018 for associating the inference data indicative of the inferred mental state of the authoring user with the particular item in response to an extracting of the particular item by the authoring user as illustrated in FIG. 10B. For instance, the inference data association module 32 of the authoring network device 10 associating the inference data (e.g., as provided by an inference data acquisition module 30) indicative of the inferred mental state (e.g., state of inattention, state of arousal, state of impatience, and so forth) of the authoring user 18 with the particular item 21 in response to an extracting (e.g., via an extraction module 116) of the particular item 21 by the authoring user 18.

In some implementations, operation 1008 may include an operation 1020 for associating the inference data indicative of the inferred mental state of the authoring user with the particular item in response to a forwarding of the particular item by the authoring user as illustrated in FIG. 10B. For instance, the inference data association module 32 of the authoring network device 10 associating the inference data (e.g., as provided by an inference data acquisition module 30) indicative of the inferred mental state (e.g., state of confusion, state of distraction, state of overall mental activity, state of alertness, state of acuity, and so forth) of the authoring user 18 with the particular item 21 in response to a forwarding (e.g., via a forwarding module 117) of the particular item 21 by the authoring user 18.

In some implementations, operation 1008 may include an operation 1022 for associating the inference data indicative of the inferred mental state of the authoring user with the particular item in response to a storing of the particular item by the authoring user as illustrated in FIG. 10B. For instance, the inference data association module 32 of the authoring network device 10 associating the inference data (e.g., as provided by an inference data acquisition module 30) indicative of the inferred mental state (e.g., state of anger, state of distress, state of pain, and so forth) of the authoring user 18 with the particular item 21 in response to a storing (e.g., via a storing module 118) of the particular item 21 by the authoring user 18.

In some implementations, operation 1008 may include an operation 1024 for associating the inference data indicative of the inferred mental state of the authoring user with the particular item in response to an activating or deactivating of the particular item by the authoring user as illustrated in FIG. 10C. For instance, the inference data association module 32 of the authoring network device 10 associating the inference data (e.g., as provided by an inference data acquisition module 30) indicative of the inferred mental state (e.g., state of frustration, state of approval or disapproval, state of trust, and so forth) of the authoring user 18 with the particular item 21 in response to an activating or deactivating (e.g., via an activating and deactivating module 119) of the particular item 21 by the authoring user 18.

In some implementations, operation 1008 may include an operation 1026 for associating the inference data indicative of the inferred mental state of the authoring user with the particular item in response to a tagging of the particular item by the authoring user as illustrated in FIG. 10C. For instance, the inference data association module 32 of the authoring network device 10 associating the inference data (e.g., as provided by an inference data acquisition module 30) indicative of the inferred mental state (e.g., state of fear, state of happiness, state of surprise, and so forth) of the authoring user 18 with the particular item 21 in response to a tagging (e.g., via a tagging module 120) of the particular item 21 by the authoring user 18.

In some implementations, operation 1008 may include an operation 1028 for associating the inference data indicative of the inferred mental state of the authoring user with the particular item in response to an associating of the particular item to another item by the authoring user as illustrated in FIG. 10C. For instance, the inference data association module 32 of the authoring network device 10 associating the inference data (e.g., as provided by an inference data acquisition module 30) indicative of the inferred mental state (e.g., state of inattention, state of arousal, state of impatience, and so forth) of the authoring user 18 with the particular item 21 in response to an associating (e.g., via an associating module 121) of the particular item 21 to another item (e.g., which may or may not be external to the electronic message 20) by the authoring user 18.

In some implementations, operation 1008 may include an operation 1030 for associating the inference data indicative of the inferred mental state of the authoring user with the particular item in response to a categorizing of the particular item by the authoring user as illustrated in FIG. 10C. For instance, the inference data association module 32 of the authoring network device 10 associating the inference data (e.g., as provided by an inference data acquisition module 30) indicative of the inferred mental state (e.g., state of confusion, state of distraction, state of overall mental activity, state of alertness, state of acuity, and so forth) of the authoring user 18 with the particular item 21 in response to a categorizing (e.g., via a categorizing module 122) of the particular item 21 by the authoring user 18.

In some implementations, operation 1008 may include an operation 1032 for associating the inference data indicative of the inferred mental state of the authoring user with the particular item in response to a substituting of the particular item by the authoring user as illustrated in FIG. 10C. For instance, the inference data association module 32 of the authoring network device 10 associating the inference data (e.g., as provided by an inference data acquisition module 30) indicative of the inferred mental state (e.g., state of anger, state of distress, state of pain, and so forth) of the authoring user 18 with the particular item 21 in response to a substituting (e.g., via a substituting module 123) of the particular item 21 by the authoring user 18.

In some implementations, operation 1008 may include an operation 1034 for associating the inference data indicative of the inferred mental state of the authoring user with the particular item in response to an inserting of the particular item by the authoring user as illustrated in FIG. 10C. For instance, the inference data association module 32 of the authoring network device 10 associating the inference data (e.g., as provided by an inference data acquisition module 30) indicative of the inferred mental state (e.g., state of frustration, state of approval or disapproval, state of trust, and so forth) of the authoring user 18 with the particular item 21 in response to an inserting (e.g., via an inserting module 124) of the particular item 21 by the authoring user 18.

In various alternative embodiments, the association of the inference data indicative of the inferred mental state of the authoring user 18 with the particular item 21 may be in response to other actions (which may be directly or indirectly connected to the particular item 21) other than those described above (e.g., creating, deleting, modifying, and so forth in connection with the particular item 21). For instance, in some alternative implementations, the association of the inference data indicative of the inferred mental state of the authoring user 18 with the particular item 21 (e.g., as performed by the inference data association module 32 of the authoring network device 10) may be in response to a searching operation (e.g., in order to find particular information on the Internet) initiated by the authoring user 18 and that may have been prompted while accessing the particular item 21. Other actions that may cause the inference data (i.e., inference data indicative of the inferred mental state of the authoring user 18) to be associated with particular item 21 may include, for example, particular movements of a user interface device (e.g., mouse) or other types of inputs received from other user interface devices.

Figure 11A:
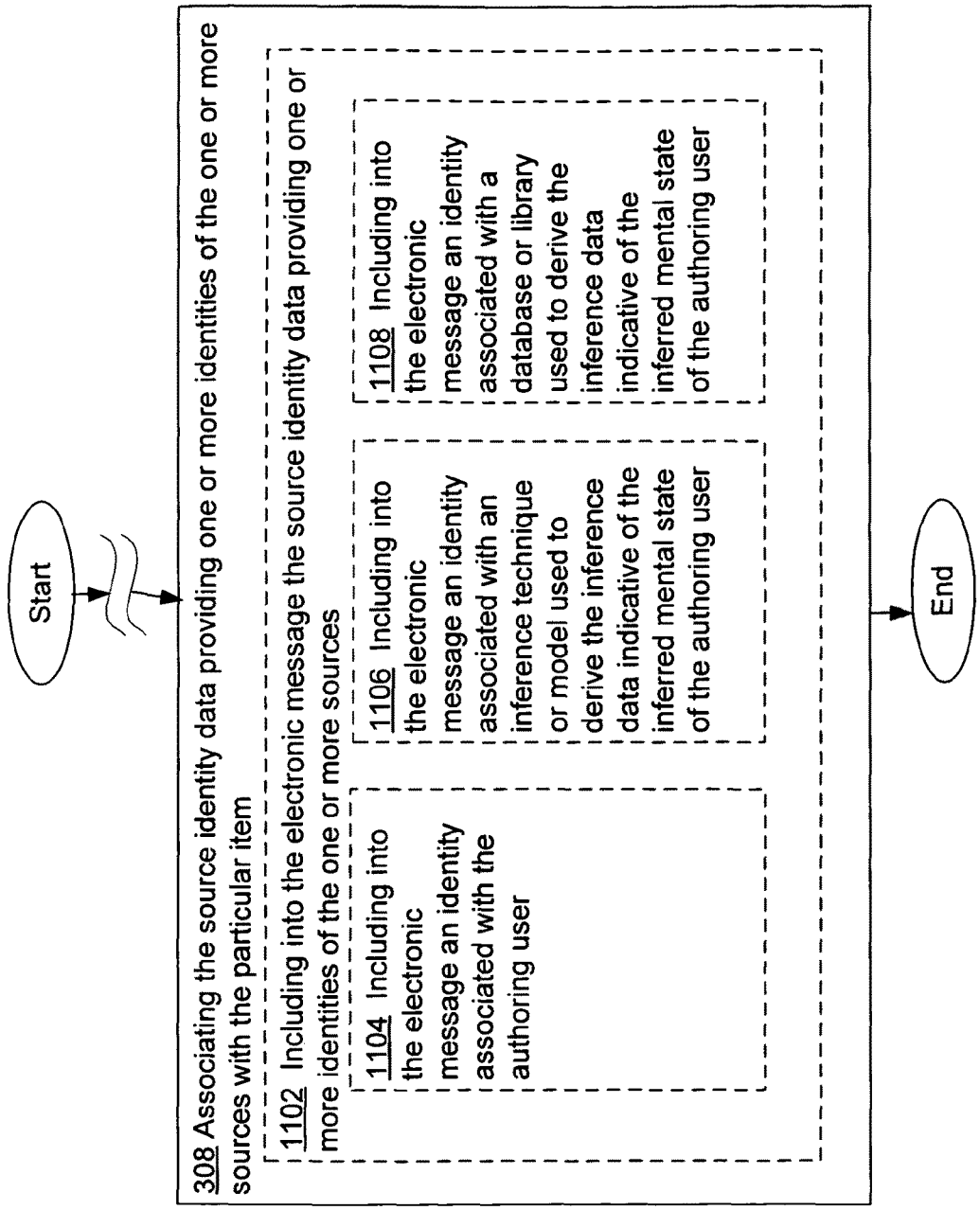
FIG. 11A is a high-level logic flowchart of a process depicting alternate implementations of the source identity association operation 308 of FIG. 3.

In various embodiments, the source identity association operation 308 of FIG. 3 may include one or more additional operations. For example, in some implementations, in order to associate source identity data providing one or more identities of the one or more sources to the particular item, the source identity association operation 308 may include an operation 1102 for including into the electronic message the source identity data providing one or more identities of the one or more sources as illustrated in FIG. 11A. For instance, the source identity inclusion module 111 of the authoring network device 10 including into the electronic message 20 the source identity data providing one or more identities (e.g., names, model numbers or identifiers, source types, hyperlinks, addresses, and/or other types of identifiers) of the one or more sources (e.g., one or more sensors 48). Note that in some alternative implementations the source identity association operation 308 may associate the source identity data providing one or more identities of the one or more sources with the particular item 21 without having to include the identities of the one or more sources into the electronic message 20. For example, in some implementations, the linking of the identities of the one or more sources may be included in a separate electronic message other than in the electronic message 20 that includes the particular item 21.

Figure 11B:
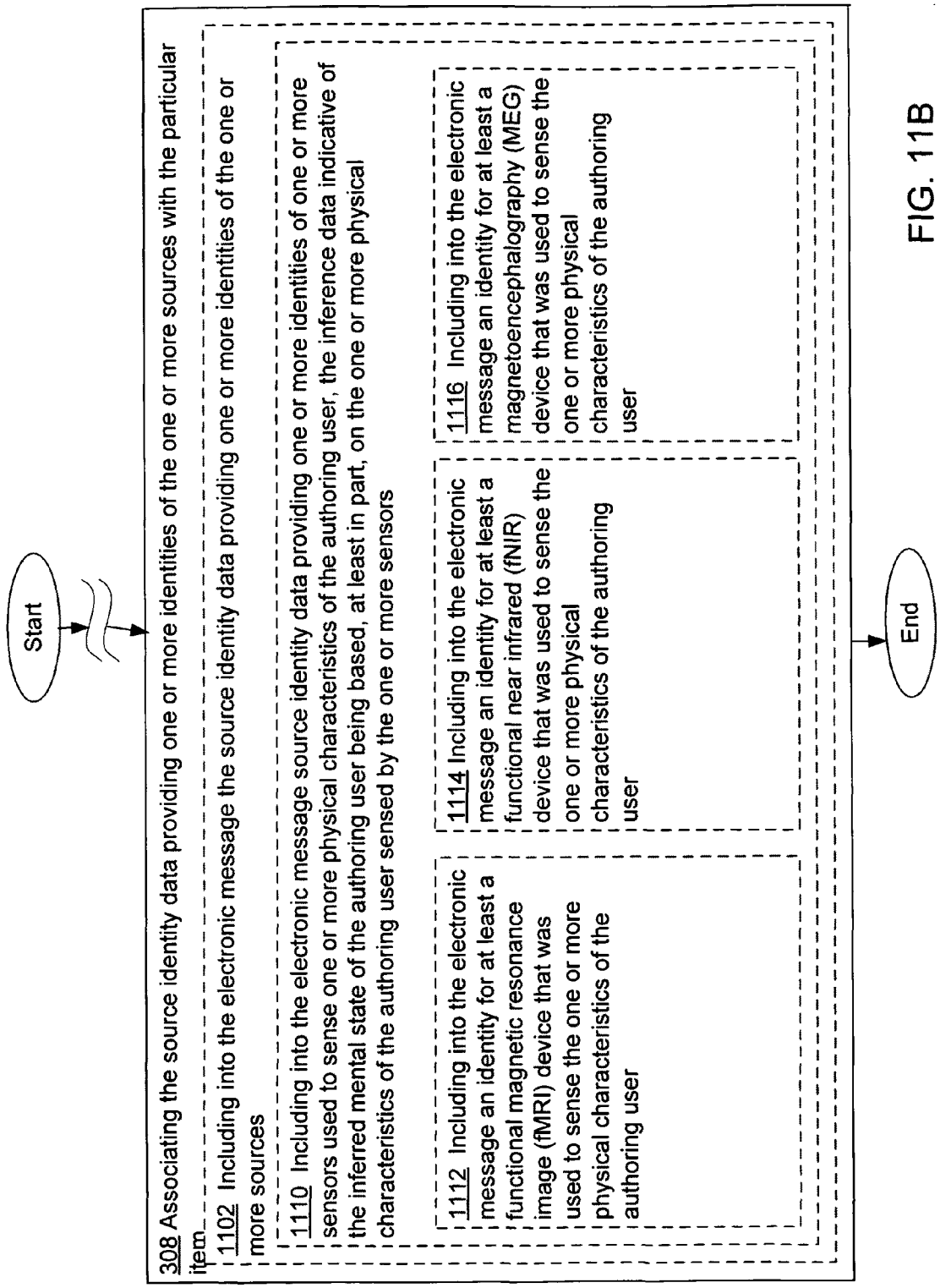
FIG. 11B is a high-level logic flowchart of a process depicting more alternate implementations of the source identity association operation 308 of FIG. 3.
Figure 11C:
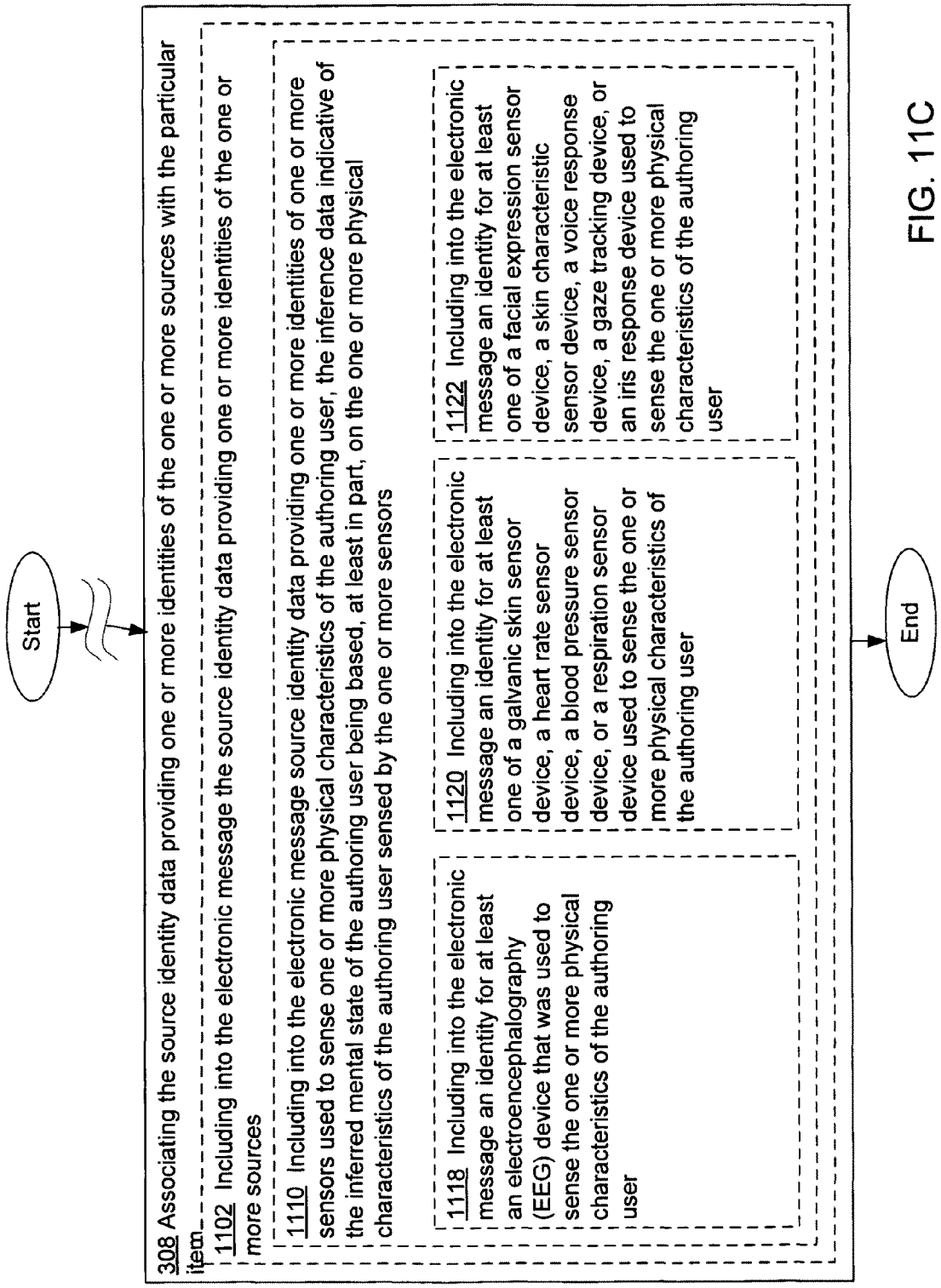
FIG. 11C is a high-level logic flowchart of a process depicting more alternate implementations of the source identity association operation 308 of FIG. 3.

In various implementations, operation 1102 may include one or more additional operations as illustrated in FIGS. 11A to 11C. For example, in some implementations, operation 1102 may include an operation 1104 for including into the electronic message an identity associated with the authoring user as depicted in FIG. 11A. For instance, the source identity inclusion module 111 of the authoring network device 10 including (e.g., inserting into the particular item 21 or proximate to the location of the particular item 21 in the electronic message 20) into the electronic message 20 an identity (e.g., user name or address) associated with the authoring user 18.

In some implementations, operation 1102 may include an operation 1106 for including into the electronic message an identity associated with an inference technique or model used to derive the inference data indicative of the inferred mental state of the authoring user as depicted in FIG. 11A. For instance, the source identity inclusion module 111 of the authoring network device 10 including into the electronic message 20 (e.g., inserting into the particular item 21 or proximate to the location of the particular item 21 in the electronic message 20) an identity (e.g., name) associated with an inference technique or model used to derive the inference data (e.g., as provided by a mental state inference module 106) indicative of the inferred mental state (e.g., state of happiness, state of frustration, state of anger, and so forth) of the authoring user 18.

In some implementations, operation 1102 may include an operation 1108 for including into the electronic message an identity associated with a database or library used to derive the inference data indicative of the inferred mental state of the authoring user as depicted in FIG. 11A. For instance, the source identity inclusion module 111 of the authoring network device 10 including into the electronic message 20 (e.g., inserting into the particular item 21 or proximate to the location of the particular item 21 in the electronic message 20) an identity (e.g. name or address) associated with a database or library (e.g., database or library storing physical characteristic patterns) used to derive the inference data (e.g., as provided by a mental state inference module 106) indicative of the inferred mental state (e.g., state of distress, state of pain, state of trust, and so forth) of the authoring user 18.

In some implementations, operation 1102 may include an operation 1110 for including into the electronic message source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors as depicted in FIGS. 11B and 11C. For instance, the source identity inclusion module 111 of the authoring network device 10 including into the electronic message 20 (e.g., inserting into the particular item 21 or proximate to the location of the particular item 21 in the electronic message 20) source identity data providing one or more identities (e.g., name or model type) of one or more sensors 48 used to sense one or more physical characteristics (e.g., cerebral, cardiopulmonary, and/or systemic physiological characteristics) of the authoring user 18, the inference data (e.g., as provided by an inference data acquisition module 30) indicative of the inferred mental state (e.g., state of approval or disapproval, state of fear, state of surprise, and so forth) of the authoring user 18 being based, at least in part, on the one or more physical characteristics of the authoring user 18 sensed by the one or more sensors 48.

In various implementations, operation 1110 may include one or more additional operations as illustrated in FIGS. 11B and 11C. For example, in some implementations, operation 1110 may include an operation 1112 for including into the electronic message an identity for at least a functional magnetic resonance image (fMRI) device that was used to sense the one or more physical characteristics of the authoring user as depicted in FIG. 11B. For instance, the source identity inclusion module 111 of the authoring network device 10 including into the electronic message 20 an identity (e.g., name or model type) for at least a functional magnetic resonance image (fMRI) device 140 that was used to sense the one or more physical characteristics (e.g., blood oxygen or blood volume changes of a brain) of the authoring user 18.

In some implementations, operation 1110 may include an operation 1114 for including into the electronic message an identity for at least a functional near infrared (fNIR) device that was used to sense the one or more physical characteristics of the authoring user as depicted in FIG. 11B. For instance, the source identity inclusion module 111 of the authoring network device 10 including into the electronic message 20 an identity (e.g., name or model type) for at least a functional near infrared (fNIR) device 141 that was used to sense the one or more physical characteristics (e.g., blood oxygen or blood volume changes of a brain) of the authoring user 18.

In some implementations, operation 1110 may include an operation 1116 for including into the electronic message an identity for at least a magnetoencephalography (MEG) device that was used to sense the one or more physical characteristics of the authoring user as depicted in FIG. 11B. For instance, the source identity inclusion module 111 of the authoring network device 10 including into the electronic message 20 an identity (e.g., name or model type) for at least a magnetoencephalography (MEG) device 143 that was used to sense the one or more physical characteristics (e.g., one or more characteristics associated with electrical activities of a brain) of the authoring user 18.

In some implementations, operation 1110 may include an operation 1118 for including into the electronic message an identity for at least an electroencephalography (EEG) device that was used to sense the one or more physical characteristics of the authoring user as depicted in FIG. 11C. For instance, the source identity inclusion module 111 of the authoring network device 10 including into the electronic message 20 an identity (e.g., name or model type) for at least an electroencephalography (EEG) device 142 that was used to sense the one or more physical characteristics (e.g., one or more characteristics associated with electrical activities of a brain) of the authoring user 18.

In some implementations, operation 1110 may include an operation 1120 for including into the electronic message an identity for at least one of a galvanic skin sensor device, a heart rate sensor device, a blood pressure sensor device, or a respiration sensor device used to sense the one or more physical characteristics of the authoring user as depicted in FIG. 11C. For instance, the source identity inclusion module 111 of the authoring network device 10 including into the electronic message 20 an identity (e.g., name or model type) for at least one of a galvanic skin sensor device 144, a heart rate sensor device 145, a blood pressure sensor device 146, or a respiration sensor device 147 used to sense the one or more physical characteristics (e.g., galvanic skin response, heart rate, blood pressure, or respiration) of the authoring user 18.

In some implementations, operation 1110 may include an operation 1122 for including into the electronic message an identity for at least one of a facial expression sensor device, a skin characteristic sensor device, a voice response device, a gaze tracking device, or an iris response device used to sense the one or more physical characteristics of the authoring user as depicted in FIG. 11C. For instance, the source identity inclusion module 111 of the authoring network device 10 including into the electronic message 20 an identity (e.g., name or model type) for at least one of a facial expression sensor device 148, a skin characteristic sensor device 149, a voice response device 150, a gaze tracking device 151, or an iris response device 152 used to sense the one or more physical characteristics (e.g., facial expression, skin characteristic, voice characteristic, eye movement, or iris characteristic) of the authoring user 18.

Figure 12A:
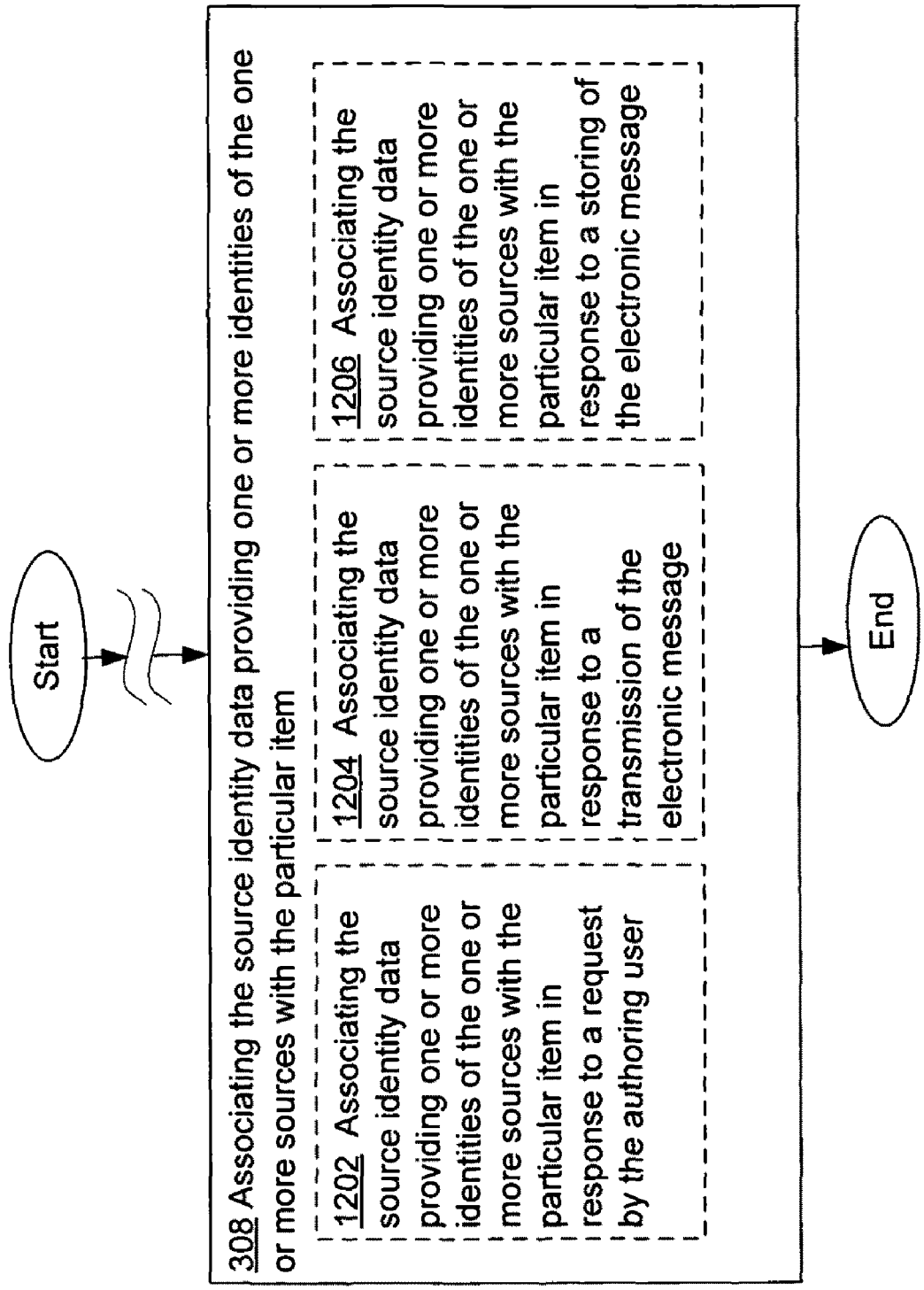
FIG. 12A is a high-level logic flowchart of a process depicting more alternate implementations of the source identity association operation 308 of FIG. 3.
Figure 12B:
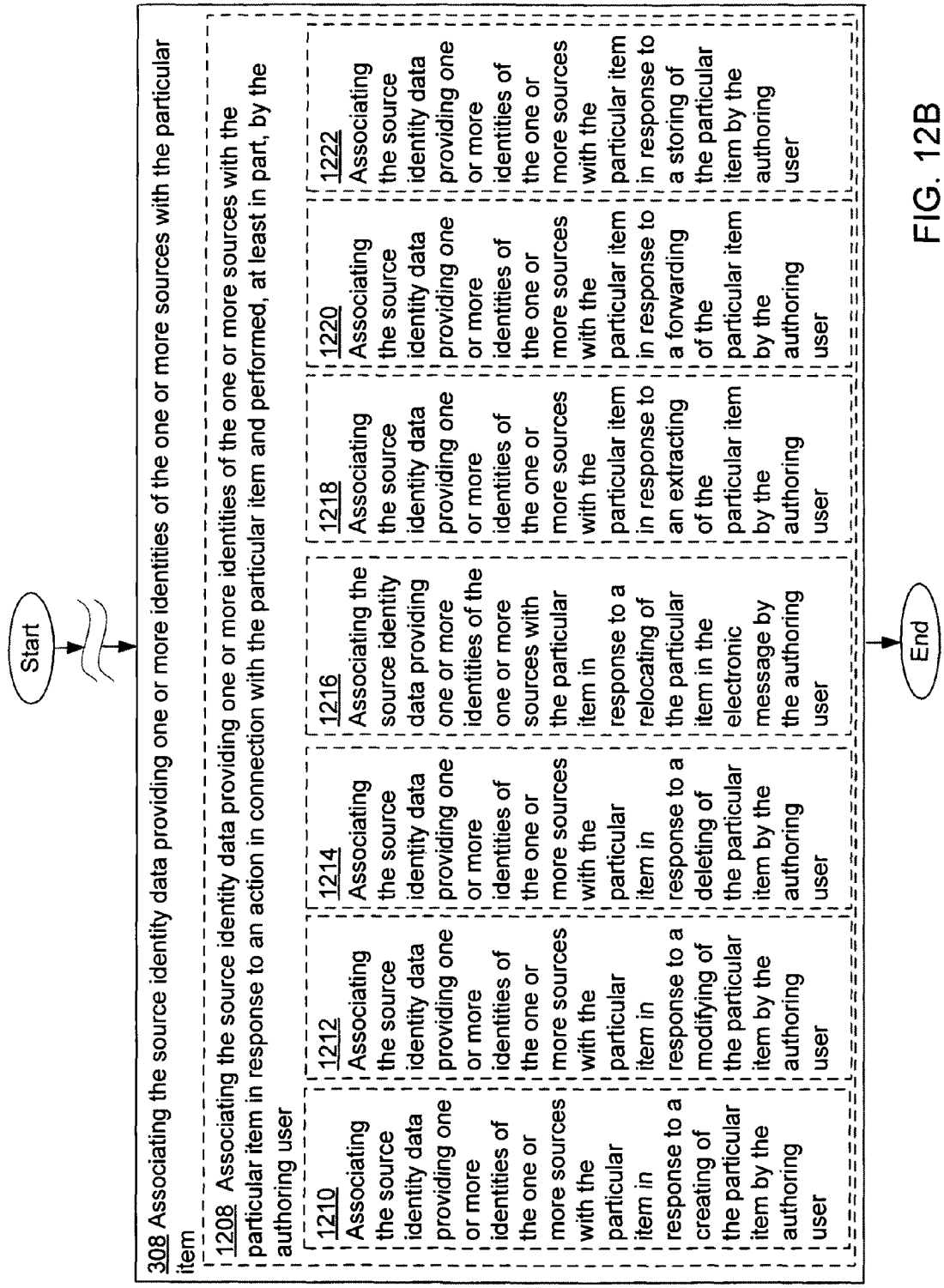
FIG. 12B is a high-level logic flowchart of a process depicting more alternate implementations of the source identity association operation 308 of FIG. 3.
Figure 12C:
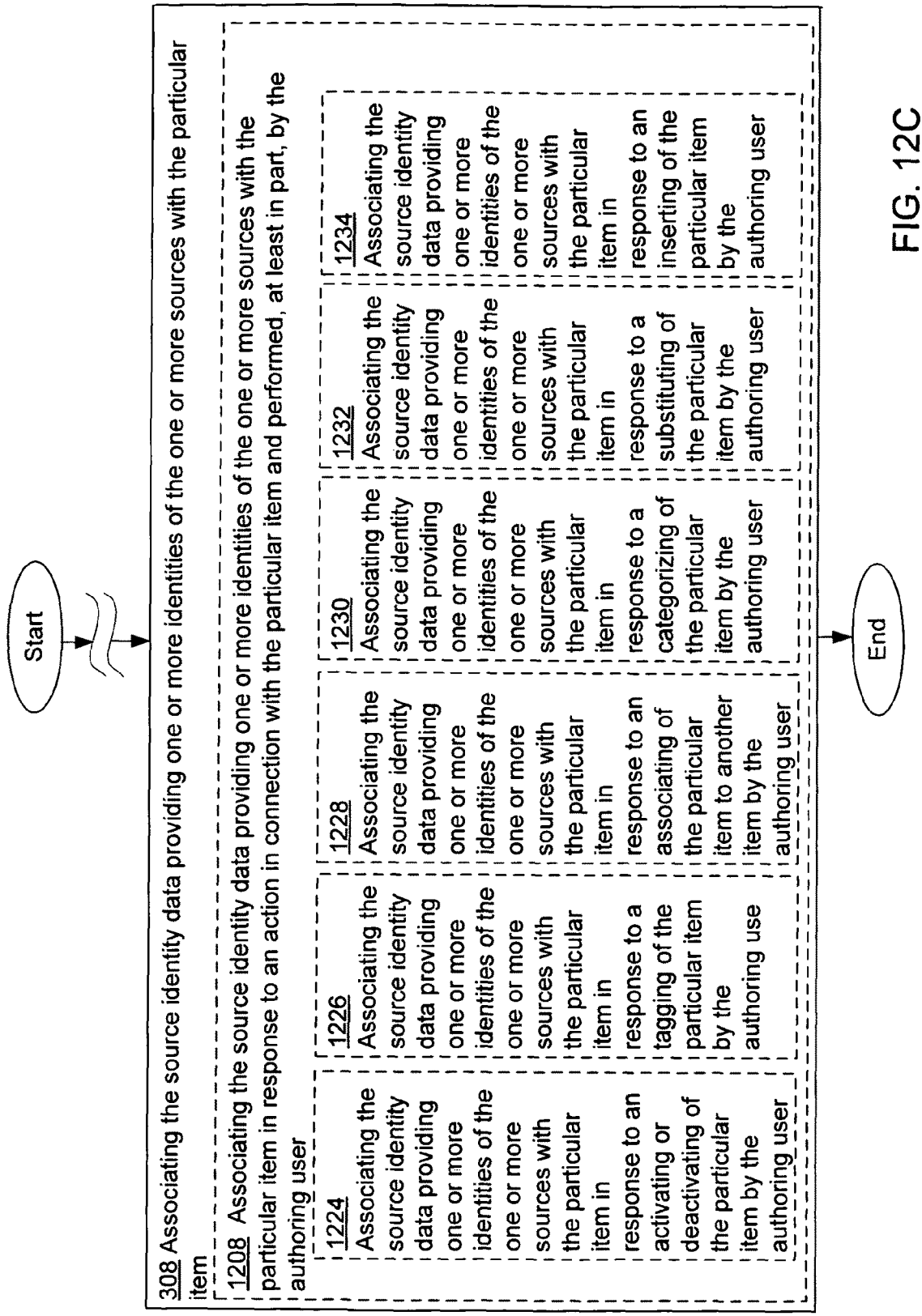
FIG. 12C is a high-level logic flowchart of a process depicting more alternate implementations of the source identity association operation 308 of FIG. 3.

As illustrated in FIGS. 12A to 12C, the source identity association operation 308 of FIG. 3 may include one or more additional operations in various alternative embodiments. For example, in various implementations, the source identity association operation 308 may include an operation 1202 for associating the source identity data providing one or more identities of the one or more sources with the particular item in response to a request by the authoring user as depicted in FIG. 12A. For instance, the source identity association module 33 of the authoring network device 10 associating the source identity data providing one or more identities of the one or more sources with the particular item 21 (e.g., by linking the source identity data providing one or more identities to the particular item 21 via, for example, a hyperlink, or by including the source identity data providing one or more identities into the particular item 21 or into the electronic message 20) in response to a request by the authoring user 18 and made through, for example, a user interface 44.

In some implementations, the source identity association operation 308 may include an operation 1204 for associating the source identity data providing one or more identities of the one or more sources with the particular item in response to a transmission of the electronic message as depicted in FIG. 12A. For instance, the source identity association module 33 of the authoring network device 10 associating (e.g., by linking the source identity data providing one or more identities to the particular item 21 via, for example, a hyperlink, or by including the source identity data providing one or more identities into the particular item 21 or into the electronic message 20) the source identity data providing one or more identities (e.g., name or names) of the one or more sources (e.g., inference technique or model) with the particular item 21 in response to a transmission (e.g., via, for example, a network communication interface 42) of the electronic message 20.

In some implementations, the source identity association operation 308 may include an operation 1206 for associating the source identity data providing one or more identities of the one or more sources with the particular item in response to a storing of the electronic message as depicted in FIG. 12A. For instance, the source identity association module 33 of the authoring network device 10 associating (e.g., by linking the source identity data providing one or more identities to the particular item 21 via, for example, a hyperlink, or by including the source identity data providing one or more identities into the particular item 21 or into the electronic message 20) the source identity data providing one or more identities (e.g., names or source types) of the one or more sources (e.g., sensors 48) with the particular item 21 in response to a storing of the electronic message 20 (e.g., into the memory 49).

In various embodiments, the source identity association operation 308 may include an operation 1208 for associating the source identity data providing one or more identities of the one or more sources with the particular item in response to an action in connection with the particular item and performed, at least in part, by the authoring user as depicted in FIGS. 12B and 12C. For instance, the source identity association module 33 of the authoring network device 10 associating the source identity data providing one or more identities (e.g., name, model number, source type, and so forth) of the one or more sources (e.g., sensors 48) with the particular item 21 in response to an action (e.g., executed via an action module 34) in connection with the particular item 21 and performed, at least in part, by the authoring user 18.

As further illustrated in FIGS. 12B and 12C, operation 1208 may further include one or more additional operations in various alternative implementations. For instance, in some implementations, operation 1208 may include an operation 1210 for associating the source identity data providing one or more identities of the one or more sources with the particular item in response to a creating of the particular item by the authoring user as depicted in FIG. 12B. For instance, the source identity association module 33 of the authoring network device 10 associating the source identity data providing one or more identities (e.g., addresses and/or names) of the one or more sources (e.g., authoring user 18, inference technique or model used to derive the inference data, database or library storing physical characteristic patterns used to derive the inference data, sensors 48, and/or other sources) with the particular item 21 in response to a creating (e.g., via a creation module 112) of the particular item 21 by the authoring user 18.

In some implementations, operation 1208 may include an operation 1212 for associating the source identity data providing one or more identities of the one or more sources with the particular item in response to a modifying of the particular item by the authoring user as depicted in FIG. 12B. For instance, the source identity association module 33 of the authoring network device 10 associating the source identity data providing one or more identities (e.g., name, source type, and/or model number) of the one or more sources (e.g., authoring user 18, inference technique or model used to derive the inference data, database or library storing physical characteristic patterns used to derive the inference data, sensors 48, and/or other sources) with the particular item 21 in response to a modifying (e.g., via a modification module 113) of the particular item 21 by the authoring user 18.

In some implementations, operation 1208 may include an operation 1214 for associating the source identity data providing one or more identities of the one or more sources with the particular item in response to a deleting of the particular item by the authoring user as depicted in FIG. 12B. For instance, the source identity association module 33 of the authoring network device 10 associating the source identity data providing one or more identities (e.g., name, model number, and/or source type) of the one or more sources (e.g., sensors 48) with the particular item 21 in response to a deleting (e.g., via a deletion module 114) of the particular item 21 by the authoring user 18.

In some implementations, operation 1208 may include an operation 1216 for associating the source identity data providing one or more identities of the one or more sources with the particular item in response to a relocating of the particular item in the electronic message by the authoring user as depicted in FIG. 12B. For instance, the source identity association module 33 of the authoring network device 10 associating the source identity data providing one or more identities (e.g., name) of the one or more sources (e.g., inference technique or model) with the particular item 21 in response to a relocating (e.g., via a relocation module 115) of the particular item 21 in the electronic message 20 by the authoring user 18.

In some implementations, operation 1208 may include an operation 1218 for associating the source identity data providing one or more identities of the one or more sources with the particular item in response to an extracting of the particular item by the authoring user as depicted in FIG. 12B. For instance, the source identity association module 33 of the authoring network device 10 associating the source identity data providing one or more identities (e.g., name and/or address) of the one or more sources (e.g., authoring user 18 and/or database or library storing physical characteristic patterns used for inferring mental states) with the particular item 21 in response to an extracting (e.g., via an extraction module 116) of the particular item 21 by the authoring user 18.

In some implementations, operation 1208 may include an operation 1220 for associating the source identity data providing one or more identities of the one or more sources with the particular item in response to a forwarding of the particular item by the authoring user as depicted in FIG. 12B. For instance, the source identity association module 33 of the authoring network device 10 associating the source identity data providing one or more identities (e.g., names and/or source types) of the one or more sources (e.g., one or more sensors 48 including an fMRI device 140, an fNIR device 141, an EEG device 142, an MEG device 143, and/or other sensor devices) with the particular item 21 in response to a forwarding (e.g., via a forwarding module 117) of the particular item 21 by the authoring user 18.

In some implementations, operation 1208 may include an operation 1222 for associating the source identity data providing one or more identities of the one or more sources with the particular item in response to a storing of the particular item by the authoring user as depicted in FIG. 12B. For instance, the source identity association module 33 of the authoring network device 10 associating the source identity data providing one or more identities (e.g., names and/or source types) of the one or more sources (e.g., one or more sensors 48 including an fMRI device 140, an fNIR device 141, an EEG device 142, an MEG device 143, and/or other sensor devices) with the particular item 21 in response to a storing (e.g., storing into memory 49) of the particular item 21 by the authoring user 18.

In some implementations, operation 1208 may include an operation 1224 for associating the source identity data providing one or more identities of the one or more sources with the particular item in response to an activating or deactivating of the particular item by the authoring user as depicted in FIG. 12C. For instance, the source identity association module 33 of the authoring network device 10 associating the source identity data providing one or more identities (e.g., names and/or source types) of the one or more sources (e.g., one or more sensors 48 including an fMRI device 140, an fNIR device 141, an EEG device 142, an MEG device 143, and/or other sensor devices) with the particular item 21 in response to an activating or deactivating (e.g., via an activating or deactivating module 119) of the particular item 21 by the authoring user 18.

In some implementations, operation 1208 may include an operation 1226 for associating the source identity data providing one or more identities of the one or more sources with the particular item in response to a tagging of the particular item by the authoring user as depicted in FIG. 12C. For instance, the source identity association module 33 of the authoring network device 10 associating the source identity data providing one or more identities (e.g., names and/or source types) of the one or more sources (e.g., one or more sensors 48 including an fMRI device 140, an fNIR device 141, an EEG device 142, an MEG device 143, and/or other sensor devices) with the particular item 21 in response to a tagging (e.g., via a tagging module 120) of the particular item 21 by the authoring user 18.

In some implementations, operation 1208 may include an operation 1228 for associating the source identity data providing one or more identities of the one or more sources with the particular item in response to an associating of the particular item to another item by the authoring user as depicted in FIG. 12C. For instance, the source identity association module 33 of the authoring network device 10 associating the source identity data providing one or more identities (e.g., names and/or source types) of the one or more sources (e.g., one or more sensors 48 including an fMRI device 140, an fNIR device 141, an EEG device 142, an MEG device 143, and/or other sensor devices) with the particular item 21 in response to an associating (e.g., via an associating module 121) of the particular item 21 to another item (e.g., an item included in the electronic message 21 or external to the electronic message 21) by the authoring user 18.

In some implementations, operation 1208 may include an operation 1230 for associating the source identity data providing one or more identities of the one or more sources with the particular item in response to a categorizing of the particular item by the authoring user as depicted in FIG. 12C. For instance, the source identity association module 33 of the authoring network device 10 associating the source identity data providing one or more identities (e.g., names and/or source types) of the one or more sources (e.g., one or more sensors 48 including an fMRI device 140, an fNIR device 141, an EEG device 142, an MEG device 143, and/or other sensor devices) with the particular item 21 in response to a categorizing (e.g., via a categorizing module 122) of the particular item 21 by the authoring user 18.

In some implementations, operation 1208 may include an operation 1232 for associating the source identity data providing one or more identities of the one or more sources with the particular item in response to a substituting of the particular item by the authoring user as depicted in FIG. 12C. For instance, the source identity association module 33 of the authoring network device 10 associating the source identity data providing one or more identities (e.g., names and/or source types) of the one or more sources (e.g., one or more sensors 48 including an fMRI device 140, an fNIR device 141, an EEG device 142, an MEG device 143, and/or other sensor devices) with the particular item 21 in response to a substituting (e.g., via a substituting module 123) of the particular item 21 by the authoring user 18.

In some implementations, operation 1208 may include an operation 1234 for associating the source identity data providing one or more identities of the one or more sources with the particular item in response to an inserting of the particular item by the authoring user as depicted in FIG. 12C. For instance, the source identity association module 33 of the authoring network device 10 associating the source identity data providing one or more identities (e.g., names and/or source types) of the one or more sources (e.g., one or more sensors 48 including an fMRI device 140, an fNIR device 141, an EEG device 142, an MEG device 143, and/or other sensor devices) with the particular item 21 in response to an inserting (e.g., via an inserting module 124) of the particular item 21 into, for example, the electronic message 21 by the authoring user 18.

Although it was described in the above description that certain physical characteristics of the authoring user 18 are observed and sensed, other types of physical characteristics may also be observed and sensed. For example, in the above it was described that in some implementations, blood oxygen or blood volume changes of a brain associated with the authoring user 18 may be sensed and observed, other characteristics of the brain associated with the authoring user 18 may also be sensed and observed including, for example, metabolic changes associated with the brain. Such characteristics may be sensed using, for example, a positron emission tomography (PET) scanner.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A computationally-implemented system, comprising:
   means for acquiring inference data indicative of an inferred mental state of an authoring user in connection with at least a particular item of an electronic message;
   means for acquiring source identity data providing one or more identities of one or more sources that provide a basis, at least in part, for the inference data indicative of the inferred mental state of the authoring user;
   means for associating the inference data indicative of the inferred mental state of the authoring user with the particular item, wherein said means for associating the inference data indicative of the inferred mental state of the authoring user with the particular item comprises:
      means for including into the electronic message the inference data indicative of the inferred mental state of the authoring user, wherein said means for including into the electronic message the inference data indicative of the inferred mental state of the authoring user comprises:
         means for including into the electronic message inference data indicative of the inferred mental state of the authoring user that was obtained based, at least in part, on one or more physical characteristics of the authoring user sensed during or proximate to an action executed in connection with the particular item and performed, at least in part, by the authoring user, wherein said means for including into the electronic message inference data indicative of the inferred mental state of the authoring user that was obtained based, at least in part, on one or more physical characteristics of the authoring user sensed during or proximate to an action executed in connection with the particular item and performed, at least in part, by the authoring user comprises:
            means for including into the electronic message inference data indicative of the inferred mental state of the authoring user that was obtained based on at least one cerebral characteristic of the authoring user sensed during or proximate to an action executed in connection with the particular item and performed, at least in part, by the authoring user; and
   means for associating the source identity data providing one or more identities of the one or more sources with the particular item.

2. The computationally-implemented system of claim 1, wherein said means for acquiring inference data indicative of an inferred mental state of an authoring user in connection with at least a particular item of an electronic message comprises:
   means for determining the inference data indicative of the inferred mental state of the authoring user based on one or more physical characteristics of the authoring user.

3. The computationally-implemented system of claim 2, wherein said determining the inference data indicative of the inferred mental state of the authoring user based on one or more physical characteristics of the authoring user comprises:
   means for observing the one or more physical characteristics of the authoring user during or proximate to an action executed in connection with the particular item and performed, at least in part, by the authoring user.

4. The computationally-implemented system of claim 3, wherein said means for observing the one or more physical characteristics of the authoring user during or proximate to an action executed in connection with the particular item and performed, at least in part, by the authoring user comprises:
   means for inferring a mental state of the authoring user based, at least in part, on the observing of the one or more physical characteristics of the authoring user during or proximate to the action executed in connection with the particular item and performed, at least in part, by the authoring user.

5. The computationally-implemented system of claim 1, wherein said means for acquiring source identity data providing one or more identities of one or more sources that provide a basis, at least in part, for the inference data indicative of the inferred mental state of the authoring user comprises:
   means for acquiring the source identity data providing one or more identities of the one or more sources from the one or more sources.

6. The computationally-implemented system of claim 1, wherein said means for acquiring source identity data providing one or more identities of one or more sources that provide a basis, at least in part, for the inference data indicative of the inferred mental state of the authoring user comprises:
 means for acquiring the source identity data providing one or more identities of the one or more sources from memory.

7. The computationally-implemented system of claim 1, wherein said means for acquiring source identity data providing one or more identities of one or more sources that provide a basis, at least in part, for the inference data indicative of the inferred mental state of the authoring user comprises:
 means for acquiring an identity associated with the authoring user.

8. The computationally-implemented system of claim 1, wherein said means for acquiring source identity data providing one or more identities of one or more sources that provide a basis, at least in part, for the inference data indicative of the inferred mental state of the authoring user comprises:
 means for acquiring an identity associated with an inference technique or model used to derive the inference data indicative of the inferred mental state of the authoring user.

9. The computationally-implemented system of claim 1, wherein said means for acquiring source identity data providing one or more identities of one or more sources that provide a basis, at least in part, for the inference data indicative of the inferred mental state of the authoring user comprises:
 means for acquiring an identity associated with a database or library used to derive the inference data indicative of the inferred mental state of the authoring user.

10. The computationally-implemented system of claim 1, wherein said means for acquiring source identity data providing one or more identities of one or more sources that provide a basis, at least in part, for the inference data indicative of the inferred mental state of the authoring user comprises:
 means for acquiring source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors.

11. The computationally-implemented system of claim 10, wherein said means for acquiring source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
 means for acquiring an identity for at least a functional magnetic resonance image (fMRI) device that was used to sense the one or more physical characteristics of the authoring user.

12. The computationally-implemented system of claim 10, wherein said means for acquiring source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
 means for acquiring an identity for at least a functional near infrared (fNIR) device that was used to sense the one or more physical characteristics of the authoring user.

13. The computationally-implemented system of claim 10, wherein said means for acquiring source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
 means for acquiring an identity for at least a magnetoencephalography (MEG) device that was used to sense the one or more physical characteristics of the authoring user.

14. The computationally-implemented system of claim 10, wherein said means for acquiring source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
 means for acquiring an identity for at least an electroencephalography (EEG) device that was used to sense the one or more physical characteristics of the authoring user.

15. The computationally-implemented system of claim 10, wherein said means for acquiring source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
 means for acquiring an identity for at least one of a galvanic skin sensor device, heart rate sensor device, a blood pressure sensor device, or a respiration sensor device used to sense the one or more physical characteristics of the authoring user.

16. The computationally-implemented system of claim 10, wherein said means for acquiring source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
 means for acquiring an identity for at least one of a facial expression sensor device, a skin characteristic sensor device, a voice response device, a gaze tracking device, or an iris response device used to sense the one or more physical characteristics of the authoring user.

17. The computationally-implemented system of claim 1, wherein said means for including into the electronic message the inference data indicative of the inferred mental state of the authoring user comprises:
 means for including into to the electronic message a time stamp associated with the inference data indicative of the inferred mental state of the authoring user, the time stamp corresponding to a time stamp associated with an action performed by the authoring user in connection with the particular item.

18. The computationally-implemented system of claim 1, wherein said means for including into the electronic message inference data indicative of the inferred mental state of the authoring user that was obtained based, at least in part, on one or more physical characteristics of the authoring user sensed during or proximate to an action executed in connection with the particular item and performed, at least in part, by the authoring user comprises:

means for including into the electronic message inference data indicative of the inferred mental state of the authoring user that was obtained based on at least one cardiopulmonary characteristic of the authoring user sensed during or proximate to an action executed in connection with the particular item and performed, at least in part, by the authoring user.

19. The computationally-implemented system of claim 1, wherein said means for including into the electronic message inference data indicative of the inferred mental state of the authoring user that was obtained based, at least in part, on one or more physical characteristics of the authoring user sensed during or proximate to an action executed in connection with the particular item and performed, at least in part, by the authoring user comprises:

means for including into the electronic message inference data indicative of the inferred mental state of the authoring user that was obtained based on at least one systemic physiological characteristic of the authoring user sensed during or proximate to an action executed in connection with the particular item and performed, at least in part, by the authoring user.

20. The computationally-implemented system of claim 1, wherein said means for including into the electronic message inference data indicative of the inferred mental state of the authoring user that was obtained based, at least in part, on one or more physical characteristics of the authoring user sensed during or proximate to an action executed in connection with the particular item and performed, at least in part, by the authoring user comprises:

means for including into the electronic message inference data indicative of the inferred mental state of the authoring user that was obtained based, at least in part, on at least one of galvanic skin response, heart rate, blood pressure, or respiration of the authoring user sensed during or proximate to the action executed in connection with the particular item.

21. The computationally-implemented system of claim 1, wherein said means for including into the electronic message inference data indicative of the inferred mental state of the authoring user that was obtained based, at least in part, on one or more physical characteristics of the authoring user sensed during or proximate to an action executed in connection with the particular item and performed, at least in part, by the authoring user comprises:

means for including into the electronic message inference data indicative of the inferred mental state of the authoring user that was obtained based, at least in part, on at least one of blood oxygen or blood volume changes of a brain of the authoring user sensed during or proximate to the action executed in connection with the particular item.

22. The computationally-implemented system of claim 1, wherein said means for including into the electronic message inference data indicative of the inferred mental state of the authoring user that was obtained based, at least in part, on one or more physical characteristics of the authoring user sensed during or proximate to an action executed in connection with the particular item and performed, at least in part, by the authoring user comprises:

means for including into the electronic message inference data indicative of the inferred mental state of the authoring user that was obtained based, at least in part, on electrical activity of a brain associated with the authoring user.

23. The computationally-implemented system of claim 1, wherein said means for including into the electronic message inference data indicative of the inferred mental state of the authoring user that was obtained based, at least in part, on one or more physical characteristics of the authoring user sensed during or proximate to an action executed in connection with the particular item and performed, at least in part, by the authoring user comprises:

means for including into the electronic message inference data indicative of the inferred mental state of the authoring user that was obtained based, at least in part, on at least one of facial expression, skin characteristic, voice characteristic, eye movement, or iris dilation of the authoring user sensed during or proximate to the action executed in connection with the particular item.

24. The computationally-implemented system of claim 1, wherein said means for including into the electronic message inference data indicative of the inferred mental state of the authoring user that was obtained based, at least in part, on one or more physical characteristics of the authoring user sensed during or proximate to an action executed in connection with the particular item and performed, at least in part, by the authoring user comprises:

means for including into the electronic message an indication of an action in connection with the particular item and performed, at least in part, by the authoring user.

25. The computationally-implemented system of claim 1, wherein said means for associating the source identity data providing one or more identities of the one or more sources with the particular item comprises:

means for including into the electronic message the source identity data providing one or more identities of the one or more sources.

26. The computationally-implemented system of claim 25, wherein said means for including into the electronic message the source identity data providing one or more identities of the one or more sources comprises:

means for including into the electronic message an identity associated with the authoring user.

27. The computationally-implemented system of claim 25, wherein said means for including into the electronic message the source identity data providing one or more identities of the one or more sources comprises:

means for including into the electronic message an identity associated with an inference technique or model used to derive the inference data indicative of the inferred mental state of the authoring user.

28. The computationally-implemented system of claim 25, wherein said means for including into the electronic message the source identity data providing one or more identities of the one or more sources comprises:

means for including into the electronic message an identity associated with a database or library used to derive the inference data indicative of the inferred mental state of the authoring user.

29. The computationally-implemented system of claim 25, wherein said means for including into the electronic message the source identity data providing one or more identities of the one or more sources comprises:

means for including into the electronic message source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors.

30. The computationally-implemented system of claim 29, wherein said means for including into the electronic message source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
  means for including into the electronic message an identity for at least a functional magnetic resonance image (fMRI) device that was used to sense the one or more physical characteristics of the authoring user.

31. The computationally-implemented system of claim 29, wherein said means for including into the electronic message source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
  means for including into the electronic message an identity for at least a functional near infrared (fNIR) device that was used to sense the one or more physical characteristics of the authoring user.

32. The computationally-implemented system of claim 29, wherein said means for including into the electronic message source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
  means for including into the electronic message an identity for at least a magnetoencephalography (MEG) device that was used to sense the one or more physical characteristics of the authoring user.

33. The computationally-implemented system of claim 29, wherein said means for including into the electronic message source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
  means for including into the electronic message an identity for at least an electroencephalography (EEG) device that was used to sense the one or more physical characteristics of the authoring user.

34. The computationally-implemented system of claim 29, wherein said means for including into the electronic message source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
  means for including into the electronic message an identity for at least one of a galvanic skin sensor device, a heart rate sensor device, a blood pressure sensor device, or a respiration sensor device used to sense the one or more physical characteristics of the authoring user.

35. The computationally-implemented system of claim 29, wherein said means for including into the electronic message source identity data providing one or more identities of one or more sensors used to sense one or more physical characteristics of the authoring user, the inference data indicative of the inferred mental state of the authoring user being based, at least in part, on the one or more physical characteristics of the authoring user sensed by the one or more sensors comprises:
  means for including into the electronic message an identity for at least one of a facial expression sensor device, a skin characteristic sensor device, a voice response device, a gaze tracking device, or an iris response device used to sense the one or more physical characteristics of the authoring user.

36. The computationally-implemented system of claim 1, wherein said means for associating the source identity data providing one or more identities of the one or more sources with the particular item comprises:
  means for associating the source identity data providing one or more identities of the one or more sources with the particular item in response to a request by the authoring user.

37. The computationally-implemented system of claim 1, wherein said means for associating the source identity data providing one or more identities of the one or more sources with the particular item comprises:
  means for associating the source identity data providing one or more identities of the one or more sources with the particular item in response to a transmission of the electronic message.

38. The computationally-implemented system of claim 1, wherein said means for associating the source identity data providing one or more identities of the one or more sources with the particular item comprises:
  means for associating the source identity data providing one or more identities of the one or more sources with the particular item in response to a storing of the electronic message.

39. The computationally-implemented system of claim 1, wherein said means for associating the source identity data providing one or more identities of the one or more sources with the particular item comprises:
  means for associating the source identity data providing one or more identities of the one or more sources with the particular item in response to an action executed in connection with the particular item and performed, at least in part, by the authoring user.

\* \* \* \* \*

UNITED STATES PATENT AND TRADEMARK OFFICE
CERTIFICATE OF CORRECTION

PATENT NO.         : 8,065,360 B2                                           Page 1 of 1
APPLICATION NO.    : 12/229517
DATED              : November 22, 2011
INVENTOR(S)        : Jung et al.

It is certified that error appears in the above-identified patent and that said Letters Patent is hereby corrected as shown below:

In Col. 1, line 45 "Ser. No. 12/288,801, entitled ACQUISITION AND PRE-" should read -- Ser. No. 12/288,008, entitled ACQUISITION AND PRE --

In Col. 58, line 57, claim 17 "means for including into to the electronic message a time" should read -- means for including into the electronic message a time --

Signed and Sealed this
Twenty-seventh Day of March, 2012

David J. Kappos
*Director of the United States Patent and Trademark Office*